(12) United States Patent
Beeley et al.

(10) Patent No.: US 6,420,563 B1
(45) Date of Patent: Jul. 16, 2002

(54) SMALL MOLECULE MODULATORS OF G PROTEIN-COUPLED RECEPTOR SIX

(75) Inventors: Nigel R. A. Beeley, Solana Beach; Dominic P. Behan, San Diego; Derek T. Chalmers, Cardiff; Frederique Menzaghi; Sonja Strah-Pleynet, both of San Diego, all of CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 0 days.

(21) Appl. No.: 09/513,838

(22) Filed: Feb. 25, 2000

Related U.S. Application Data

(60) Provisional application No. 60/094,879, filed on Jul. 31, 1998, provisional application No. 60/106,300, filed on Oct. 30, 1998, provisional application No. 60/110,906, filed on Dec. 4, 1998, provisional application No. 60/121,851, filed on Feb. 26, 1999, provisional application No. 60/173,850, filed on Dec. 30, 1999, and provisional application No. 60/174,428, filed on Jan. 4, 2000.

(51) Int. Cl.$^7$ .................. C07D 401/12; C07D 403/12; C07D 413/12; C07D 417/12
(52) U.S. Cl. .................. 546/273.1; 514/338; 514/341; 514/378; 514/387; 514/397; 514/398; 546/274.4; 546/211.4; 546/314.4; 546/315.4; 546/323.1; 548/240
(58) Field of Search .................. 548/323.1, 303.1, 548/311.4, 315.4, 314.4, 240; 514/397, 398, 338, 341; 546/273.1, 274.4

(56) References Cited

U.S. PATENT DOCUMENTS

| | | | | |
|---|---|---|---|---|
| 3,232,933 A | * | 2/1966 | Gumdel et al. | 548/323.1 |
| 5,514,578 A | | 5/1996 | Hogness et al. | 435/240.2 |
| 5,532,157 A | | 7/1996 | Fink | 435/240.2 |
| 5,573,944 A | | 11/1996 | Kirschner et al. | 435/252.3 |
| 5,639,616 A | | 6/1997 | Liao et al. | 435/7.1 |
| 5,750,353 A | | 5/1998 | Kopin et al. | 435/7.21 |

FOREIGN PATENT DOCUMENTS

| | | |
|---|---|---|
| CA | 2135253 | 5/1996 |
| WO | WO 97/11159 | 9/1996 |
| WO | WO 99/09024 | 2/1999 |

OTHER PUBLICATIONS

Gdaniec, M., et al. "Crystal and molecular structure of 3–(4–chlor=benzoylimino)–5,6–dihydro–3H–imidazo[2,1–c]–1,2,4–dithiazole," *Chemical Abstracts XP–002177674*, 1986, 111(20), 1 page.

Gdaniec, M., et al., "Crystal and molecular structure of 3–(4–chlorobenzoylimino)–5,6–dih ydro–3H–imidazo[2,1–c]–1,2,4–dithiazole," *Chemical Abstracts XP–002177676*, 1989, 19(3), 1 page.

Saczewaki, F., "Synthesis, transformation and tuberculostatic activity of 1–(N–aroylthiocarbamoyl)imidazolidine–2–thiones," *Chemical Abstracts XP–002177673*, 1993, 121(7), 1 page.

Saczewski, F., "Synthesis transformations and tuberculostatic activity of1–aroylthiocarbamoyl)imidazolidine–2–thiones," *Chemical Abstracts XP–002177675*, 1993, 1 page.

Saczewski, F., et al., "Synthesis and transformations of 3–benzoylimino–5,6–dihydro–3H–imidazo[2,1–c][1,2,4] dithiazole," *Communications*, Sep. 1986, 751–753.

Alla, S.A. et al., "Extracellular domains of the bradykinin B2 receptor involved in ligand binding and agonist sensing defined by anti–peptide antibodies," *J. Biol. Chem.*, 1996, 271, 1748–1755.

Advenier, C. et al., "Effects on the isolated human bronchus of SR 48968, a potent and selective nonpeptide antagonist of the neurokinin A (NK$_2$) receptors," *Am. Rev. Respir. Dis.*, 1992, 146(5, Pt. 1), 1177–1181.

Alexander, W.S. et al., "Point mutations within the dimer interface homology domain of c–Mpl induce constitutive receptor activity and tumorigenicity," *EMBO J.*, 1995, 14(22), 5569–5578.

Arvanitikis, L. et al., "Human herpesvirus KSHV encodes a constitutively active G–protein–coupled receptor linked to cell proliferation," *Nature*, 1997, 385, 347–349.

Barker, E.L. et al., "Constitutively active 5–hydroxytryptamine$_{2C}$ receptors reveal novel inverse agonist activity of receptor ligands," *J. Biol. Chem.*, 1994, 269(16), 11687–11690.

Baxter, G., "5HT$_2$ receptors: a family re–united?" *Trends Pharmacol. Sci.*, 1995, 16, 105–110.

Besmer, P. et al., "A new acute transforming feline retrovirus and relationship of its oncogene v–kit with the protein kinase gene family," *Nature*, 1986, 320, 415–421.

Blin, N. et al., "Mapping of single amino acid residues required for selective activation of G$_{q/11}$ by the m3 muscarinic acetylcholine receptor," *J. Biol. Chem.*, 1995, 270, 17741–17748.

Bond, R.A. et al., "Inverse agonists and G–protein–coupled receptors," in *Receptor–Based Drug Design*, Leff, P. (ed.), New York, M. Dekker, 1998, 363–377.

Boone, C. et al., "Mutations that alter the third cytoplasmic loop of the a–factor receptor lead to a constitutive and hypersensitive phenotype," *Proc. Natl. Acad. Sci. USA*, 1993, 90(21), 9921–9925.

(List continued on next page.)

Primary Examiner—Floyd D. Higel
(74) Attorney, Agent, or Firm—Woodcock Washburn LLP

(57) ABSTRACT

Disclosed herein are small molecule modulators of the G protein coupled receptor six, methods of making such compounds, and methods of using such compounds.

1 Claim, 11 Drawing Sheets

OTHER PUBLICATIONS

Jensen et al., "mRNA Profiling of Rat Islet Tumors Reveals Nkx 6.1 as a β–Cell–specific Homeodomain Transcription Factor," *J. Biol. Chem.*, 1996, 271(31), 18749–18758.

Konig et al., "Method for Identifying Ligands That Bind to Cloned $G_s$–or $G_i$–Coupled Receptors," *Mol. Cell. Neuro.*, 1991, 2, 331–337.

Leonard, J. et al., "The LIM family transcription factor Is1–1 requires cAMP response element binding protein to promote somatostatin expression in pancreatic islet cells," *Proc. Natl. Acad. Sci. USA*, 1992, 89, 6247–6251.

Marchese, A. et al., "Cloning of Human Genes Encoding Novel G Protein–Coupled Receptors," *Genomics*, 1994, 23, 609–618.

Marks, D.L. et al., "Simultaneous Visualization of Two Cellular mRNA Species in Individual Neurons by Use of a New Double in Situ Hybridization Method," *Mol. & Cell. Neuro.*, 1992, 3, 395–405.

O'Dowd, B. et al., "Cloning and chromosomal mapping of four putative novel human G–protein–coupled receptor genes," *Gene*, 1997, 187, 75–81.

Sakurai T. et al., "Orexins and Orexin Receptors: A Family of Hypothalamic Neuropeptides and G Protein–Coupled Receptors that Regulate Feeding Behavior," *Cell*, 1998, 92, 573–585.

Song, Z.–H. et al., "Molecular Cloning and Chromosomal Localization of Human Genes Encoding Three Closely Related G Protein–Coupled Receptors," *Genomics*, 1995, 28, 347–349.

Suzuki, M. et al., "Regulatable Promoters for Use in Gene Therapy Applications: Modification of the 5'–Flanking Region of the CFTR Gene with Multiple cAMP Response Elements to Support Basal, Low–Level Gene Expression that can be Upregulated by Exogenous Agents that Raise Intracellular Levels of cAMP," *Human Gene Therapy*, 1996, 7, 1883–1893.

Xu, Y. et al., "Identification of Human OGR1, a Novel G Protein–Coupled Receptor That Maps to Chromosome 14," *Genomics*, 1996, 35, 397–402.

Nichols, J.G. et al. (eds.), "Indirect Mechanisms of Synaptic Transmission," in *From Neuron To Brain*, 3rd Edition, Sinauer Associates, Inc., 1992.

Oslo et al. (eds.), in *Remington's Pharmaceutical Sciences*, 16th Edition, Mack Publishing Co., 1980.

Burstein, E.S. et al., "Constitutive activation of chimeric m2/m5 muscarinic receptors and delineation of G–protein coupling selectivity domains," *Biochem. Pharmacol.*, 1996, 51(4), 539–544.

Burstein, E.S. et al., "Amino acid side chains that define muscarinic receptor/G–protein coupling. Studies of the third intracellular loop," *J. Biol. Chem.*, 1996, 271(6), 2882–2885.

Burstein, E.S. et al., "Constitutive activation of muscarinic receptors by the G–protein $G_q$," *FEBS Lett.*, 1995, 363(3), 261–263.

Bylund, D., "International union of pharmacology nomenclature of adrenoceptors," *Pharmacol. Rev.*, 1994, 46, 121–136.

Casey, C. et al., "Constitutively active mutant 5–$HT_{2A}$ serotonin receptors: inverse agonist activity of classical 5$HT_{2A}$ antagonists," *Soc. Neurosci.*, 1996, Abstract #699.10.

Cheatham, B. et al., "Substitution of the erbB–2 oncoprotein transmembrane domain activates the insulin receptor and modulates the action of insulin–receptor substrate 1," *Proc. Natl. Acad. Sci. USA*, 1993, 90, 7336–7340.

Chen, J. et al., "Tethered Ligand Library for Discovery of Peptide Agonists," *J. Biol. Chem.*, 1995, 270, 23398–23401.

Chen, T.S. et al., "Microbial hydroxylation and glucuronidation of the angiotensin II (AII) receptor antagonist MK 954," *J. Antibiot. (Tokyo)*, 1993, 46(1), 131–134.

Chen, W. et al., "A colorimetric assay for measuring activation of $G_s$–and $G_q$–coupled signaling pathways," *Anal. Biochem.*, 1995, 226(2), 349–354.

Chidiac, P. et al., "Inverse agonist activity of β–adrenergic antagonists," *J. Pharm. Exp. Ther.*, 1994, 45, 490–499.

Clozel, M. et al., "In vivo pharmacology of Ro 46–2005, the first synthetic nonpeptide endothelin receptor antagonist: implications for endothelin physiology," *J. Cardiovas. Pharmacol.*, 1993, 22(Suppl. 8), S377–S379.

Collesi, C. et al., "A splicing variant of the RON transcript induces constitutive tyrosine kinase activity and an invasive phenotype," *Mol. Cell. Biol.*, 1996, 16(2), 5518–5526.

Cooper, C.S. et al., "Molecular cloning of a new transforming gene from a chemically transformed human cell line," *Nature*, 1984, 311, 29–33.

De Dios, I. et al., "Effect of L–364,718 (CCK Receptor Antagonist) on Exocrine Pancreatic Secretion of Hydrocortison–Treated Rats," *Pancreas*, 1994, 9(2), 212–218.

Desbois–Mouthon, C. et al., "Deletion of $Asn^{281}$ in the α–subunit of the human insulin receptor causes constitutive activation of the receptor and insulin desensitization," *J. Clin. Endocrinol. Metab.*, 1996, 81(2), 719–727.

Di Renzo, M.F. et al., "Expression of the Met/HGF receptor in normal and neoplastic human tissues," *Oncogene*, 1991, 6(11), 1997–2003.

Di Renzo, M.F. et al., "Overexpression of the c–MET/HGF receptor gene in human thyroid carcinomas," *Oncogene*, 1992, 7, 2549–2553.

Duprez, L. et al., "Germline mutations of the thyrotropin receptor gene cause non–autoimmune autosomal dominant hyperethyroidism," *Nature Genetics*, 1994, 7, 396–401.

Eggericksx, D. et al., "Molecular Cloning of an Orphan G–Protein–Coupled Receptor that Constitutively Activates Adenylate Cyclase," *Biochem. J.*, 1995, 309, 837–843.

Evans, B.E. et al., "Orally Active, Nonpeptide Oxytocin Antagonists," *J. Med. Chem.*, 1992, 35, 3919–3927.

Fu, M. et al., "Functional autoimmune epitope on $α_1$ adrenergic receptors in patients with malignant hypertension," *Lancet*, 1994, 344, 1660–1663.

Furitsu, T. et al., "Identification of Mutations in the Coding Sequence of the Proto–oncogene c–kit in a Human Mast Cell Leukemia Cell Line Causing Ligand–independent Activation of c–kit Product," *J. Clin. Invest.*, 1993, 92, 1736–1744.

Gellai, M. et al., "Nonpeptide Endothelin Receptor Antagonists V: Prevention and Reversal of Acute Renal Failure in the Rat by SB 209670," *J. Pharm. Exp. Therap.*, 1995, 275(1), 200–206.

Gitter, B. et al., "Pharmacological Characterization of LY303870: A Novel Potent and Selective Nonpeptide Substance P (Neurokinin–1) Receptor Antagonist," *J. Pharm. Exp. Therp.*, 1995, 275(2), 737–744.

Gouilleux–Gruart, V. et al., "STAT–Related Transcription Factors are Constitutively Activated in Peripheral Blood Cells from Acute Leukemia Patients," *Blood,* 1996, 87(5), 1692–1697.

Hansson, J.H. et al., "Hypertension caused by a truncated epithelial sodium channel γ subunit: genetic heterogeneity of Liddle syndrome," *Nat. Genet.,* 1995, 11(1), 76–82.

Hasegawa, H. et al., "Two Isoforms of the Prostaglandin E Receptor EP3 Subtype Different in Agonist–independent Constitutive Activity," *J. Biol. Chem.,* 1996, 271(4), 1857–1860.

Hendler, F. et al., "Human Squamous Cell Lung Cancers Express Increased Epidermal Growth Factor Receptors," *J. Clin. Invest.,* 1984, 74, 647–651.

Herrick–Davis, K. et al., "Constitutively Active 5HT2C Serotonin Receptor Created by Site–Directed Mutagenesis," *Soc. Neurosci.,* Abstract No. 699.18.

Hieble, J., "International union of pharmacology. X. Recommendation for nomenclature of 1–adrenoceptors," *Pharm. Rev.,* 1995, 47, 267–270.

Hill, S., "Distribution, Properties, and Functional Characteristics of Three Classes of Histamine Receptor," *Am. Soc. Pharm. Exp. Therap.,* 1990, 42(1), 45–83.

Högger, P. et al., "Activating and Inactivating Mutations in—and C–terminal i3 Loop Junctions of Muscarinic Acetylcholine Hm1 Receptors," *J. Biol. Chem.,* 1995, 270(13), 7405–7410.

Ikeda, H. et al., "Expression and Functional Role of the Proto–oncogene c–kit in Acute Myeloblastic Leukemia Cells," *Blood,* 1991, 78(11), 2962–2968.

Imura, R. et al., "Inhibition by HS–142–1, a novel nonpeptide atrial natriuretic peptide antagonist of microbial origin, of atrial natriuretic peptide–induced relaxation of isolated rabbit aorta through the blockade of guanylyl cyclase–linked receptors," *Mol. Pharm.,* 1992, 42, 982–990.

Jakubik, J. et al., "Constitutive activity of the $M_1$–$M_4$ subtypes of muscarinic receptors in transfected CHO cells and of muscarinic receptors in the heart cells revealed by negative antagonists," *FEBS Letts.,* 1995, 377, 275–279.

Kjelsberg, M.A. et al., "Constitutive activation of the $\alpha_{1B}$–adrenergic receptor by all amino acid substitutions at a single site," *J. Biol. Chem.,* 1992, 267(3), 1430–1433.

Knapp, R. et al., "Molecular biology and pharmacology of cloned opioid receptors," *FASEB J.,* 1995, 9, 516–525.

Kosugi, S. et al., "Characterization of heterogeneous mutations causing constitutive activation of the luteinizing hormone receptor in familial male precocious puberty," *Human Mol. Genetics,* 1995, 4(2), 183–188.

Kosugi, S. et al., "Identification of Thyroid–Stimulating Antibody–Specific Interaction Sites in the N–Terminal Region of the Thyrotropin Receptor," *Mol. Endocrinology,* 1993, 7, 114–130.

Kraus, M. et al., "Demonstration of ligand–dependent signaling by the erbB–3 tyrosine kinase and its constitutive activation in human breast tumor cells," *Proc. Natl. Acad. Sci. USA,* 1993, 90, 2900–2904.

Kudlacz, E. et al., "In Vitro and In Vivo Characterization of MDL 105,212A, a Nonpeptide NK–1/NK–2 Tachykinin Receptor Antagonist," *J. Pharm. Exp. Therap.,* 1996, 277(2), 840–851.

Kuriu, A. et al., "Proliferation of Human Myeloid Leukemia Cell Line Associated with the Tyrosine–Phosphorylation and Activation of the Proto–oncogene c–kit Product," *Blood,* 1991, 78(11), 2834–2840.

Labbé–Jullié, C. et al., "Effect of the nonpeptide neurotensin antagonist, SR 48692, and two enantiomeric analogs, SR 48527 and SR 49711, on neurotension binding and contractile responses in guinea pig ileum and colon," *J. Pharm. Exp. Therap.,* 1994, 271(1), 267–276.

Latronico, A. et al., "A novel mutation of the leuteinizing hormone receptor gene causing male gonadotropin–independent precocious puberty," *J. Clin. Endocrinol. Metabl.,* 1995, 80(8), 2490–2494.

Laue, L. et al., "Genetic heterogeneity of constitutively activating mutations of the human leuteinizing hormone receptor in familial male–limited precocious puberty," *Proc. Natl. Acad. Sci USA,* 1995, 92, 1906–1910.

Løvlie, R. et al., "The $Ca^{2+}$–sensing receptor gene (PCAR1) mutation T151M in isolated autosomal dominant hypoparathyroidism," *Hum. Genet,* 1996, 98, 129–133.

Lefkowitz, R. et al., "Constitutive activity of receptors coupled to guanine nucleotide regulatory proteins," *Trends Pharmacol. Sci.,* 1993, 14, 303–307.

Libermann, T. et al., "Amplification, enhanced expression and possible rearrangement of EGF receptor gene in primary human brain tumours of glial origin," *Nature,* 1985, 313, 144–147.

Liu, C. et al., "Overexpression of c–met proto–oncogene but not epidermal growth factor receptor or c–erbB–2 in primary human colorectal carcinomas," *Oncogene,* 1992, 7, 181–185.

Liu, J. et al., "Molecular mechanisms involved in muscarinic acetylcholine receptor–mediated G protein activation studied by insertion mutagenesis," *J. Biol. Chem.,* 1996, 271(11), 6172–6178.

Lonardo, F. et al., "The normal erbB–2 product is an atypical receptor–like tyrosine kinase with constitutive activity in the absence of ligand," *New Biologist,* 1990, 2(11), 992–1003.

Maenhaut, C. et al., "RDC8 codes for an adenosine A2 receptor with physiological constitutive activity," *Biochem. Biophys. Res. Comm.,* 1990, 173(3), 1169–1178.

Mann, J. et al., "Increased serotonin$_2$ and β–adrenergic receptor binding in the frontal cortices of suicide victims," *Arch. Gen. Psychiatry,* 1986, 43, 954–959.

Martone, R.L. et al., "Human CRF receptor chimeras: Mapping of ligand binding determinants," 26th Meeting of the Society of Neuroscience, Washington, D.C. Nov. 16–21, 1996, Abstract No. 609.8.

Magnusson, Y. et al., "Autoimmunity in idiopathic dilated cardiomyopathy," *Circulation,* 1994, 89, 2760–2767.

Matus–Leibovitch, N. et al., "Truncation of the thyrotropin–releasing hormone receptor carboxyl tail causes constitutive activity and leads to impaired responsiveness in Xenopus Oocytes and AtT20 Cells," *J. Biol. Chem.,* 1995, 270(3), 1041–1047.

Myles, G.M. et al., "Tyrosine 569 in the c–Fms juxtamembrane domain is essential for kinase activity and macrophage colony–stimulating factor–dependent internalization," *Mol. Cell. Biol.,* 1994, 14(7), 4843–4854.

Nanevicz, T. et al., "Thrombin receptor activating mutations," *J. Biol. Chem.,* 1996, 271(2), 702–706.

Natali, P.G. et al., "Expression of the c–Met/HGF receptor in human melanocytic neoplasms: demonstration of the relationship to malignant melanoma tumour progression," *Br. J. Cancer,* 1993, 68, 746–749.

Neilson, K.M. et al., "Constitutive activation of fibroblast growth factor receptor–2 by a point mutation associated with Crouzon syndrome," *J. Biol. Chem.*, 1995, 270(44), 26037–26040.

Oda, S. et al., "Pharmacological profile of HS–142–1, a novel nonpeptide atrial natriuretic peptide (ANP) antagonist of microbial origin. II. Restoration by HS–142–1 of ANP–induced inhibition of aldosterone production in adrenal glomerulosa cells," *J. Pharm. Exp. Ther.*, 1992, 263(1), 241–245.

O'Dowd, B.F. et al., "Site–directed mutagenesis of the cytoplasmic domains of the human β2–adrenergic receptor," *J. Biol. Chem.*, 1988, 263(31), 15985–15992.

Offermanns, S. et al., "$G\alpha_{15}$ and $G\alpha_{16}$ Couple a Wide Variety of Receptors to Phospholipase C," *J. Biol. Chem.*, 1995, 270, 15175–15180.

Palkowitz, A.D. et al., "Structural evolution and pharmacology of a novel series of triacid angiotensin II receptor antagonists," *J. Med. Chem.*, 1994, 37, 4508–4521.

Parent, J. et al., "Mutations of two adjacent amino acids generate inactive and constitutively active forms of the human platelet–activating factor receptor," *J. Biol. Chem.*, 1996, 271(14), 7949–7955.

Parfitt, A.M. et al., "Hypercalcemia due to constitutive activity of the parathyroid hormone (PTH)/PTH–related peptide receptor: comparison with primary hyperparathyroidism," *J. Clin. Endocr. Metabl.*, 1996, 81, 3584–3588.

Parma, J. et al., "Somatic mutations in thyrotropin receptor gene cause hyperfunctioning thyroid adenomas," *Nature*, 1993, 365, 649–651.

Pei, G. et al., "A constitutive active mutant $\beta_2$–adrenergic receptor is constitutively desensitized and phosphorylated," *Proc. Natl. Acad. Sci. USA*, 1994, 91, 2699–2702.

Pendley, C.E. et al., "The gastrin/cholecystokinin–B receptor antagonist L–365,260 reduces basal acid secretion and prevents gastrointestinal damage induced by aspirin, ethanol and cysteamine in the rat," *J. Pharmacol. Exp. Ther.*, 1993, 265(3), 1348–1354.

Peroutka, S., "Serotonin receptor subtypes. Their evolution and clinical relevance," *CNS Drugs*, 1995, 4 (Suppl. 1), 18–27.

Pettibone, D.J. et al., "Development and pharmacological assessment of novel peptide and nonpeptide oxytocin antagonists," *Regul. Pept.*, 1993, 45, 289–293.

Prat, M.P. et al., "The receptor encoded by the human c–Met oncogene is expressed in hepatocytes, epithelial cells and solid tumors," *Int. J. Cancer*, 1991, 49, 323–328.

Prezeua, L. et al., "Changes in the carboxy–terminal domain of metabotropic glutamate receptor 1 by alternate splicing generate receptors with differing agonist–independent activity," *Mol. Pharmacol.*, 1996, 49, 422–429.

Rakovska, A. et al., "Effect of loxiglumide (CR 1505) on CCK–induced contractions and $^3$H–acetylcholine release from guinea–pig gallbladder," *Neuropeptides*, 1993, 25(5), 271–276.

Ren, Q. et al., "Constitutive active mutants of the $\alpha_2$–adrenergic receptor," *J. Biol. Chem.*, 1993, 268, 16483–16487.

Reynolds, E.E. et al., "Pharmacological characterization of PD 156707, an orally active $ET_A$ receptor antagonist," *J. Pharmacol. Exp. Ther.*, 1995, 273(3), 1410–1417.

Robbins, L.S. et al., "Pigmentation phenotypes of variant extension locus alleles result from point mutations that alter MSH receptor function," *Cell*, 1993, 72, 827–834.

Rong, S. et al., "Met expression and sarcoma tumorigenicity," *Cancer*, 1993, 53(22), 5355–5360.

Samama, P. et al., "A mutation–induced activation state of the β–adrenergic receptor," *J. Biol. Chem.*, 1993, 268(7), 4625–4636.*

Sautel, M. et al., "Neuropeptide Y and the nonpeptide antagonist BIBP 3226 share an overlapping binding site at the human Y1 receptor," *Am. Soc. Pharm. Exp. Ther.*, 1996, 50, 285–292.*

Sawutz, D.G. et al., "Pharmacology and structure–activity relationships of the nonpeptide bradykinin receptor antagonist WIN 64338," *Can. J. Physiol. Pharmacol.*, 1995, 73, 805–811.*

Scheer, A. et al., "Constitutively active G protein–coupled receptors: potential mechanisms of receptor activation," *J. Rec. Signal Transduct. Res.*, 1997, 17(1–3), 57–73.*

Scheer, A. et al., "The activation process of the $\alpha_{1B}$–adrenergic receptor: Potential role of protonation and hydrophobicity of a highly conserved aspartate," *Proc. Natl. Acad. Sci. USA*, 1997, 94, 808–813.*

Schwinn, D.A. et al., "Cloning and pharmacological characterization of human Alpha–1 adrenergic receptors: sequence corrections and direct comparison with other species homologues," *J. Pharmacol.*, 1995, 272(1), 134–142.*

Schild, L. et al., "A mutation in the epithelial sodium channel causing Liddle disease increases channel activity in the *Xenopus laevis* oocyte expression system," *Proc. Natl. Acad. Sci. USA*, 1995, 5699–5703.*

Seeman, P. et al., "Dopamine receptor pharmacology," *Trends Pharmacol. Sci.*, 1994, 15, 264–270.*

Seeman, P. et al., "Dopamine D4 receptors elevated in schizophrenia," *Nature*, 1993, 365, 441–445.*

Serradeil–Le Gale, C. et al., "Biochemical and pharmacological properties of SR 49059, a new, potent, nonpeptide antagonist of rat and human vasopressin $V_{1a}$ receptors," *J. Clin. Invest.*, 1993, 92, 224–231.*

Sharif, M. et al., "Malignant transformation by G protein–coupled hormone receptors," *Mol. Cell. Endocrinology*, 1994, 100, 115–119.*

Showers, M.O. et al., "Activation of the erythropoietin receptor by the Friend spleen focus–forming virus gp55 glycoprotein induces constitutive protein tyrosine phosphorylation," *Blood*, 1992, 80(12), 3070–3078.

Skinner, R.H. et al., "Direct measurement of the binding of RAS to neurofibromin using scintillation proximity assay," *Anal. Biochem.*, 1994, 223, 259–265.

Slamon, D.J. et al., "Human breast cancer: correlation of relapse and survival with amplification of HER–2/neu oncogene," *Science*, 1987, 235, 177–181.

Slamon, D. et al., "Studies of the HER–2/neu proto–oncogene in human breast and ovarian cancer," *Science*, 1989, 244, 707—712.

Salomon, Y. et al., "A highly sensitive adenylate cyclase assay," *Anal. Biochem.*, 1974, 58, 541–548.

Spiegel, A.M., "Defects in G protein–coupled signal transduction in human disease," *Ann. Rev. Physiol.*, 1995, 58, 143–170.

ter Laak, A. et al., "Modeling and mutation studies on the histamine $H_1$–receptor agonist binding site reveal different binding modes for $H_1$–agonists: Asp$^{116}$ (TM3) has a constitutive role in receptor stimulation," *J. Computer–Aided Mol. Design*, 1995, 9, 319–330.

Tiberi, M. et al., "High agonist–independent activity is a distinguishing feature of the dopamine D1B receptor subtype," *J. Biol. Chem.,* 1994, 269(45), 27925–27931.

Tsujimura, T. et al., "Constitutive activation of c–kit in FMA3 murine mastocytoma cells caused by deletion of seven amino acids at the juxtamembrane domain," *Blood,* 1996, 87(1), 273–283.

Wang, Z. et al., "Constitutive μ opioid receptor activation as a regulatory mechanism underlying narcotic tolerance and dependence," *Life Sci.,* 1994, 54(20), 339–350.

Watowich, S.S. et al., "Homodimerization and constitutive activation of the erythropoietin receptor," *Proc. Natl. Acad. Sci. USA,* 1992, 89, 2140–2144.

Weber–Nordt, R.M. et al., "Constitutive activation of STAT proteins in primary lymphoid and myeloid leukemia cells and in Epstein–Barr virus (EBV)–related lymphoma cell lines," *Blood,* 1996, 88(3), 809–816.

Webster, M.K. et al., "Constitutive activation of fibroblast growth factor receptor 3 by the transmembrane point mutation found in achondroplasia," *EMBO J.,* 1996, 15, 520–527.

Xu, Y. et al., "Characterization of epidermal growth factor receptor gene expression in malignant and normal human cell lines," *Proc. Natl. Acad. Sci. USA,* 1984, 81, 7308–7312.

Yamada, K. et al., "Substitution of the insulin receptor transmembrane domain with the c–neu/erbB2 transmembrane domain constitutively activates the insulin receptor kinas in vitro," *J. Biol. Chem.,* 1992, 267(18), 12452–12461.

Zhang, S. et al., "Identification of Dynorphins as Endogenous Ligands for an Opioid Receptor–Like Orphan Receptor," *J. Biol. Chem.,* 1995, 270, 22772–22776.

Zhen, Z. et al., "Structural and functional domains critical for constitutive activation of the HGF–receptor (Met)," *Oncogene,* 1994, 9, 1691–1697.

Gantz, I. et al., "Molecular Cloning of a Novel Melanocortin Receptor," *J. Biol. Chem.,* 1993, 268(11), 8246–8250.

Heiber, M. et al., "Isolation of Three Novel Human Genes Encoding G Protein–Coupled Receptors," *DNA and Cell Biology,* 1995, 14(1), 25–35.

Howard, A.D. et al., "A Receptor in Pituitary and Hypothalamus That Functions in Growth Hormone Release," *Science,* 1996, 273, 974–977.

Iismaa, T.P. et al., "Isolation and Chromosomal Localization of a Novel Human G–Protein–Coupled Receptor (GPR3) Expressed Predominantly in the Central Nervous System," *Genomics,* 1994, 24, 391–394.

Itoh, H. et al., "Molecular cloning and sequence determination of cDNAs for α subunits of the guanine nucleotide–binding proteins $G_s$, $G_i$, and $G_o$ from rat brain," *Proc. Natl. Acad. Sci. USA,* 1986, 83, 3776–3780.

Flegal, et al., Overweight and obesity in the United States: prevalence and trends, 1960–1994, *22 Int. J. Obes. Relat. Metab. Disor.,* 1998, 39–47.

Health Implications of Obesity, NIH Consens. Statement Online, Feb. 11–13, 1985, 5(9), 1–7.

Nishina, P.M. et al., "Atherosclerosis in genetically obese mice: the mutants obese, diabetes, fat, tubby, and lethal yellow," *Metab.,* 1994, 43(5), 554–558.

Paxinos, G. et al., "The Rat Brain," New York, Academic Press, 1982.

* cited by examiner

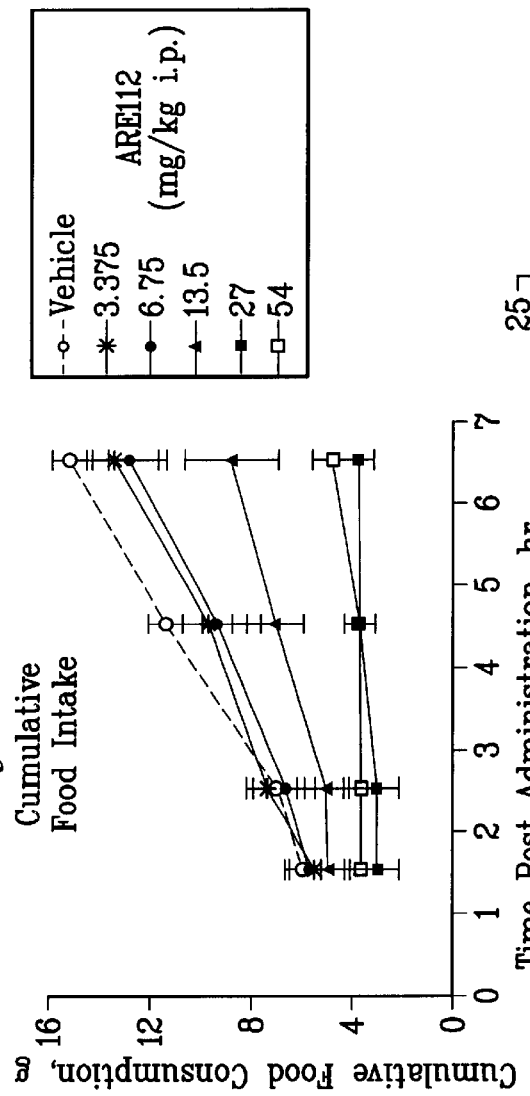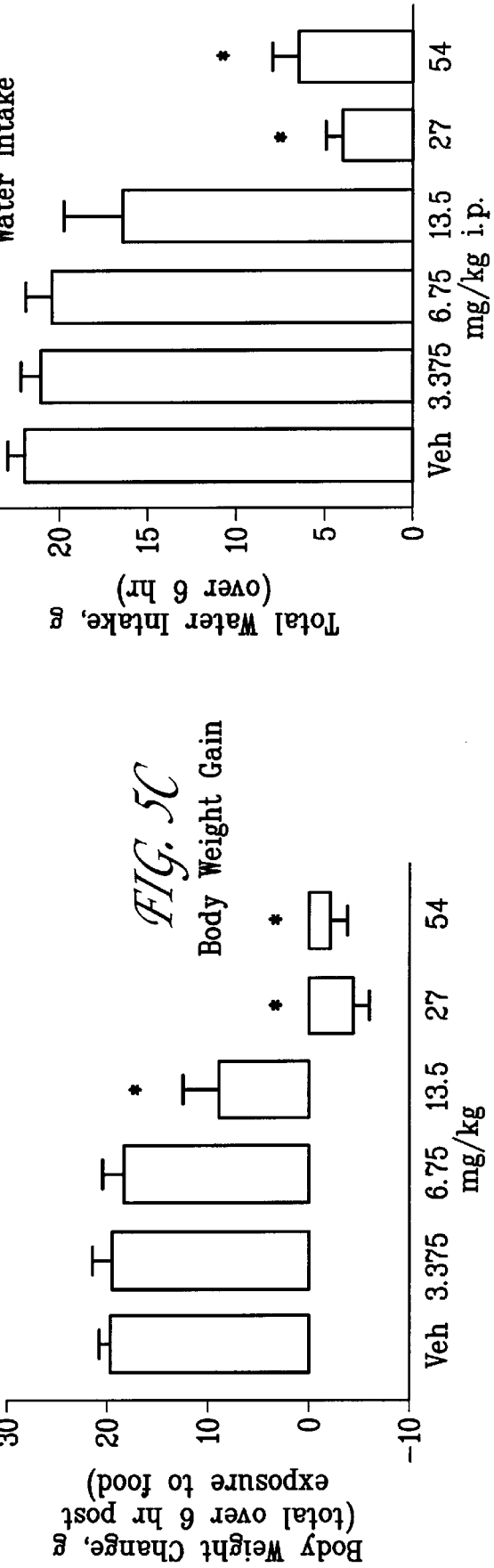
FIG. 5A Cumulative Food Intake
FIG. 5B Water Intake
FIG. 5C Body Weight Gain

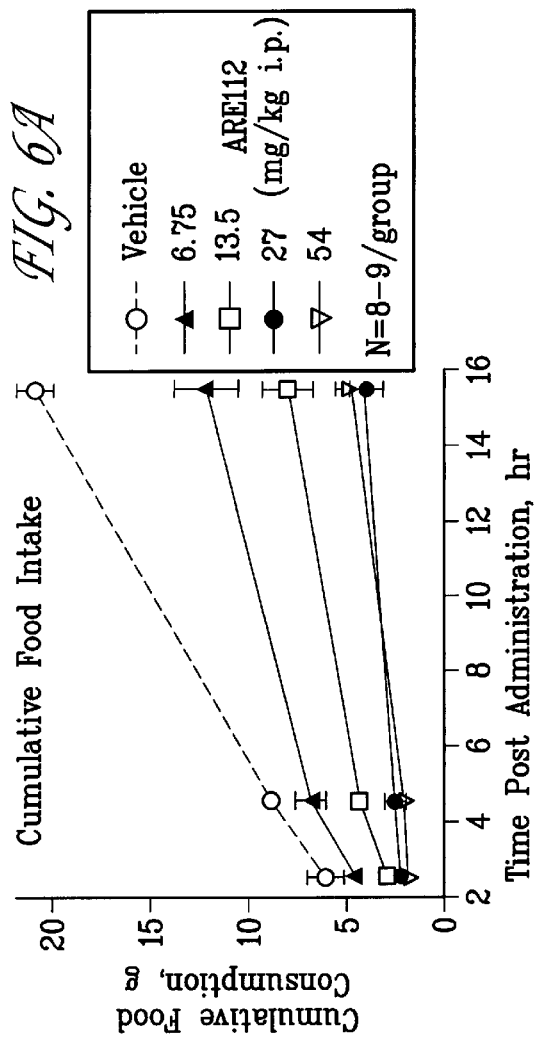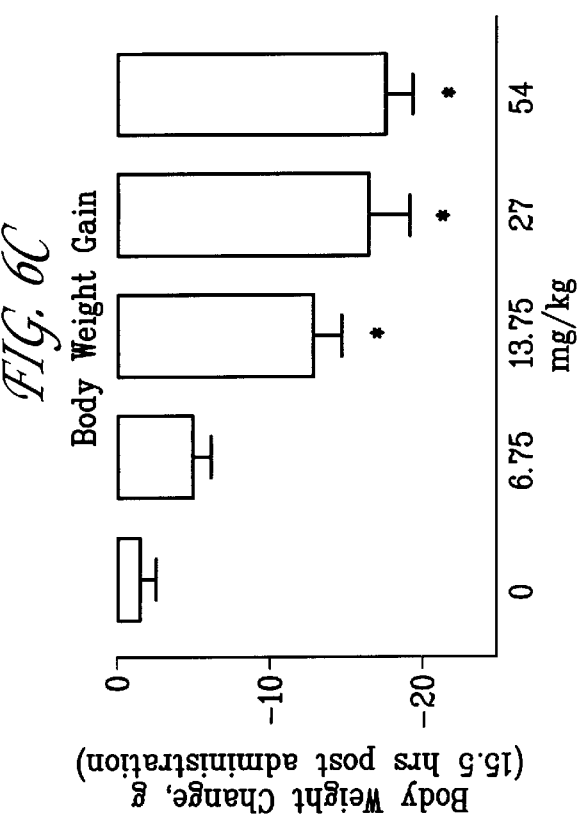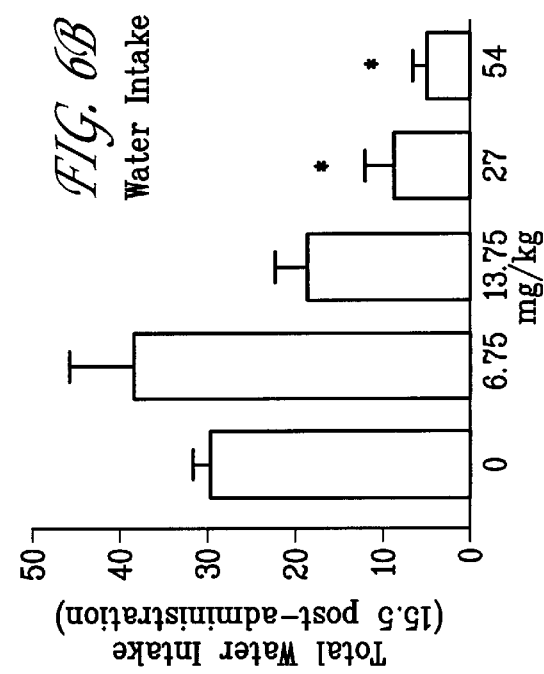

Cumulative Food Intake

Cumulative Food Intake

SEQUENCE LISTING

<160> NUMBER OF SEQ ID NOS: 6

<210> SEQ ID NO 1
<211> LENGTH: 1089
<212> TYPE: DNA
<213> ORGANISM: Homo sapiens

<400> SEQUENCE: 1

```
atgaacgcga gcgccgcctc gctcaacgac tcccaggtgg tggtagtggc ggccgaagga        60
gcggcggcgg cggccacagc agcaggggggg ccggacacgg gcgaatgggg accccctgct       120
gcggcggctc taggagccgg cggcggagct aatgggtctc tggagctgtc ctcgcagctg       180
tcggctgggc caccgggact cctgctgcca gcggtgaatc cgtgggacgt gctcctgtgc       240
gtgtcgggga cagtgatcgc tggagaaaac gcgctggtgg tggcgctcat cgcgtccact       300
ccggcgctgc gcacgcccat gttcgtgctg gtaggcagcc tggccaccgc tgacctgttg       360
gcgggctgtg gcctcatctt gcactttgtg ttccagtact tggtgccctc ggagactgtg       420
agtctgctca cggtgggctt cctcgtggcc tccttcgccg cctctgtcag cagcctgctg       480
gccattacgg tggaccgcta cctgtccctg tataacgcgc tcacctatta ctcgcgccgg       540
accctgttgg gcgtgcacct cctgcttgcc gccacttgga ccgtgtccct aggcctgggg       600
ctgctgcccg tgctgggctg gaactgcctg gcagagcgcg ccgcctgcag cgtggtgcgc       660
ccgctggcgc gcagccacgt ggctctgctc tccgccgcct tcttcatggt cttcggcatc       720
atgctgcacc tgtacgtgcg catctgccag gtggtctggc gccacgcgca ccagatcgcg       780
ctgcagcagc actgcctggc gccacccat ctcgctgcca ccagaaaggg tgtgggtaca       840
ctggctgtgg tgctgggcac tttcggcgcc agctggctgc ccttcgccat ctattgcgtg       900
gtgggcagcc atgaggaccc ggcggtctac acttacgcca ccctgctgcc cgccacctac       960
aactccatga tcaatcccat catctatgcc ttccgcaacc aggagatcca gcgcgccctg      1020
tggctcctgc tctgtggctg tttccagtcc aaagtgccct ttcgttccag gtctcccagc      1080
gaggtctga                                                              1089
```

<210> SEQ ID NO 2
<211> LENGTH: 362
<212> TYPE: PRT
<213> ORGANISM: Homo sapiens

<400> SEQUENCE: 2

```
Met Asn Ala Ser Ala Ala Ser Leu Asn Asp Ser Gln Val Val Val Val
  1               5                  10                  15

Ala Ala Glu Gly Ala Ala Ala Ala Thr Ala Ala Gly Gly Pro Asp
                 20                  25                  30

Thr Gly Glu Trp Gly Pro Pro Ala Ala Ala Ala Leu Gly Ala Gly Gly
                 35                  40                  45
```

```
Gly Ala Asn Gly Ser Leu Glu Leu Ser Ser Gln Leu Ser Ala Gly Pro
         50                  55                  60

Pro Gly Leu Leu Pro Ala Val Asn Pro Trp Asp Val Leu Leu Cys
 65                  70                  75                  80

Val Ser Gly Thr Val Ile Ala Gly Glu Asn Ala Leu Val Val Ala Leu
                 85                  90                  95

Ile Ala Ser Thr Pro Ala Leu Arg Thr Pro Met Phe Val Leu Val Gly
             100                 105                 110

Ser Leu Ala Thr Ala Asp Leu Leu Ala Gly Cys Gly Leu Ile Leu His
             115                 120                 125

Phe Val Phe Gln Tyr Leu Val Pro Ser Glu Thr Val Ser Leu Leu Thr
             130                 135                 140

Val Gly Phe Leu Val Ala Ser Phe Ala Ala Ser Val Ser Ser Leu Leu
145                 150                 155                 160

Ala Ile Thr Val Asp Arg Tyr Leu Ser Leu Tyr Asn Ala Leu Thr Tyr
                 165                 170                 175

Tyr Ser Arg Arg Thr Leu Leu Gly Val His Leu Leu Leu Ala Ala Thr
             180                 185                 190

Trp Thr Val Ser Leu Gly Leu Gly Leu Leu Pro Val Leu Gly Trp Asn
             195                 200                 205

Cys Leu Ala Glu Arg Ala Ala Cys Ser Val Val Arg Pro Leu Ala Arg
210                 215                 220

Ser His Val Ala Leu Leu Ser Ala Ala Phe Phe Met Val Phe Gly Ile
225                 230                 235                 240

Met Leu His Leu Tyr Val Arg Ile Cys Gln Val Val Trp Arg His Ala
                 245                 250                 255

His Gln Ile Ala Leu Gln Gln His Cys Leu Ala Pro Pro His Leu Ala
             260                 265                 270

Ala Thr Arg Lys Gly Val Gly Thr Leu Ala Val Val Leu Gly Thr Phe
             275                 280                 285

Gly Ala Ser Trp Leu Pro Phe Ala Ile Tyr Cys Val Val Gly Ser His
290                 295                 300

Glu Asp Pro Ala Val Tyr Thr Tyr Ala Thr Leu Leu Pro Ala Thr Tyr
305                 310                 315                 320

Asn Ser Met Ile Asn Pro Ile Ile Tyr Ala Phe Arg Asn Gln Glu Ile
                 325                 330                 335

Gln Arg Ala Leu Trp Leu Leu Leu Cys Gly Cys Phe Gln Ser Lys Val
             340                 345                 350

Pro Phe Arg Ser Arg Ser Pro Ser Glu Val
             355                 360

<210> SEQ ID NO 3
<211> LENGTH: 31
<212> TYPE: DNA
<213> ORGANISM: Homo sapiens

<400> SEQUENCE: 3
gatctctaga atgcagggtg caaatccggc c                                    31

<210> SEQ ID NO 4
<211> LENGTH: 35
<212> TYPE: DNA
<213> ORGANISM: Homo sapiens

<400> SEQUENCE: 4
ctagggtacc cggacctcgc tgggagacct ggaac                                35
```

<210> SEQ ID NO 5
<211> LENGTH: 2328
<212> TYPE: DNA
<213> ORGANISM: Homo sapiens

<400> SEQUENCE: 5

```
tctagaatgc agggtgcaaa tccggccgcg atgaacgcga gcgccgcctc gctcaacgac      60
tcccaggtgg tggtagtggc ggccgaagga gcggcggcgg cggccacagc agcaggggggg    120
ccggacacgg gcgaatgggg acccctgct gcggcggctc taggagccgg cggcggagct     180
aatgggtctc tggagctgtc ctcgcagctg tcggctgggc caccgggact cctgctgcca    240
gcggtgaatc cgtgggacgt gctcctgtgc gtgtcgggga cagtgatcgc tggagaaaac    300
gcgctggtgg tggcgctcat cgcgtccact ccggcgctgc gcacgcccat gttcgtgctg    360
gtaggcagcc tggccaccgc tgacctgttg gcgggctgtg gcctcatctt gcactttgtg    420
ttccagtact tggtgccctc ggagactgtg agtctgctca cggtgggctt cctcgtggcc    480
tccttcgccg cctctgtcag cagcctgctg gccattacgg tggaccgcta cctgtccctg    540
tataacgcgc tcacctatta ctcgcgccgg accctgttgg gcgtgcacct cctgcttgcc    600
gccacttgga ccgtgtccct aggcctgggg ctgctgcccg tgctgggctg gaactgcctg    660
gcagagcgcg ccgcctgcag cgtggtgcgc ccgctggcgc gcagccacgt ggctctgctc    720
tccgccgcct tcttcatggt cttcggcatc atgctgcacc tgtacgtgcg catctgccag    780
gtggtctggc gccacgcgca ccagatcgcg ctgcagcagc actgcctggc gccaccccat    840
ctcgctgcca ccagaaaggg tgtgggtaca ctggctgtgg tgctgggcac tttcggcgcc    900
agctggctgc ccttcgccat ctattgcgtg gtgggcagcc atgaggaccc ggcggtctac    960
acttacgcca ccctgctgcc cgccacctac aactccatga tcaatcccat catctatgcc   1020
ttccgcaacc aggagatcca gcgcgccctg tggctcctgc tctgtggctg tttccagtcc   1080
aaagtgccct ttcgttccag gtctcccagc gaggtccggg taccaagctt gggctgcagg   1140
tcgatgggct gcctcggcaa cagtaagacc gaggaccagc gcaacgagga gaaggcgcag   1200
cgcgaggcca acaaaaagat cgagaagcag ctgcagaagg acaagcaggt ctaccgggcc   1260
acgcaccgcc tgctgctgct gggtgctgga gagtctggca aaagcaccat tgtgaagcag   1320
atgaggatcc tacatgttaa tgggtttaac ggagagggcg gcgaagagga cccgcaggct   1380
gcaaggagca acagcgatgg tgagaaggcc accaaagtgc aggacatcaa aaacaacctg   1440
aaggaggcca ttgaaaccat tgtggccgcc atgagcaacc tggtgccccc cgtggagctg   1500
gccaaccctg agaaccagtt cagagtggac tacattctga gcgtgatgaa cgtgccaaac   1560
tttgacttcc cacctgaatt ctatgagcat gccaaggctc tgtgggagga tgagggagtt   1620
cgtgcctgct acgagcgctc caacgagtac cagctgatcg actgtgccca gtacttcctg   1680
gacaagattg atgtgatcaa gcaggccgac tacgtgccaa gtgaccagga cctgcttcgc   1740
tgccgcgtcc tgacctctgg aatctttgag accaagttcc aggtggacaa agtcaacttc   1800
cacatgttcg atgtgggcgg ccagcgcgat gaacgccgca gtggatcca gtgcttcaat   1860
gatgtgactg ccatcatctt cgtggtggcc agcagcagct acaacatggt catccgggag   1920
gacaaccaga ccaaccgtct gcaggaggct ctgaacctct tcaagagcat ctggaacaac   1980
agatggctgc gtaccatctc tgtgatcctc ttcctcaaca gcaagatctg gcttgctgag   2040
aaggtcctcg ctgggaaatc gaagattgag gactactttc cagagttcgc tcgctacacc   2100
```

```
actcctgagg atgcgactcc cgagcccgga gaggacccac gcgtgacccg ggccaagtac    2160
ttcatccggg atgagtttct gagaatcagc actgctagtg gagatggacg tcactactgc   2220
taccctcact ttacctgcgc cgtggacact gagaacatcc gccgtgtctt caacgactgc   2280
cgtgacatca tccagcgcat gcatcttcgc caatacgagc tgctctaa              2328
```

<210> SEQ ID NO 6
<211> LENGTH: 775
<212> TYPE: PRT
<213> ORGANISM: Homo sapiens

<400> SEQUENCE: 6

```
Ser Arg Met Gln Gly Ala Asn Pro Ala Met Asn Ala Ser Ala Ala
 1               5                  10                  15

Ser Leu Asn Asp Ser Gln Val Val Val Ala Ala Glu Gly Ala Ala
                20                  25                  30

Ala Ala Ala Thr Ala Ala Gly Gly Pro Asp Thr Gly Glu Trp Gly Pro
             35                  40                  45

Pro Ala Ala Ala Leu Gly Ala Gly Gly Ala Asn Gly Ser Leu
         50                  55                  60

Glu Leu Ser Ser Gln Leu Ser Ala Gly Pro Pro Gly Leu Leu Leu Pro
 65                  70                  75                  80

Ala Val Asn Pro Trp Asp Val Leu Leu Cys Val Ser Gly Thr Val Ile
                 85                  90                  95

Ala Gly Glu Asn Ala Leu Val Val Ala Leu Ile Ala Ser Thr Pro Ala
                100                 105                 110

Leu Arg Thr Pro Met Phe Val Leu Val Gly Ser Leu Ala Thr Ala Asp
            115                 120                 125

Leu Leu Ala Gly Cys Gly Leu Ile Leu His Phe Val Phe Gln Tyr Leu
130                 135                 140

Val Pro Ser Glu Thr Val Ser Leu Leu Thr Val Gly Phe Leu Val Ala
145                 150                 155                 160

Ser Phe Ala Ala Ser Val Ser Ser Leu Leu Ala Ile Thr Val Asp Arg
                165                 170                 175

Tyr Leu Ser Leu Tyr Asn Ala Leu Thr Tyr Tyr Ser Arg Arg Thr Leu
            180                 185                 190

Leu Gly Val His Leu Leu Leu Ala Ala Thr Trp Thr Val Ser Leu Gly
        195                 200                 205

Leu Gly Leu Leu Pro Val Leu Gly Trp Asn Cys Leu Ala Glu Arg Ala
    210                 215                 220

Ala Cys Ser Val Val Arg Pro Leu Ala Arg Ser His Val Ala Leu Leu
225                 230                 235                 240

Ser Ala Ala Phe Phe Met Val Phe Gly Ile Met Leu His Leu Tyr Val
                245                 250                 255

Arg Ile Cys Gln Val Val Trp Arg His Ala His Gln Ile Ala Leu Gln
            260                 265                 270

Gln His Cys Leu Ala Pro Pro His Leu Ala Ala Thr Arg Lys Gly Val
        275                 280                 285

Gly Thr Leu Ala Val Val Leu Gly Thr Phe Gly Ala Ser Trp Leu Pro
    290                 295                 300

Phe Ala Ile Tyr Cys Val Val Gly Ser His Glu Asp Pro Ala Val Tyr
305                 310                 315                 320

Thr Tyr Ala Thr Leu Leu Pro Ala Thr Tyr Asn Ser Met Ile Asn Pro
                325                 330                 335
```

-continued

```
Ile Ile Tyr Ala Phe Arg Asn Gln Glu Ile Gln Arg Ala Leu Trp Leu
            340                 345                 350

Leu Leu Cys Gly Cys Phe Gln Ser Lys Val Pro Phe Arg Ser Arg Ser
            355                 360                 365

Pro Ser Glu Val Arg Val Pro Ser Leu Gly Cys Arg Ser Met Gly Cys
    370                 375                 380

Leu Gly Asn Ser Lys Thr Glu Asp Gln Arg Asn Glu Glu Lys Ala Gln
385                 390                 395                 400

Arg Glu Ala Asn Lys Lys Ile Glu Lys Gln Leu Gln Lys Asp Lys Gln
                405                 410                 415

Val Tyr Arg Ala Thr His Arg Leu Leu Leu Gly Ala Gly Glu Ser
            420                 425                 430

Gly Lys Ser Thr Ile Val Lys Gln Met Arg Ile Leu His Val Asn Gly
            435                 440                 445

Phe Asn Gly Glu Gly Gly Glu Glu Asp Pro Gln Ala Ala Arg Ser Asn
            450                 455                 460

Ser Asp Gly Glu Lys Ala Thr Lys Val Gln Asp Ile Lys Asn Asn Leu
465                 470                 475                 480

Lys Glu Ala Ile Glu Thr Ile Val Ala Ala Met Ser Asn Leu Val Pro
                485                 490                 495

Pro Val Glu Leu Ala Asn Pro Glu Asn Gln Phe Arg Val Asp Tyr Ile
            500                 505                 510

Leu Ser Val Met Asn Val Pro Asn Phe Asp Phe Pro Pro Glu Phe Tyr
            515                 520                 525

Glu His Ala Lys Ala Leu Trp Glu Asp Glu Gly Val Arg Ala Cys Tyr
            530                 535                 540

Glu Arg Ser Asn Glu Tyr Gln Leu Ile Asp Cys Ala Gln Tyr Phe Leu
545                 550                 555                 560

Asp Lys Ile Asp Val Ile Lys Gln Ala Asp Tyr Val Pro Ser Asp Gln
                565                 570                 575

Asp Leu Leu Arg Cys Arg Val Leu Thr Ser Gly Ile Phe Glu Thr Lys
            580                 585                 590

Phe Gln Val Asp Lys Val Asn Phe His Met Phe Asp Val Gly Gly Gln
            595                 600                 605

Arg Asp Glu Arg Arg Lys Trp Ile Gln Cys Phe Asn Asp Val Thr Ala
    610                 615                 620

Ile Ile Phe Val Val Ala Ser Ser Ser Tyr Asn Met Val Ile Arg Glu
625                 630                 635                 640

Asp Asn Gln Thr Asn Arg Leu Gln Glu Ala Leu Asn Leu Phe Lys Ser
                645                 650                 655

Ile Trp Asn Asn Arg Trp Leu Arg Thr Ile Ser Val Ile Leu Phe Leu
            660                 665                 670

Asn Lys Gln Asp Leu Leu Ala Glu Lys Val Leu Ala Gly Lys Ser Lys
            675                 680                 685

Ile Glu Asp Tyr Phe Pro Glu Phe Ala Arg Tyr Thr Thr Pro Glu Asp
            690                 695                 700

Ala Thr Pro Glu Pro Gly Glu Asp Pro Arg Val Thr Arg Ala Lys Tyr
705                 710                 715                 720
```

```
Phe Ile Arg Asp Glu Phe Leu Arg Ile Ser Thr Ala Ser Gly Asp Gly
            725                 730                 735
Arg His Tyr Cys Tyr Pro His Phe Thr Cys Ala Val Asp Thr Glu Asn
            740                 745                 750
Ile Arg Arg Val Phe Asn Asp Cys Arg Asp Ile Ile Gln Arg Met His
            755                 760                 765
Leu Arg Gln Tyr Glu Leu Leu
            770             775
```

SMALL MOLECULE MODULATORS OF G PROTEIN-COUPLED RECEPTOR SIX

RELATED CASES

This patent document is related to U.S. patent application Ser. No. 09/364,425 filed via Express Mail on Jul. 30, 1999 claiming the benefit of commonly owned: (1) Provisional Patent Application Ser. No. 60/094,879, filed Jul. 31, 1998; (2) Provisional Patent Application Ser. No. 60/106,300, filed Oct. 30, 1998; (3) Provisional Patent Application Ser. No. 60/110,906, filed Dec. 4, 1998; (4) Provisional Patent Application Ser. No. 60/121,851, filed Feb. 26, 1999 (5) Provisional Patent Application Ser. No. 60/173,850, filed Dec. 30, 1999; and (6) Provisional Patent Application Ser. No. 60/174,428, filed Jan. 4, 2000. The disclosure of each of the foregoing patent documents is incorporated in its entirety herein by reference. Priority benefit of aforementioned U.S. application Ser. No. 09/364,425 and Provisional Patent Applications (4), (5) and (6) above is hereby claimed.

FIELD OF INVENTION

The present invention relates to small molecule modulators of G protein-coupled receptor six (GPR6); preferably, the small molecule modulators are preferentially selected for the human GPR6; most preferably, the small molecule modulators are inverse agonists to the human GPR6.

BACKGROUND OF THE INVENTION

A. G Protein-Coupled Receptors

G protein-coupled receptors (GPCR) share a common structural motif. All these receptors have seven sequences of between 22 to 24 hydrophobic amino acids that form seven alpha helices, each of which spans the membrane. The transmembrane helices are joined by strands of amino acids having a larger loop between the fourth and fifth transmembrane helix on the extracellular side of the membrane. Another larger loop, composed primarily of hydrophilic amino acids, joins transmembrane helices five and six on the intracellular side of the membrane. The carboxy terminus of the receptor lies intracellularly with the amino terminus in the extracellular space. It is thought that the loop joining helices five and six, as well as the carboxy terminus, interact with the G protein. Currently, Gq, Gs, Gi, and Go are G proteins that have been identified.

Under physiological conditions, GPCRs exist in the cell membrane in equilibrium between two different states or conformations: an "inactive" state and an "active" state. A receptor in an inactive state is unable to link to the intracellular transduction pathway to produce a biological response. Changing the receptor conformation to the active state allows linkage to the transduction pathway and produces a biological response.

A receptor may be stabilized in an active state by an endogenous ligand or an exogenous agonist ligand. Recent discoveries, including but not exclusively limited to, modifications to the amino acid sequence of the receptor, provide alternative mechanisms other than ligands to stabilize the active state conformation. These approaches effectively stabilize the receptor in an active state by simulating the effect of a ligand binding to the receptor. Stabilization by such ligand-independent approaches is termed "constitutive receptor activation." A receptor for which the endogenous ligand is unknown or not identified is referred to as an "orphan receptor."

B. Traditional Compound Screening

Generally, the use of an orphan receptor for screening purposes to identify compounds that modulate a biological response associated with such receptor has not been possible. This is because the traditional "dogma" regarding screening of compounds mandates that the ligand for the receptor be known, whereby compounds that competitively bind with the receptor, i.e., by interfering or blocking the binding of the natural ligand with the receptor, are selected. By definition, then, this approach has no applicability with respect to orphan receptors. Thus, by adhering to this dogmatic approach to the discovery of therapeutics, the art, in essence, has taught and has been taught to forsake the use of orphan receptors unless and until the natural ligand for the receptor is discovered. The pursuit of an endogenous ligand for an orphan receptor can take several years and cost millions of dollars.

Furthermore, and given that there are an estimated 2,000 GPCRs in the human genome, the majority of which being orphan receptors, the traditional dogma castigates a creative approach to the discovery of therapeutics to these receptors.

Numerous orphan G protein-coupled receptors are constitutively active in their endogenous state. GPR6 is a 362 amino acid homolog of GPR3; the endogenous ligand for GPR6 is unknown (Song, Z.-H. et al, supra.; see FIG. 1 for reported amino acid sequence). GPR6 transcripts are reported to be abundant in the human putamen and to a lesser extent in the frontal cortex, hippocampus, and hypothalamus (Heiber, M. et al. *DNA and Cell Biology* (1995) 14(1): 25; see FIG. 1 for reported nucleic acid and amino acid sequences for GPR6).

C. Obesity

Recently, our current knowledge of human obesity has advanced dramatically. Previously, obesity was viewed as an oppugnant behavior of inappropriate eating in the setting of appealing foods. Studies of animal models of obesity, biochemical alterations in both humans and animals, and the complex interactions of psychosocial and cultural factors that create receptiveness to human obesity indicate that this disease in humans is multifaceted and deeply entrenched in biologic systems. Thus, it is almost certain that obesity has multiple causes and that there are different types of obesity.

An increasing number of children and adolescents are overweight. Although not all overweight children will necessarily become overweight adults, the growing occurrence of obesity in childhood is likely to be reflected in increasing obesity in adult years. The high prevalence of obesity in our adult population and the likelihood that the nation of the future will be even more obese demands a re-examination of the health implications of this disease. See, Health Implications of Obesity. NIH Consens. Statement Online 1985 February 11–13; 5(9):1–7.

"Clinical obesity" is a measurement of the excess body fat relative to lean body mass and is defined as a body weight more than 20% above the ideal body weight. Recent estimates suggest that 1 in 2 adults in the United States is clinically obese, an increase of more than 25% over the past decades. Flegal M D., et al., 22 Int. *J. Obes. Relat. Metab. Disor.* 39 (1998). Both overweight conditions and clinical obesity are a major health concerns worldwide, in particular because clinical obesity is often accompanied by numerous complications, i.e., hypertension and Type II diabetes, which in turn can cause coronary artery disease, stroke, late-stage complications of diabetes and premature death. (See, e.g., Nishina P. M. et al., 43 *Metab.* 554 (1994)).

Although the etiologic mechanisms underlying obesity require further clarification, the net effect of such mechanisms leads to an imbalance between energy intake and expenditure. Both genetic and environmental factors are likely to be involved in the pathogenesis of obesity. These include excess caloric intake, decreased physical activity, and metabolic and endocrine abnormalities.

Treatment of overweight conditions and clinical obesity via pharmaceutical agents are not only of importance with respect to the conditions themselves, but also with respect to the possibility of preventing other diseases that are associated with, e.g., clinical obesity, as well as enhancement of the positive feeling of "self" that often accompanies those who are overweight or clinically obese and who encounter a significant reduction in body weight.

Given the foregoing discussion, it is apparent that compounds which help in the treatment of such disorders would be useful and would provide an advance in both research and clinical medicine. The present invention is directed to these, as well as other, important ends.

SUMMARY OF THE INVENTION

The present invention relates to small molecule modulators of the GPR6 receptor. Most preferably, the GPR6 modulators have inverse agonist characteristics at the receptor.

BRIEF DESCRIPTION OF THE DRAWINGS

FIGS. 5A, 5B and 5C provide graphic representations of the results of in vivo administration (IP) of ARE112 on cumulative food intake (5A), water intake (5B) and body weight gain (5C) on 24-hour food deprived rats.

FIGS. 6A, 6B and 6C provide graphic representations of the results of in vivo administration (IP) of ARE112 on cumulative food intake (6A), water intake (6B) and body weight gain (6C) on non food deprived rats.

DEFINITIONS

Figure 1:
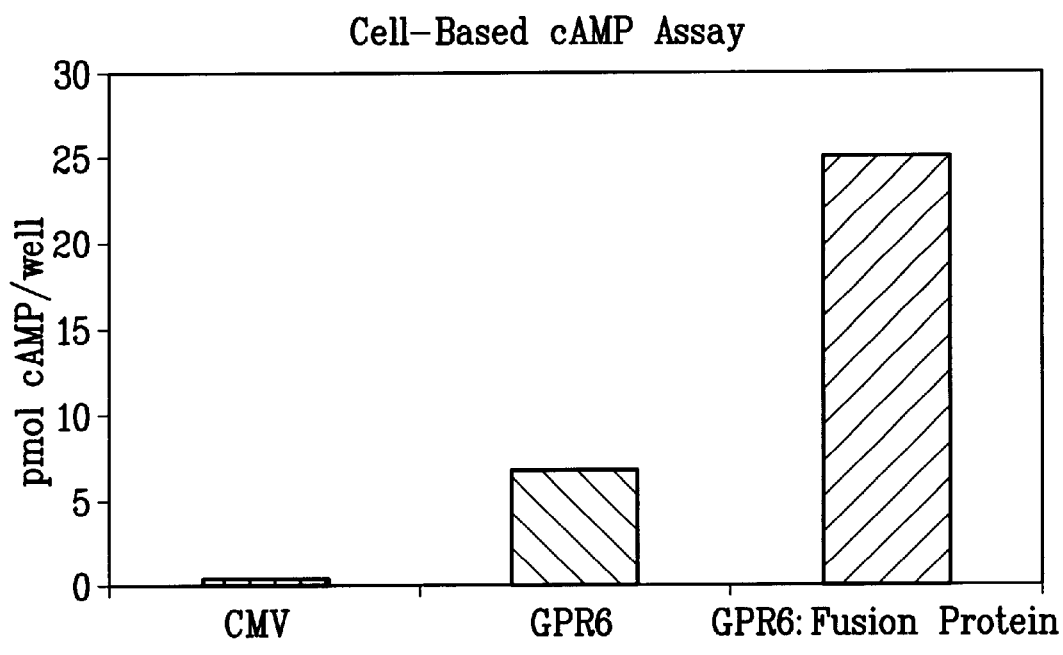
FIG. 1 is a graphic representation of the results of a cell-based cyclic AMP assay providing comparative results for constitutive signaling GPR6 and GPR6:Fusion Protein.

The scientific literature that has evolved around receptors has adopted a number of terms. For clarity and consistency, the following definitions will be used throughout this patent document. To the extent that these definitions conflict with other definitions for these terms, the following definitions shall control.

ACTIVE INGREDIENT in the context of a "Pharmaceutical Composition" shall mean a component of a Pharmaceutical Composition that provides the primary pharmaceutical benefit, as opposed to an "inactive ingredient" which would generally be recognized as providing no pharmaceutical benefit.

AGONISTS shall mean moieties that activate the intracellular response when they bind to the receptor, or enhance GTP binding to membranes. In the context of the disclosed invention, a Pharmaceutical Candidate comprising a GPR6 Agonist can be utilized for increasing body weight and/or affecting metabolism such that the recipient gains weight and/or maintains weight. Such can be used in the context of disorders and/or diseases where weight loss is a component of the disease and/or disorder such as, for example, anorexia nervosa, cancer, AIDS cachexia, etc.

PARTIAL AGONISTS shall mean moieties that activate the intracellular response when they bind to the receptor to a lesser degree/extent than do agonists, or enhance GTP binding to membranes to a lesser degree/extent than do agonists.

ANTAGONIST shall mean moieties that competitively bind to the receptor at the same site as the agonists but which do not activate the intracellular response initiated by the active form of the receptor, and can thereby inhibit the intracellular responses by agonists or partial agonists. ANTAGONISTS do not diminish the baseline intracellular response in the absence of an agonist or partial agonist.

CANDIDATE COMPOUND, in the context of the disclosed invention, shall mean a small molecule that is amenable to a screening technique.

COMPOSITION shall mean a material comprising at least two compounds or two components; for example, and not limitation, a Pharmaceutical Composition comprising at least one Active Ingredient and at least one other component is a Composition.

COMPOUND EFFICACY shall mean a measurement of the ability of a compound to inhibit or stimulate receptor functionality, as opposed to receptor binding affinity.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing at least two moieties together, whether in an in vitro system or an in vivo system.

ENDOGENOUS shall mean a material that a mammal naturally produces. ENDOGENOUS in reference to, for example and not limitation, the term "receptor" shall mean that which is naturally produced by a mammal (for example, and not limitation, a human) or a virus. In contrast, the term NON-ENDOGENOUS in this context shall mean that which is not naturally produced by a mammal (for example, and not limitation, a human) or a virus. For example, and not limitation, a receiver which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

G PROTEIN COUPLED RECEPTOR FUSION PROTEIN and GPCR FUSION PROTEIN, in the context of the invention disclosed herein, each mean a non-endogenous protein comprising an endogenous, constitutively activated orphan GPCR fused to at least one G protein, most preferably, the alpha (α) subunit of such G protein (this being the subunit that binds GTP), with the G protein preferably being of the same type as the G protein that naturally couples with endogenous orphan GPCR. For example, and not limitation, in an endogenous state, the G protein "Gsα" is the predominate G protein that couples with GPR6 such that a GPCR Fusion Protein based upon GPR6 would be a non-endogenous protein comprising GPR6 fused to Gsα. The G protein can be fused directly to the c-terminus of the endogenous, constitutively active orphan GPCR or there may be spacers between the two.

INHIBIT or INHIBITING, in relationship to the term "response" shall mean that a response is decreased or prevented in the presence of a compound as opposed to in the absence of the compound.

INVERSE AGONISTS shall mean moieties that bind the endogenous form of the receptor, and which inhibit the baseline intracellular response initiated by the active endogenous form of the receptor below the normal base level of activity that is observed in the absence of the endogenous ligand, agonists or partial agonists, or decrease GTP binding to membranes. Preferably, the baseline intracellular response is decreased in the presence of the inverse agonist by at least 30%, more preferably by at least 50%, and most preferably by at least 75%, as compared with the baseline response in the absence of the inverse agonist. Biologically, "GPR6 inverse agonist" shall mean moieties that can be assessed in vivo by factors other than just determination that the moiety has interacted with GPR6, e.g., when the moiety interacts with a mammal's GPR6 in vivo, there is an observed decrease in the mammal's body weight by at least about 5% within 24 to 48 hours of contacting GPR6 and the GPR6 inverse agonist.

LIGAND shall mean an endogenous, naturally occurring molecule specific for an endogenous, naturally occurring receptor.

PHARMACEUTICAL COMPOSITION shall mean a composition comprising at one Active Ingredient and at least one ingredient that is not an Active Ingredient (for example and not limitation, a filler, dye, or a mechanism for slow release), whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

SMALL MOLECULE, in the context of the invention disclosed herein, is a non-protein based moiety; for example, and not limitation, ARE112 is a small molecule within the context of this invention, while the endogenous ligand for a receptor is not a small molecule.

DETAILED DESCRIPTION

A. Introduction

The traditional study of receptors has always proceeded from the a priori assumption (historically based) that the endogenous ligand must first be identified before discovery could proceed to find antagonists and other molecules that could affect the receptor. Even in cases where an antagonist might have been known first, the search immediately extended to looking for the endogenous ligand. This mode of thinking has persisted in receptor research even after the discovery of constitutively activated receptors. What has not been recognized is that it is the active state of the receptor that is most useful for discovering agonists, partial agonists, and inverse agonists of the receptor. For those diseases that result from an overly active receptor, what is desired in a therapeutic drug is a compound which acts to diminish the active state of a receptor, not necessarily a drug which is an antagonist to the endogenous ligand. This is because a compound (e.g., therapeutic) that reduces the activity of the active receptor state need not bind at the same site as the endogenous ligand. Thus, as taught by a method of this invention, any search for therapeutic compounds should start by screening compounds against the ligand-independent active state. The search, then, is for an inverse agonist to the active state receptor.

Screening candidate compounds against orphan receptors, for example, including and not limited to, GPR6 and GPR6 Fusion Protein, allows for the direct identification of candidate compounds which act at this orphan cell surface receptor, without requiring any prior knowledge or use of the receptor's endogenous ligand. By determining areas within the body where such receptors are expressed and/or over-expressed, it is possible to determine related disease/disorder states which are associated with the expression and/or over-expression of these receptors; such an approach is disclosed in this patent document.

B. Disease/Disorder Identification and/or Selection

As will be set forth in greater detail below, most preferably inverse agonists and agonists to GPR6 can be identified by the methodologies of this invention. Such inverse agonists and agonists are ideal candidates as lead compounds in drug discovery programs for treating diseases related to this receptor. Indeed, an antagonist to such a receptor (even if the ligand were known) may be ineffective given that the receptor is activated even in the absence of ligand-receptor binding. Because of the ability to directly identify inverse agonists and agonists to these receptors, thereby allowing for the development of pharmaceutical compositions, a search for diseases and disorders associated with these receptors is possible. For example, GPR6 is expressed in the following areas of the brain: lateral hypothalamus, hippocampus, nucleus accumbens, caudate and cerebral cortex. Given the high levels of expression in the areas of the brain associated with feeding behavior and metabolism, GPR6 is likely to be related to a variety of disorders and diseases related to abnormal food intake and/or metabolism, e.g., clinical obesity.

C. Screening of Candidate Compounds

1. Generic GPCR screening assay techniques

When a G protein receptor becomes constitutively active, it binds to a G protein (for example Gq, Gs, Gi, Go) and stimulates the binding of GTP to the G protein. The G protein then acts as a GTPase and slowly hydrolyzes the GTP to GDP, whereby the receptor, under normal conditions, becomes deactivated. However, constitutively activated receptors continue to exchange GDP to GTP. A non-hydrolyzable analog of GTP, [$^{35}$S]GTPγS, can be used to monitor enhanced binding to membranes which express constitutively activated receptors. It is reported that [$^{35}$S] GTPγS can be used to monitor G protein coupling to membranes in the absence and presence of ligand. An example of this monitoring, among other examples well-known and available to those in the art, was reported by Traynor and Nahorski in 1995. Generally, this preferred use of this assay system is for initial screening of candidate compounds because the system is generically applicable to all G protein-coupled receptors regardless of the particular G protein that interacts with the intracellular domain of the receptor.

2. Specific GPCR screening assay techniques

Once candidate compounds are identified using the "generic" G protein-coupled receptor assay (i.e. an assay to select compounds that are agonists, partial agonists, or inverse agonists), further screening to confirm that the compounds have interacted at the receptor site is preferred. For example, a compound identified by the "generic" assay may not bind to the receptor, but may instead merely "uncouple" the G protein from the intracellular domain. Thus, by screening those candidate compounds, which have been identified using a "generic" assay in an agonist and/or antagonist competitive binding assay, further refinement in the selection process is provided.

In the case of GPR6 it has been determined that this receptor couples the G protein Gs. Gs stimulates the enzyme adenylyl cyclase (Gi, on the other hand, inhibits this enzyme). Adenylyl cyclase catalyzes the conversion of ATP to cAMP; thus, assays that detect cAMP can be utilized, for example and not limitation, cell-based cAMP assay, to determine if a candidate compound is an inverse agonist to the receptor (i.e., such a compound which contacts the receptor would decrease the levels of cAMP relative to the uncontacted receptor). As a result, "cyclase-based assays" can be used to further screen those compounds selected from an agonist and/or antagonist competitive binding assay.

3. GPCR Fusion Protein

The use of an endogenous, constitutively activated orphan GPCRs, such as GPR6, for use in screening of candidate compounds for the direct identification of inverse agonists, agonists and partial agonists, provides a unique challenge in that, by definition, the endogenous receptor is active even in the absence of an endogenous ligand bound thereto. Thus, in order to differentiate between, e.g., the endogenous receptor in the presence of a candidate compound and the endogenous receptor in the absence of that compound, with an aim of such a differentiation to allow for an understanding as to whether such compound may be an inverse agonist, agonist, partial agonist or have no affect on such a receptor, it is preferred that an approach be utilized that can enhance such differentiation. A preferred approach is the use of a GPCR Fusion Protein.

Generally, once it is determined that an endogenous orphan GPCR is constitutively activate, using the assay techniques set forth above (as well as others), it is possible to determine the predominant G protein that couples with the endogenous GPCR. Coupling of the G protein to the GPCR provides a signaling pathway that can be assessed. Because it is most preferred that screening take place by use of a mammalian expression system, such a system will be expected to have endogenous G protein therein. Thus, by definition, in such a system, the endogenous, constitutively active orphan GPCR will continuously signal. In this regard, it is preferred that this signal be enhanced such that in the presence of, e.g., an inverse agonist to the receptor, it is more likely that one will be able to more readily differentiate, particularly in the context of screening, between the receptor when it is contacted with the inverse agonist.

The GPCR Fusion Protein is intended to enhance the efficacy of G protein coupling with the endogenous GPCR. The GPCR Fusion Protein appears to be important for screening with an endogenous, constitutively activated GPCR because such an approach increases the signal that is most preferably utilized in such screening techniques. This is important in facilitating a significant "signal to noise" ratio. A significant ratio is preferred for the screening of candidate compounds as disclosed herein.

The construction of a construct useful for expression of a GPCR Fusion Protein is within the purview of those having ordinary skill in the art. Commercially available expression vectors and systems offer a variety of approaches that can fit the particular needs of an investigator. The criteria of importance for such a GPCR Fusion Protein construct is that the endogenous GPCR sequence and the G protein sequence both be in-frame (preferably, the sequence for the endogenous GPCR is upstream of the G protein sequence) to and that the "stop" codon of the GPCR must be deleted or replaced such that upon expression of the GPCR, the G protein can also be expressed. The GPCR can be linked directly to the G protein, or there can be spacer residues between the two (preferably, no more than about 12, although this number can be readily ascertained by one of ordinary skill in the art). Both approaches have been evaluated, and in terms of measurement of the activity of the GPCR, the results are substantially the same; however, there is a preference (based upon convenience) for use of a spacer in that some restriction sites that are not used will, upon expression, effectively, become a spacer. Most preferably, the G protein that couples to the endogenous GPCR will have been identified prior to the creation of the GPCR Fusion Protein construct. Because there are only a few G proteins that have been identified, it is preferred that a construct comprising the sequence of the G protein (i.e., a universal G protein construct) be available for insertion of an endogenous GPCR sequence therein; this provides for efficiency in the context of large-scale screening of a variety of different endogenous GPCRs having different sequences.

D. Pharmaceutical Compositions

Candidate compounds selected for further development as active ingredients can be formulated into pharmaceutical compositions using techniques well known to those in the art. Suitable pharmaceutically-acceptable carriers are available to those in the art; for example, see Remington's Pharmaceutical Sciences, 16$^{th}$ Edition, 1980, Mack Publishing Co., (Oslo et al., eds.).

EXAMPLES

The following examples are presented for purposes of elucidation, and not limitation, of the present invention. The particular order of screening techniques set forth below is ranked for presentational efficiency. While specific nucleic acid and amino acid sequences are disclosed herein, those of ordinary skill in the art are credited with the ability to make modifications to these sequences while achieving the same or substantially similar results reported below.

Example 1

Receptor Expression 1. cDNA and Vectors

The expression vector comprising GPR6 cDNA was generously supplied by Brian O'Dowd (University of Toronto). The vector utilized for GPR6 was pRcCMV (the coding region for GPR6 was subcloned into pCMV vector at a HindIII-Xba1 site). See, SEQ.ID.NO.:1 for nucleic acid sequence and SEQ.ID.NO.:2 for the deduced amino acid sequence of GPR6.

2. Transfection Procedure

On day one, $1 \times 10^7$ 293 cells per 150 mm plate were plated out. On day two, two reaction tubes were prepared (the proportions to follow for each tube are per plate): tube A was prepared by mixing 20 μg DNA (e.g., pCMV vector; pCMV vector GPR6 cDNA, pCMV vector GPR6:Fusion-Protein) in 1.2 ml serum free DMEM (Irvine Scientific, Irvine, Calif.); tube B was prepared by mixing 120 μl lipofectamine (Gibco BRL) in 1.2 ml serum free DMEM. Tubes A and B were then admixed by inversions (several times), followed by incubation at room temperature for 30–45 min. The admixture is referred to as the "transfection mixture". Plated 293 cells were washed with 1×PBS, followed by addition of 10 ml serum free DMEM. 2.4 ml of the transfection mixture was then added to the cells, followed by incubation for 4 hrs at 37° C./5% $CO_2$. The transfection mixture was then removed by aspiration, followed by the addition of 25 ml of DMEM/10% Fetal Bovine Serum. Cells were then incubated at 37° C./5% $CO_2$. After 72 hr incubation, cells were then harvested and utilized for analysis.

Example 2

GPCR Fusion Protein Preparation

The design of a GPC6-Fusion Protein construct was accomplished as follows: both the 5' and 3' ends of the rat G protein Gsα (long form; Itoh, H. et al., 83 PNAS 3776 (1986)) were engineered to include a HindIII (5'-AAGCTT-3') sequence thereon. Following confirmation of the correct sequence (including the flanking HindIII sequences), the entire sequence was shuttled into pCDNA3.1(−) (Invitrogen, cat. no. V795-20) by subcloning using the HindIII restriction site of that vector. The correct orientation for the Gsα sequence was determined after subcloning into pCDNA3.1 (−). The modified pcDNA3.1(−) containing the rat Gsα gene at HindIII sequence was then verified; this vector was now available as a "universal" Gsα protein vector. The pcDNA3.1(−) vector contains a variety of well-known restriction sites upstream of the HindIII site, thus beneficially providing the ability to insert, upstream of the Gs protein, the coding sequence of an endogenous, constitutively active GPCR. This same approach can be utilized to create other "universal" G protein vectors, and, of course, other commercially available or proprietary vectors known to the artisan can be utilized—the important criteria is that the sequence for the GPCR be upstream and in-frame with that of the G protein.

GPR6-Gsα Fusion Protein construct was made as follows: primers utilized were as follows:
5'-gatcTCTAGAATGCAGGGTGCAAATCCGGCC-3' (SEQ. ID. NO. 3, sense)
5'-ctagGGTACCCGGACCTCGCTGGGAGACCTGGAAC-3' (SEQ.ID.NO. 4, antisense).
The sense and anti-sense primers also contained restriction sites for XbaI and KpnI, respectively. These restriction sites are available upstream of the HindIII site in the pcDNA3.1 (−) vector.

PCR was then utilized to secure the respective receptor sequences for fusion within the Gsα universal vector disclosed above, using the following protocol for each: 100 ng cDNA for GPR6 was added to separate tubes containing 2 ul of each primer (sense and anti-sense), 3 uL of 10 mM dNTPs, 10 uL of 10×TaqPlus™ Precision buffer, 1 uL of TaqPlus™ Precision polymerase (Stratagene: #600211), and 80 uL of water. Reaction temperatures and cycle times were as follows: the initial denaturing step was done at 96° C. for seven minutes, and a cycle of 96° C. for 30 seconds, 55° C. for 30 seconds, and 72° C. for two minutes was repeated 30 times. A final extension time of ten minutes at 72° C. was done for GPR6. PCR products for GPR6 were run on a 1% agarose gel and then purified (data not shown). The purified product was digested with XbaI and KpnI (New England Biolabs) and the desired inserts were isolated, purified and ligated into the Gs universal vector at the respective restriction site. The positive clones were isolated following transformation and determined by restriction enzyme digest; expression using 293 cells was accomplished following the protocol set forth infra. The positive clone for GPR6:Gsα-Fusion Protein was sequenced and made available for the direct identification of candidate compounds. See, SEQ.ID.NO.:5 for nucleic acid sequence and SEQ.ID.NO.:6 for deduced amino acid sequence of GPR6:Gsα-Fusion Protein.

Example 3A

Asssesment of Constitutive Activity Using Adenylyl Cyclase Assay

A Flash Plate™ Adenylyl Cyclase kit (New England Nuclear; Cat. No. SMP004A) designed for cell-based assays can be modified for use with crude plasma membranes. The Flash Plate wells can contain a scintillant coating that also contains a specific antibody recognizing cAMP. The cAMP generated in the wells can be quantitated by a direct competition for binding of radioactive cAMP tracer to the cAMP antibody. The following serves as a protocol for the measurement of changes in cAMP levels in whole cells that express receptors, e.g. GPR6 or GPR6:Gsα-Fusion Protein.

Transfected cells are harvested approximately twenty-four hours after transient transfection. Media was carefully aspirated off and discarded. 10 ml of PBS was gently added to each dish of cells followed by careful aspiration. 1 ml of Sigma cell dissociation buffer and 3 ml of PBS were added to each plate. Cells were pipeted off the plate and the cell suspension is collected into a 50 ml conical centrifuge tube. Cells were then centrifuged at room temperature at 1,100 rpm for 5 min. The cell pellet was carefully re-suspended into an appropriate volume of PBS (about 3 ml/plate). The cells were then counted using a hemocytometer and additional PBS is added to give the appropriate number of cells (with a final concentration of about $50 \times 10^4$/well).

cAMP standards and Detection Buffer (comprising 1 μCi of tracer [$^{125}$I cAMP (50 μl] to 11 ml Detection Buffer) was prepared and maintained in accordance with the manufacturer's instructions. Stimulation Buffer (preferably prepared fresh) for screening and contained 50 ul of Stimulation Buffer, 3 ul of test compound (12 uM final assay concentration) and 50 ul cells, Stimulation Buffer can be stored on ice until utilized. The assay can be initiated by addition of 50 ul of cAMP standards to appropriate wells followed by addition of 50 ul of PBSA to wells H-11 and H12. 50 ul of Stimulation Buffer was added to all wells. DMSO (or selected candidate compounds) were added to appropriate wells using a pin tool capable of dispensing 3 ul of compound solution, with a final assay concentration of 12 uM test compound and 100 ul total assay volume. The cells were then added to the wells and incubated for 60 min at room temperature. 100 ul of Detection Buffer containing tracer cAMP was then added to all the wells. Plates were then incubated an additional 2 hours followed by counting in a Wallac MicroBeta scintillation counter. Values of cAMP/well were then extrapolated from a standard cAMP curve that is contained within each assay plate.

GPR6 and GPR6:Gsα-Fusion-Protein were analyzed as above and verified to be constitutively active, whereby GPR6:Fusion-Protein evidenced about a 4-fold increase in cAMP over GPR6 (see, FIG. 1). In the context of screening of candidate compounds, when the goal is to identify inverse agonists, agonists or partial agonists, it is preferred that the signal to noise ratio be maximized (especially in the case of screening for inverse agonists). Thus, although it is viable to use GPR6 itself, given the substantial increase in this ratio, the use of the GPR6:Gsα-Fusion Protein is particularly preferred (although one of ordinary skill in the art is credited with selecting an approach that is based upon the particular needs of the artisan). It is further noted that there does not appear to be an "upper-limit" or "ceiling" for the signal such that despite the increase in signal evidenced in FIG. 1, these constructs can also be used for screening to determine agonists of GPR6 (i.e., an agonist will further increase the signal).

Example 3B

Assesment of Constitutive Activity Using GTP Membrane Binding Scintillation Proximity Assay Using [$^{35}$S]GTPγS binding to measure constitutive activation can be advantageous in that: (a) [$^{35}$S]GTPγS binding is generically applicable to all G protein-coupled receptors; and (b) [$^{35}$S]GTPγS binding is proximal at the membrane surface, thereby making it less likely to pick-up molecules which affect the intracellular cascade. Preferably, a GPCR:Fusion-Protein is utilized. The assay utilizes the ability of G protein-coupled receptors to stimulate [$^{35}$S]GTPγS binding to membranes expressing the relevant receptors. Therefore, the assay may be used to directly screen compounds at the disclosed GPR6 receptor.

A scintillation proximity assay was utilized to monitor the binding of [$^{35}$S]GTPγS to membranes expressing, e.g., the endogenous human GPR6:Gs-Fusion Protein (expressed in 293 cells). In brief, a preferred protocol for the assay is such that the assay was incubated in 20 mM: HEPES, pH 7.4, binding buffer (100 mM NaCl and 10 mM MgCl$_2$), with 0.6 nM [$^{35}$S]GTPγS and 12.5 μg membrane protein and 0.1 μM GDP for 60 minutes. The assay plates were then centrifuged at 400 rpm for 15 minutes at room temperature and then subsequently aspirated and counted in a scintillation counter.

Using this assay, enhanced binding of [$^{35}$S]GTPγS to membranes prepared from 293 cells expressing the control vector alone or the human GPR6:Gsα-Fusion Protein receptor was comparatively observed. The total protein concentration used in the assay affects the total amount of [$^{35}$S]GTPγS binding for each receptor. The c.p.m. differential between the pCMV transfected and the constitutively active GPR6:Gsα-Fusion Protein receptor (at 12.5 ug/ml) increased from approximately 6000 c.p.m to approximately 11,600 c.p.m. protein concentration.

Figure 2:
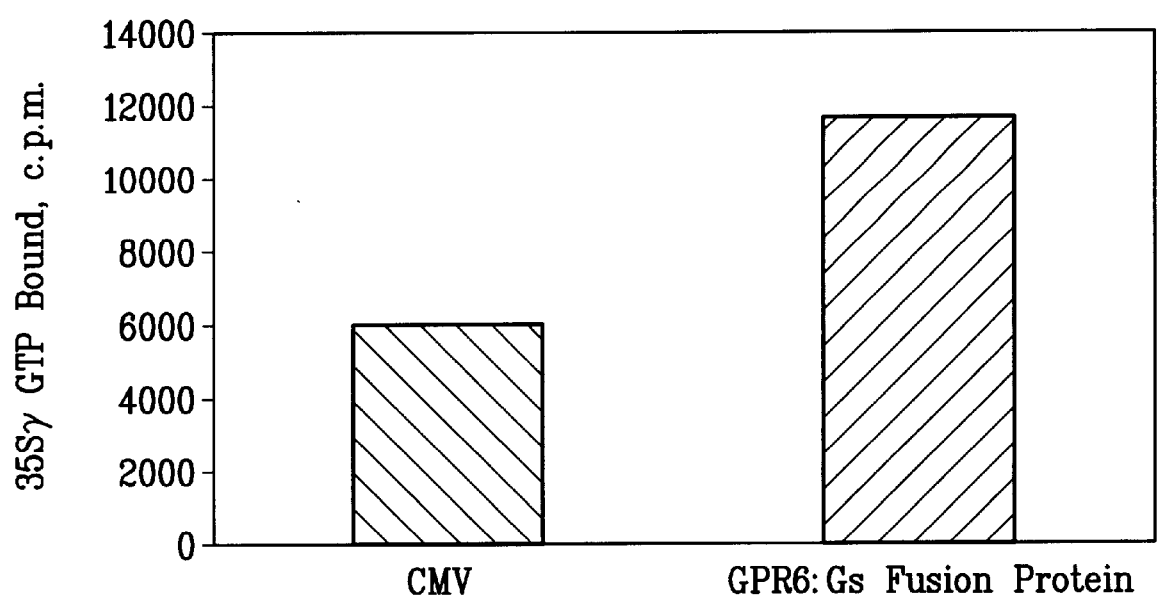
FIG. 2 is a graphic representation of the results of a [$^{35}$S]GTPγS assay providing comparative results for constitutive signaling by GPR6 and GPR6:Fusion Protein.

Results are presented in FIG. 2 and evidence that GPR6 receptor (GPR6:Gsα-Fusion Protein) has increased activity as compared to control; this heightened activity is not the result of autocrine stimulation in that the data were obtained from membrane preparations, as opposed to whole cell preparations.

Example 4A

Direct Identification of Inverse Agonists and Agonist Using [$^{35}$S]GTPγS Assay Although we have utilized endogenous, constitutively active GPR6 for the direct identification of candidate compounds as, e.g., inverse agonists, for reasons that are not altogether understood, intra-assay variation can become exacerbated. Preferably, then, a GPCR Fusion Protein, as disclosed above, is utilized. When such a protein is used, intra-assay variation appears to be substantially stabilized, whereby an effective signal-to-noise ratio is obtained. This has the beneficial result of allowing for a more robust direct identification of candidate compounds. The following protocol is preferred:

1. Membrane Preparation

Membranes expressing the GPCR6:Gsα-Fusion Protein (see Example 2) and for use in the direct identification of candidate compounds as inverse agonists, agonists or partial agonists were prepared as follows:

(a) Materials

Membrane Scrape Buffer was comprised of 20 mM HEPES and 10 mM EDTA, pH 7.4; Membrane Wash Buffer was comprised of 20 mM HEPES and 0.1 mM EDTA, pH 7.4; Binding Buffer was comprised of 20 mM HEPES, 100 mM NaCl, and 10 mM MgCl$_2$, pH 7.4

(b) Procedure

All materials were kept on ice throughout the procedure. Firstly, the media was aspirated from a confluent monolayer of cells, followed by rinse with 10 ml cold PBS, followed by aspiration. Thereafter, 5 ml of membrane Scrape Buffer was added to scrape cells; this was followed by transfer of cellular extract into 50 ml centrifuge tubes (centrifuged at 20,000 rpm for 17 minutes at 4° C.). Thereafter, the supernatant was aspirated and the pellet was resuspended in 30 ml Membrane Wash Buffer followed by centrifuge at 20,000 rpm for 17 minutes at 4° C. The supernatant was then aspirated and the pellet resuspended in Binding Buffer. This was then homogenized using a Brinkman polytron™ homogenizer (15–20 second bursts until the all material was in suspension). This is referred to herein as "Membrane Protein".

2. Bradford Protein Assay

Following the homogenization, protein concentration of the membranes was determined using the Bradford Protein Assay (protein can be diluted to about 1.5 mg/ml, aliquoted and frozen (–80° C.) for later use; when frozen, protocol for use is as follows: on the day of the assay, frozen Membrane Protein is thawed at room temperature, followed by vortex and then homogenized with a polytron at about 12×1,000 rpm for about 5–10 seconds; it is noted that for multiple preparations, the homogenizer should be thoroughly cleaned between homoginezation of different preparations). Membrane protein concentrations are reassessed and normalized to CMV where the optimal protein concentration is between 0.25 ug/ul and 0.30 ug/ul.

(a) Materials

Binding Buffer (as per above); Bradford Dye Reagent; Bradford Protein Standard were utilized, following manufacturer instructions (Biorad, cat. no. 500-0006).

(b) Procedure

Duplicate tubes were prepared, one including the membrane, and one as a control "blank". Each contained 800 ul Binding Buffer. Thereafter, 10 ul of Bradford Protein Standard (1 mg/ml) was added to each tube, and 10 ul of membrane Protein was then added to just one tube (not the blank). Thereafter, 200 ul of Bradford Dye Reagent was added to each tube, followed by vortex of each. After five (5) minutes, the tubes were re-vortexed and the material therein was transferred to cuvettes. The cuvettes were then read using a CECIL 3041 spectrophotometer, at wavelength 595.

3. Direct Identification Assay (a) Materials

GDP Buffer consisted of 37.5 ml Binding Buffer and 2 mg GDP (Sigma, cat. no. G-7127), followed by a series of dilutions in Binding Buffer to obtain 0.2 uM GDP (final concentration of GDP in each well was 0.1 uM GDP); each well comprising a candidate compound, had a final volume of 200 ul consisting of 100 ul GDP Buffer (final concentration, 0.1 uM GDP), 50 ul Membrane Protein (12.5 ug) in Binding Buffer, and 50 ul [$^{35}$S]GTP$\gamma$S (0.6 nM) in Binding Buffer (2.5 ul [$^{35}$S]GTP$\gamma$S per 10 ml Binding Buffer).

(b) Procedure

Candidate compounds (Tripos, Inc., St. Louis, Mo.) were received in 96-well plates (these can be frozen at −80° C.). Membrane Protein (or membranes with expression vector excluding the GPR6:Gs$\alpha$-Fusion Protein, as control), were homogenized briefly until in suspension. Protein concentration was then determined using the Bradford Protein Assay set forth above. Membrane Protein (and control) was then diluted to 0.25 mg/ml in Binding Buffer (final assay concentration, 12.5 ug/well). Thereafter, 100 ul GDP Buffer was added to each well of a Wallac Scintistrip™ (Wallac). A 5 ul pin-tool was then used to transfer 5 ul of a candidate compound into such well (i.e., 5 ul in total assay volume of 200 ul is a 1:40 ratio such that the final screening concentration of the candidate compound is 10 uM). Again, to avoid contamination, after each transfer step the pin tool was rinsed in three reservoirs comprising water (1×), ethanol (1×) and water (2×)—excess liquid should be shaken from the tool after each rinse and dried with paper towels and kimwipes™. Thereafter, 50 ul of Membrane Protein was added to each well (a control well comprising membranes without the GPCR Fusion Protein is also utilized), and pre-incubated for 5–10 minutes at room temperature (the plates were covered with foil in that the candidate compounds obtained from Tripos are light sensitive). Thereafter, 50 ul of [$^{35}$S]GTP$\gamma$S (0.6 nM) in Binding Buffer was added to each well, followed by incubation on a shaker for 60 minutes at room temperature (again, in this example, plates were covered with foil). The assay was then stopped by spinning of the plates at 4000 RPM for 15 minutes at 22° C. The plates were then aspirated with an 8 channel manifold and sealed with plastic plate covers. The plates were then read on a Wallac 1450 using setting "Prot. #37" (as per manufacturer instructions).

Example 4B

Direct Identification of "Leads"

We believe that it is important to note that the following results have been obtained using an orphan receptor; as the data support, it is possible, using the techniques disclosed herein, to directly identify candidate compounds that modulate the orphan receptor as inverse agonists, agonists and partial agonists, directly from a primary screen; indeed, the methods disclosed herein are sensitive enough to allow for direct identification of both inverse agonist and agonist modulators on the same assay plate.

The initial or "primary" screen designed to directly identify, e.g., human GPR6 receptor inverse agonists, consisted of the membrane-based GTP$\gamma$S binding assay of Example 4A utilizing membranes prepared from 293 stable cells. Candidate compounds directly identified as inhibiting receptor-mediated increases in GTP$\gamma$S as set forth below were considered active "leads". Primary assay leads were then re-tested in the same assay to reconfirm their inverse agonist activity. If primary assay hits were reconfirmed active (50% or greater inhibition), and therefore directly identified as, e.g., an inverse agonist, additional candidate compounds were synthesized based upon the structures of the reconfirmed hits (geared towards, e.g., improvement in the characteristics of the compounds) whereby the directed library compounds (Arena Pharmaceuticals, Inc., San Diego Calif.) were then evaluated. The last step in secondary assay evaluation was to determine if test compounds were capable of inhibiting cAMP accumulation (i.e., adenylate cyclase-based assay, disclosed below in Example 4C). This final assay confirms that the directly identified compounds retained inverse agonist properties.

Figure 3:
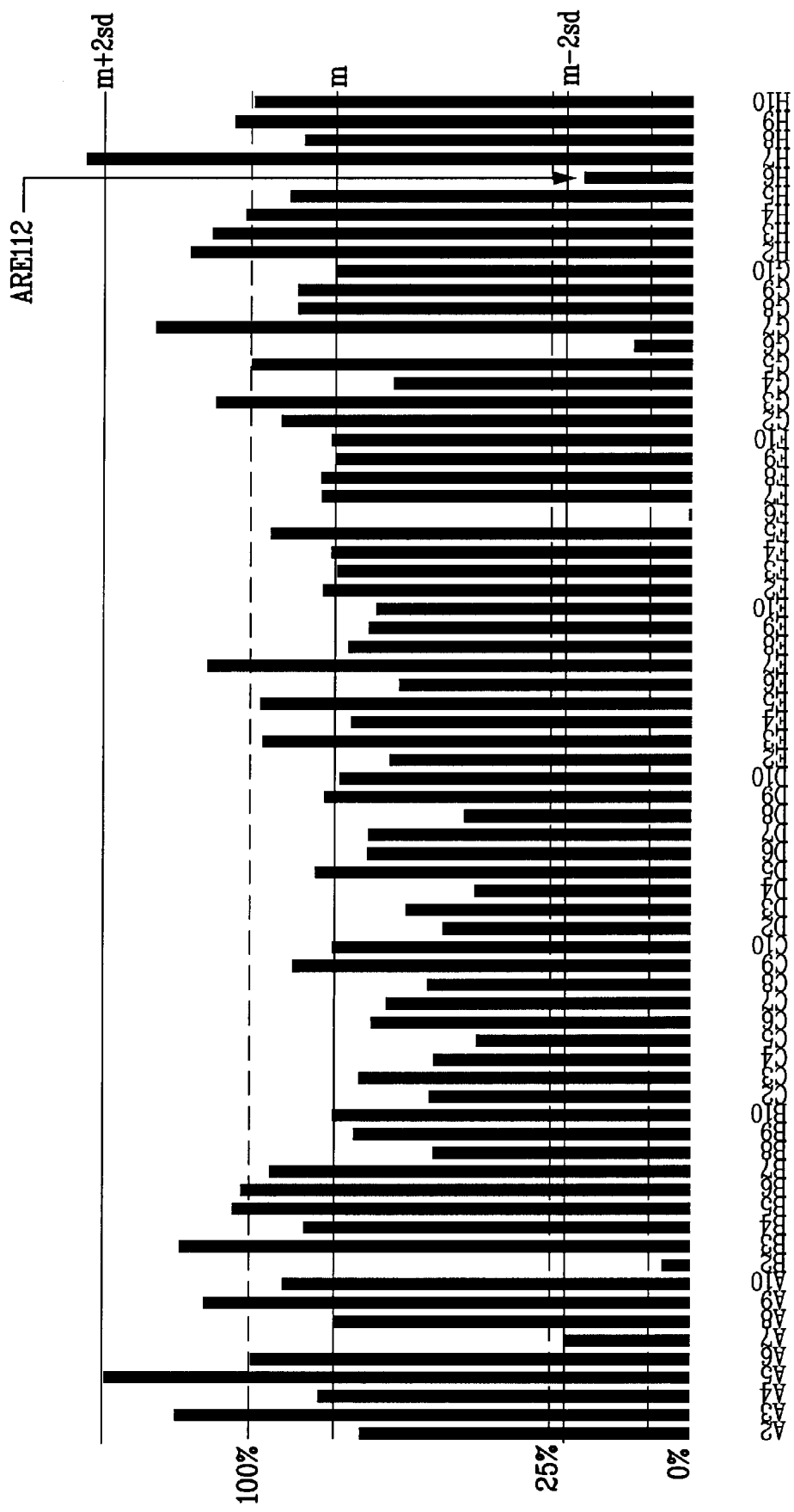
FIG. 3 is a graphic representation of results from a primary screen of several candidate compounds against GPR6; results for compound "ARE112" are provided in well H6.

A representative screening assay plate (96 well format) result is presented in FIG. 3. Each bar represents the results for a different compound in each well, plus the GPR6:Gs Fusion Protein. The representative results presented in FIG. 3 also provide standard deviations based upon the mean results of each plate ("m") and the mean plus two standard deviations ("m+2sd") and the mean minus two standard deviations ("m−2sd"). Our arbitrary preference for selection of inverse agonists as "leads" from the primary screen involves selection of candidate compounds that reduce the per cent response by at least the mean plate response, minus two standard deviations. Based on this selection process, the candidate compounds in the following wells were directly identified as putative inverse agonists to the GPR6 receptor: A7; B2; F6; G6 and H6. Further evaluation (using a non-GPR6 receptor) of compounds designated in wells A7, B2, F6 and G6 indicated that these compounds were non-specific to GPR6:Gs-Fusion Protein receptor and thus may instead act to uncouple the G protein from the GPR6 receptor (data not shown). Thus, the candidate compound of well H6, designated "ARE112" was selected for further evaluation.

Figure 4:
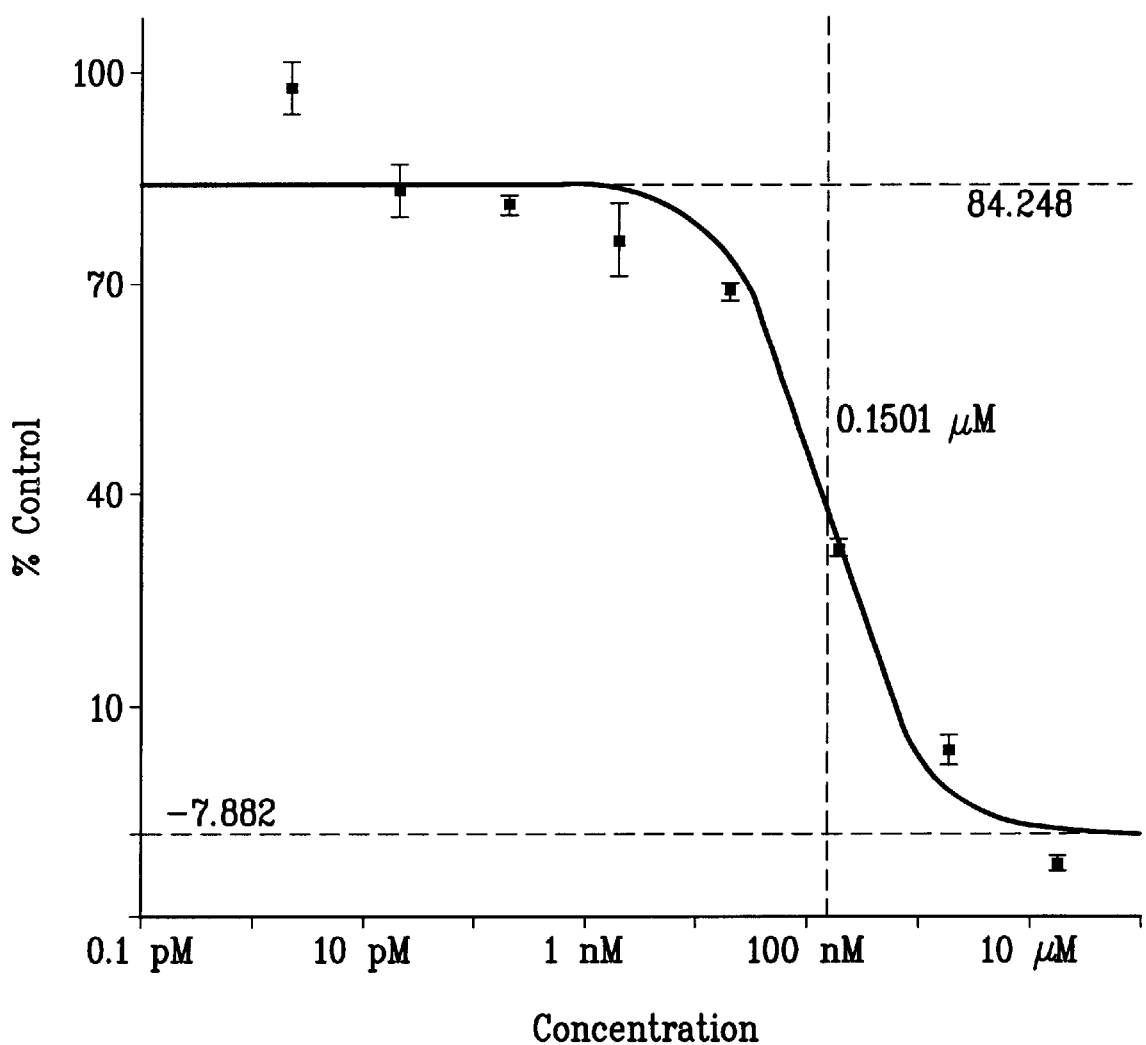
FIG. 4 is a graphic representation of an $IC_{50}$ curve for compound ARE112 against the GPR6 receptor, indicating an $IC_{50}$ value of 0.1501 μM.

It is preferred that following such direct identification, IC$_{50}$ (inverse agonist) or EC$_{50}$ (agonist) values be determined; those having ordinary skill in the art are credited with utilizing IC$_{50}$ and EC$_{50}$ assay protocols of choice. FIG. 4 provides a representative IC50 curve for compound ARE112 using the assay protocol of Example 4A.

Example 4C

Cyclic AMP Confirmation Assay

Using an independent assay approach to provide confirmation of a directly identified candidate compound as set forth above, it is preferred that a confirmation assay then be utilized. In this case, the preferred confirmation assay is membrane-based cyclic AMP (cAMP) assay.

A modified Flash Plate™ Adenylyl Cyclase kit (New England Nuclear; Cat. No. SMP004A) was utilized for confirmation of candidate compounds directly identified as inverse agonists and agonists to endogenous, constitutively activated orphan GPCRs in accordance with the following protocol.

Transfected stable cells were harvested approximately three days after transfection. Membranes were prepared by homogenization of suspended cells in buffer containing 20 mM HEPES, pH 7.4 and 10 mM $MgCl_2$. Homogenization was performed on ice using a Brinkman Polytron™ for approximately 10 seconds. The resulting homogenate was centrifuged at 20,000 rpm for 20 minutes at 4° C. The resulting pellet was then resuspended in buffer containing 20 mM HEPES, pH 7.4 and 0.1 mM EDTA, homogenized for 10 seconds, followed by centrifugation at 20,000 rpm for 20 minutes at 4° C. The resulting pellet can be stored at −80° C. until utilized. On the day of direct identification screening, the membrane pellet is slowly thawed at room temperature, resuspended in buffer containing 20 mM HEPES, pH 7.4, 100 mM NaCl and 10 mM $MgCL_2$, to yield a final protein concentration of 0.60 mg/ml (the resuspended membranes are placed on ice until use).

cAMP standards and Detection Buffer (comprising 2 µCi of tracer [125I cAMP (50 µl) to 11 ml Detection Buffer) were prepared and maintained in accordance with the manufacturer's instructions. Assay Buffer was prepared fresh for screening and contained 20 mM HEPES, pH 7.4, 100 mM NaCl, 10 mM $MgCl_2$, 20 mM phosphocreatine (Sigma), 0.1 units/ml creatine phosphokinase (Sigma), 50 µM GTP (Sigma), 0.2 mM ATP (Sigma) and 0.6 mM isobutyl-methyl xanthine (IBMX); Assay Buffer can be stored on ice until utilized.

Candidate compounds identified as per above (if frozen, thawed at room temperature) were added to plate wells (3 µl/well; 12 µM final assay concentration), together with 50 µl Membrane Protein (30 µg/well) and 50 µl of Assay Buffer. This admixture was then incubated for 30 minutes at room temperature, with gentle shaking.

Following the incubation, 100 µl of Detection Buffer was added to each well, followed by incubation for 2–20 hours. Plates were subsequently aspirated and then counted in a Wallac MicroBeta™ plate reader using "Prot. #31" (as per manufacturer instructions).

The following Table A lists the $IC_{50}$ values determined utilizing the foregoing cAMP assay.

TABLE A

| Assay Number For Compound ARE112 | $IC_{50}$ Values (nM) cAMP | Maximum (c.p.m.) | Minimum (c.p.m.) |
| --- | --- | --- | --- |
| 1 | 88.3 | 138.1 | 4.3 |
| 2 | 77.39 | 128.5 | 2.7 |
| 3 | 99.00 | 125.7 | 3.2 |

Preferably, for $IC_{50}$ determinations, the dose response range at the maximum is between 80 and 120 percent control ("% control"), and at the minimum between 20 and −20 percent control, although such parameters can be a matter of choice for the artisan, depending upon the particular needs of the artisan.

Example 5

Screening of Directed Library

Based upon the foregoing results, structure activity analysis of the ARE112 compound suggested that a series of derivatives of ARE112, N-(5,6-dihydro-3H-imidazo[2,1-c]-1,2,3-dithiazol-3-ylidene), as well as derivatives of ARE111 N-(2-thioxo-imidazolidine-1-carbothioyl) would exhibit similar GPR6 inverse agonist activity and selectivity, A directed library series of derivatives of N-(5,6-dihydro-3H-imidazo[2,1-c]-1,2,3-dithiazol-3-ylidene) and of N-(2-thioxo-imidazolidine-1-carbothioyl) were synthesized (see Examples 8 and 9, infra). $IC_{50}$ values were determined using the assays indicated below, by taking the mean values of the number of assays (placed in brackets), +/− the standard deviation. These, too were assessed using the above protocols, and results are summarized below in Table B:

TABLE B

| Compound Identifier | $IC_{50}$ Values GTP Assay Example 4A (µM) | $IC_{50}$ Values Cyclic AMP Assay Example 4C (µM) |
| --- | --- | --- |
| ARE111 | 2.79 +/− 1.14 (4) | 1.96 +/− 2.51 (4) |
| ARE112 | 0.42 +/− 0.24 (12) | 0.10 +/− 0.07 (5) |
| ARE113 | 100 +/− 110 (4) | N/D |
| ARE114 | 0.44 +/− 0.46 (3) | 0.17 +/− 0.01 (2) |
| ARE115 | 1.57 +/− 1.748 (5) | 3.65 +/− 3.45 (8) |
| ARE116 | 0.57 +/− 0.24 (7) | 0.17 +/− 0.05 (5) |
| ARE117 | 200 (3) | N/D |
| ARE118 | 0.65 +/−0.67 (3) | 0.37 +/− 0.18 (6) |
| ARE119 | 0.45 +/− .12 (3) | 1.97 +/− 1.53 (3) |
| ARE120 | 0.64 +/− 0.25 (6) | 0.27 +/− .02 (5) |
| ARE121 | 122 +/−100 (5) | 55 +/− 96 (4) |
| ARE122 | 0.83 +/−0.12 (2) | 0.21 +/− 0.19 (2) |
| ARE123 | 56 +/− 95 (4) | 51 +/− 98 (4) |
| ARE124 | 0.31 +/− 0.11 (4) | 0.40 +/− 0.25 (3) |
| ARE125 | 3.8 +/− 3.5 (3) | 120 +/− 100 (5) |
| ARE126 | 0.79 +/− 0.08 (3) | 0.14 +/− 0.04 (2) |
| ARE127 | 1.25 +/− 0.22 (3) | 0.48 +/− 0.40 (4) |
| ARE128 | 0.37 +/− 0.02 (2) | 0.20 +/− 0.13 (6) |
| ARE129 | 3.19 +/− 3.63 (3) | 2.62 +/− 4.26 (4) |
| ARE130 | 0.22 +/− 0.22 (3) | 0.24 +/− 0.19 (5) |
| ARE131 | 43 +/− 87 (5) | 200 (4) |
| ARE132 | 0.35 +/− 0.35 (2) | 0.10 +/− 0.01 (2) |
| ARE133 | 0.11 +/− 0.11 (4) | 0.17 +/− 0.07 (5) |
| ARE134 | 0.41 +/− 0.26 (6) | 0.19 +/− 0.19 (4) |
| ARE135 | 100 +/− 130 (2) | 0.71 +/− 0.74 (4) |
| ARE136 | 0.17 +/− 0.07 (3) | 0.17 +/− 0.13 (5) |
| ARE137 | 200 (3) | 100 +/− 100 (2) |
| ARE138 | 0.45 +/− 0.16 (3) | 0.13 +/− 0.07 (3) |
| ARE139 | 0.26 +/− 0.22 (3) | 4.52 +/− 3.14 (3) |
| ARE140 | 0.13 +/− 0.06 (3) | 0.19 +/− 0.21 (5) |
| ARE143 | 68.29 +/− 0.11 (3) | 160 +/− 0.09 (5) |
| ARE144 | 0.25 +/− 0.03 (3) | 0.11 +/− 0.05 (2) |
| ARE148 | 0.46 +/− 0.27 (4) | 0.35 +/− 0.21 (5) |
| ARE149 | 2.43 +/− 2.12 (4) | 5.83 +/− 4.95 (3) |
| ARE150 | 0.33 +/− 0.07 (2) | 0.10 +/− 0.19 (3) |
| ARE151 | 200 (3) | 200 (3) |
| ARE152 | 0.1897 (3) | N/D |
| ARE153 | 2.46 +/− 0.42 (3) | N/D |
| ARE154 | 200 (3) | 80 +/− 103 (3) |
| ARE155 | 6.56 +/− 2.0 (3) | 0.85 +/− 0.24 (3) |
| ARE156 | 0.67 +/− 0.11 (3) | 0.133 +/− 0.06 (2) |

N/D = data not yet determined

Example 6

In vivo Analysis

1. Food/Water Intake and Body Weight in 24-Hour Food-Deprived Animals

The profile of ARE112 from the in vitro functional assays suggested that this compound exhibits selective GPR6 inverse agonist properties. An in vivo assessment of GPR6 inverse agonist was accomplished by determining the effects of ARE112 on food intake after food deprivation in rats. Food deprivation was used to induce higher than normal eating behavior (e.g., controlvehicle-treated animals were hyperphagic).

The animals (male Sprague-Dawley rats were used for the following experiments) were food deprived for 24 hr, and then injected intraperitoneally (IP) with 0, 6.75, 13.5, 27 and 54 mg/kg of compound ARE112. After 30 min, rats were introduced to standard rat chow pellets and observed thereafter for a period of 6.5 hours post-injection.

Data evidence that animals treated IP with compound ARE112 exhibit decreased food intake, water intake and body weight gain. In FIG. 5A, at 1.5 hours after injection, vehicle treated animals consumed about 6 grams of food, while ARE112 treated (54 mg/kg) consumed 3 g of food. As time progressed, the data indicate that vehicle-treated ate substantially more food (up to 14 g at 6.5 hours post-injection), while the ARE112 treated, particularly animals treated with 54 mg/kg of ARE112, consumed 4 g (see, FIG. 5A). Four and 5 fold decreases in water intake at doses of 27 and 54 mg/kg, respectively, were also evidenced by the data, which appear to parallel the decreased amount of food eaten. (See, FIG. 5B). Vehicle treated rats evidenced a body weight gain of 20 g, whereas ARE112 treated rats evidenced the following: 13.5 mg/kg treatment—11 g weight gain; 27 and 54 mg/kg treatment—no weight gain (see, FIG. 5C).

2. Basal Food/Water Intake and Body Weight in Non-Food Deprived Animals

Animals were also observed during their most active period (dark cycle), and both basal food and water intake were measured. In this test, animals were not deprived of food but were instead observed for normal activity.

Animals were administered ARE112 at 0, 6.75, 13.5, 27 and 54 mg/kg, IP 30 min prior to the beginning of their dark cycle (i.e. 6:30 pm) and were then exposed to standard rat chow pellets (i.e. 30 min after compound administration) and observed for a period of 15.5 hr post administration. Data, presented in FIG. 6A, evidence that animals administered with ARE112 did not eat as much as animals administered vehicle. For example, the vehicle treated animals consumed 9 g of food over a period of 4 hrs, whereas animals treated with dose of 13.5 mg/kg and 54 mg/kg consumed less than half this amount over this same period (4 and 2 g of food, respectively). Similar to the food-deprived rats, the non-deprived rats also exhibited a decrease in water intake and body weight gain. (See, FIGS. 6B and 6C).

Figure 11:
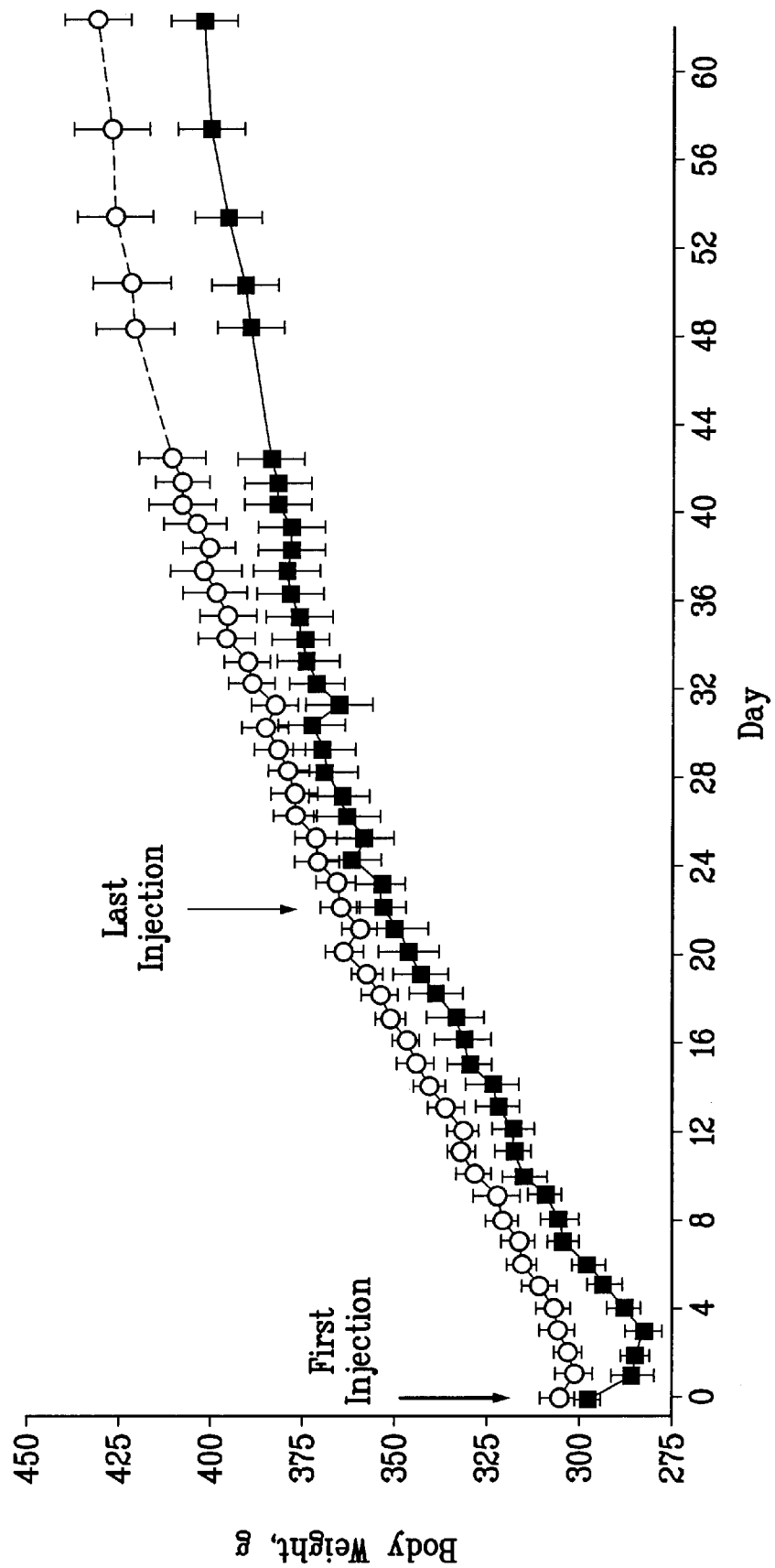
FIG. 11 provide a graphic representation of the results of a daily repeated in vivo (IP) administration of ARE112 rats showing a long-term decrease in body weight in non food deprived.

Long-term effects (60 days) of ARE112 were also examined. Animals (treatment, n=4; control, n=5) were treated once a day intraperitoneally with ARE112 for 22 days and assessed for a period of 60 days. On days 1 to 3, animals treated with dose of 13.5 mg/kg initially lost body weight and between day 4 and day 31, animals gradually gained weight, although still weighing less than vehicle treated animals. After day 31 and through day 60, the data support the position that there was a significant difference in body weight between the treated animals and the vehicle animals.' The data support the conclusion that daily, repeated administration of ARE112 (at 13.5 mg/kg) induces a long-term decrease in body weight in non-food deprived rats. See, FIG. 11.

3. Intracerebroventricular (ICV) Administration of ARE112 on Food-Deprived Animals a. Surgery Animals were prepared with an ICV cannula aimed above the lateral ventricle. For this surgery, animals were placed under general anesthesia using continuous inhalation of isoflurane and secured in a Kopf stereotaxic instrument. Surgery was performed in a dedicated surgery room, using sterile instruments, surgical gloves and aseptic procedures to prevent clinical infections. The surgical site was shaved and disinfected with betadine solution and alcohol. Animals were observed continuously for the level of anesthesia by testing for the animals' responses to tail- or paw-pinch. A cannula made of 23 gauge stainless steel tubing (7 mm long) was lowered to a point 1 mm above the ventricle, using coordinates: A/P−0.6 mm from bregma, M/L+/−2.0 mm from bregma, D/V 3.2 mm below skull surface. The guide was anchored to the skull with three stainless steel screws and dental cement. Coordinates were based on stereotaxic atlas such as Paxinos and Watson sterotaxic atlas (Paxinos, G. and Watson, C, The Rat Brain, New York, Academic Press, 1982). After cannula implantation, a 30-gauge stainless steel dummy stylet was inserted into the cannula. At the conclusion of surgery, a heat source (heat lamp directed towards one half of recovery cage) was used to maintain body temperature while the animals recovered from anesthesia. Animals were allowed at least one week of recovery after surgery before ICV injection of compound was performed.

b. Administration of ARE112

Animals were food-deprived for 24 hours prior to administration of the compound.

For ICV injection, the dummy stylet was removed from the implanted cannula, and a 30-gauge stainless steel injector cannula containing ARE112 suspension in a 45% cyclodextrin solution was inserted to a depth 1.5 mm beyond the ventral tip of the implanted cannula. The other (noninserted) end of the injector cannula was attached to 60 cm of PE10 tubing containing the compound suspension, which was attached at the free end of tubing to a 25 $\mu$l Hamilton syringe. Ten microliters of ARE112 suspension (containing, 0, 25, 50, and 100 nmol) were then delivered via gentle and even mechanical pressure to the plunger of the Hamilton syringe. The volume of injection was verified by marks on the PE 10 tubing previously calibrated with a 10 $\mu$l Hamilton syringe. At the conclusion of injection, any fluid observed from the dorsal tip of the implanted cannula upon withdrawal of the injector cannula was noted, and the dummy stylet was inserted into the implanted cannula.

Figure 7A:
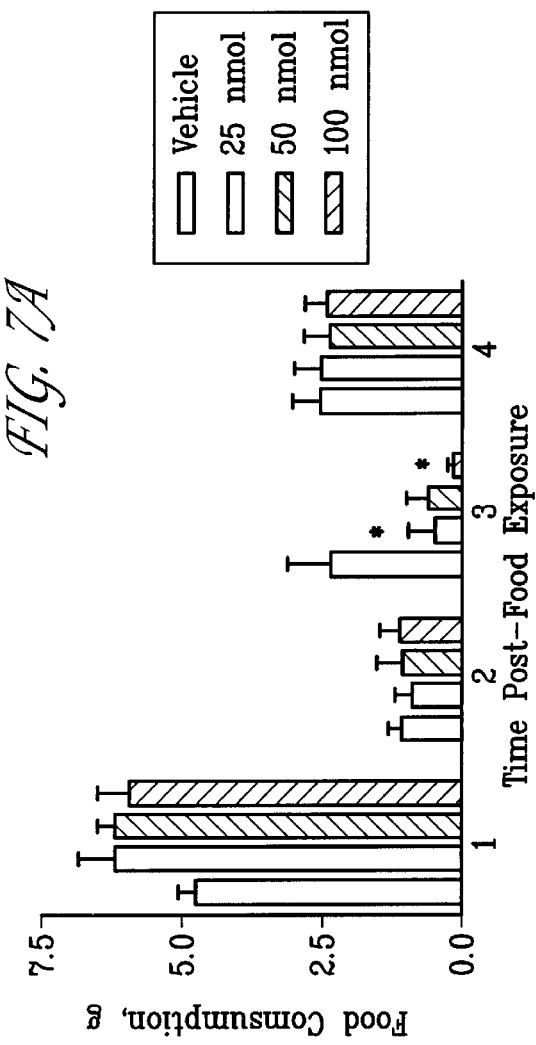
FIGS. 7A, 7B and 7C provide graphic representations of the results of in vivo administration (ICV) of ARE112 on cumulative food intake (7A), water intake (7B) and body weight gain (7C) on 24-hour food deprived rats.
Figure 7C:
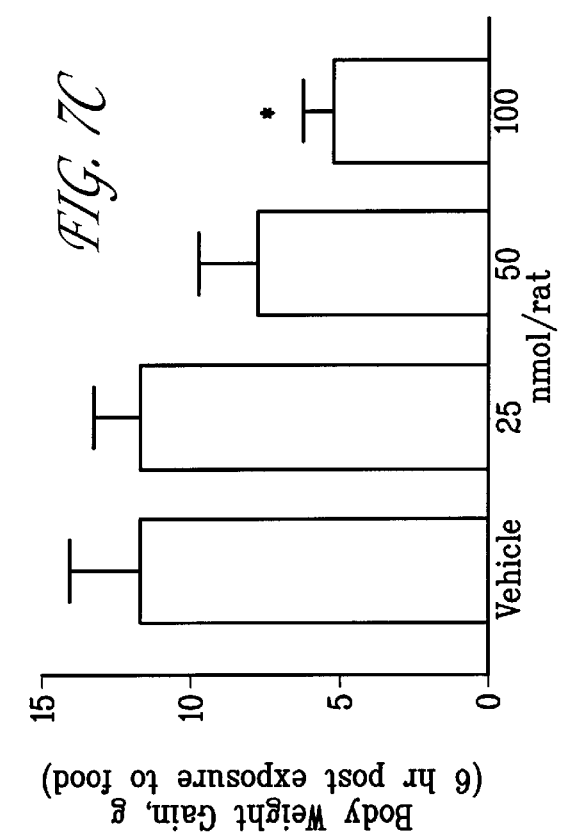
Figure 7B:
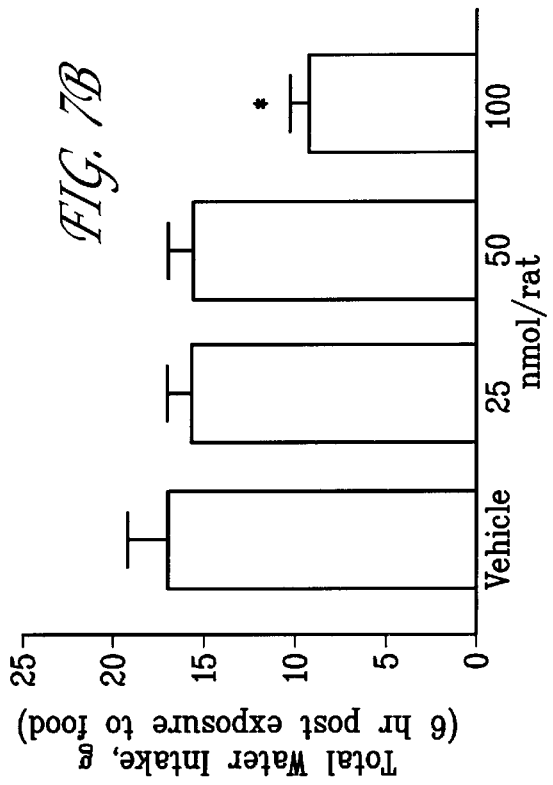

Data evidence that after two hours post-administration of ARE112 at all doses, animals consumed substantially less food (about 6 fold less food was consumed). After three hours, the vehicle rat consumed about 2.5 grams of food, while ARE112 treated rats consumed about 1.0 grams or less. See, FIG. 7A. Treated animals (at 25 and 50 nmol) drank a comparable amount of water as the vehicle, i.e., about 17 grams. At higher doses (e.g., 100 nmol), about less than half that amount was consumed. See, FIG. 7C. The data evidence, consistent with the data developed using IP administration, that at a dose of 100 nmol of ARE112, the ICV treated animal gained substantially less weight (e.g., 5 grams) when evaluated against the vehicle, which gained about 12 grams. See, FIG. 7C.

4. Effect of ARE112 on Motor Function

The effect of ARE112 on motor function was also examined. Motor function was assessed by using automated locomotor activity cages. Animals were placed in a standard rodent cage surrounded by photocell, which allowed for automated recording of motor activity. Animals were under no motivational constraints and were free to move around the cage.

Figure 8:
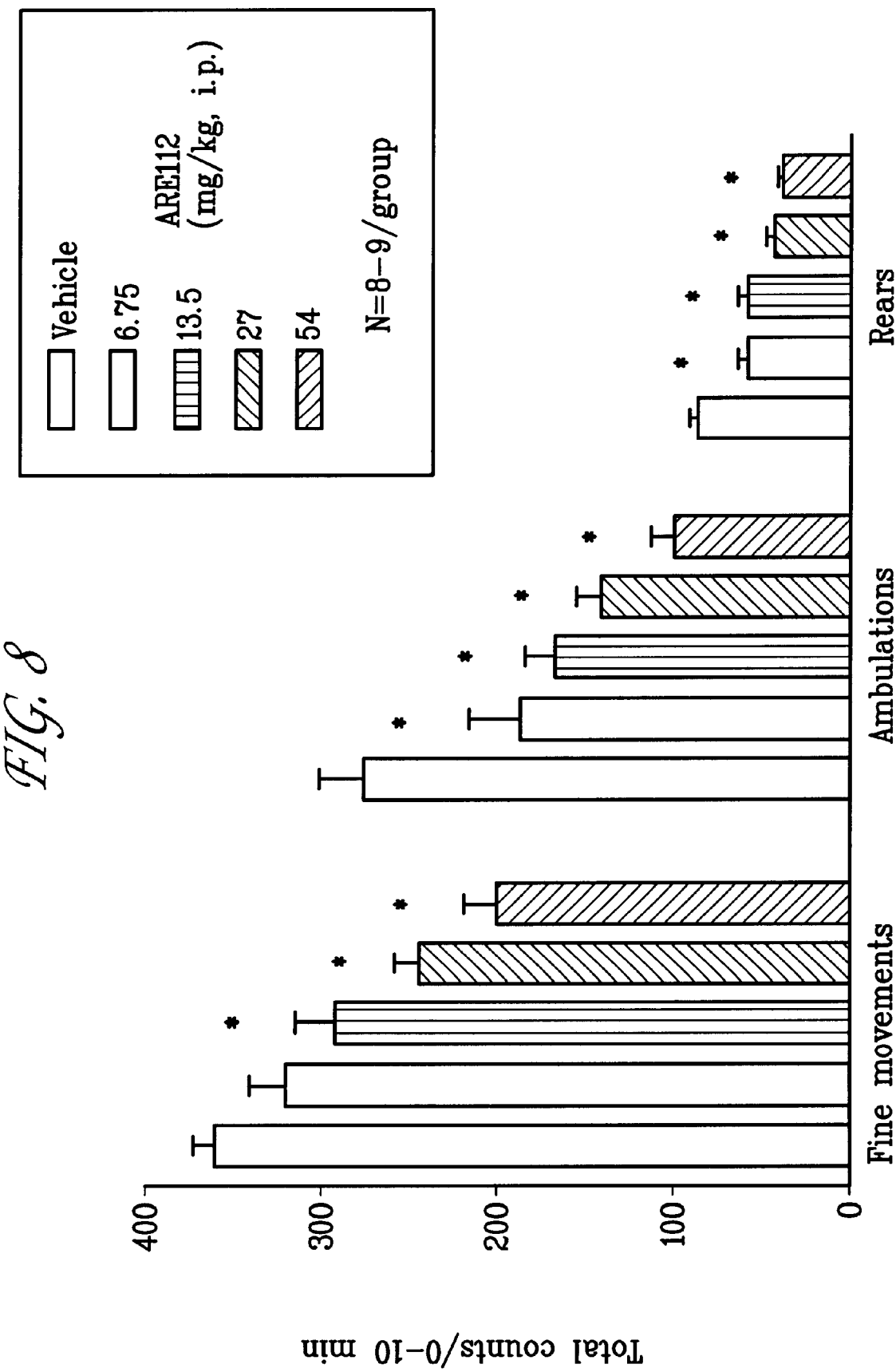
FIG. 8 provides a graphic representation of the results of ARE112 on locomotor activity on rats 16 hours post-administration.

Male Sprague-Dawley rats (n=4–9 per dose) were administered ARE112 (IP) prior to placement into in locomotor activity cages. Data are presented in FIG. 8. Based upon the data, it can be concluded that ARE112 does not affect locomotor activity where animals were exposed to locomotor activity cages for 1.5 hour immediately after injection of ARE112. While the data support the conclusion that ARE112 decreases locomotor activity in rats 16 hours post-injection (see, FIG. 8), thus indicating that ARE112 has some sedative activity, (e.g., the animals appear relaxed and demonstrate little to no anxiety-like behavior), this sedative activity is mild and cannot, in and of itself, account for the decrease in food intake.

Figure 12:
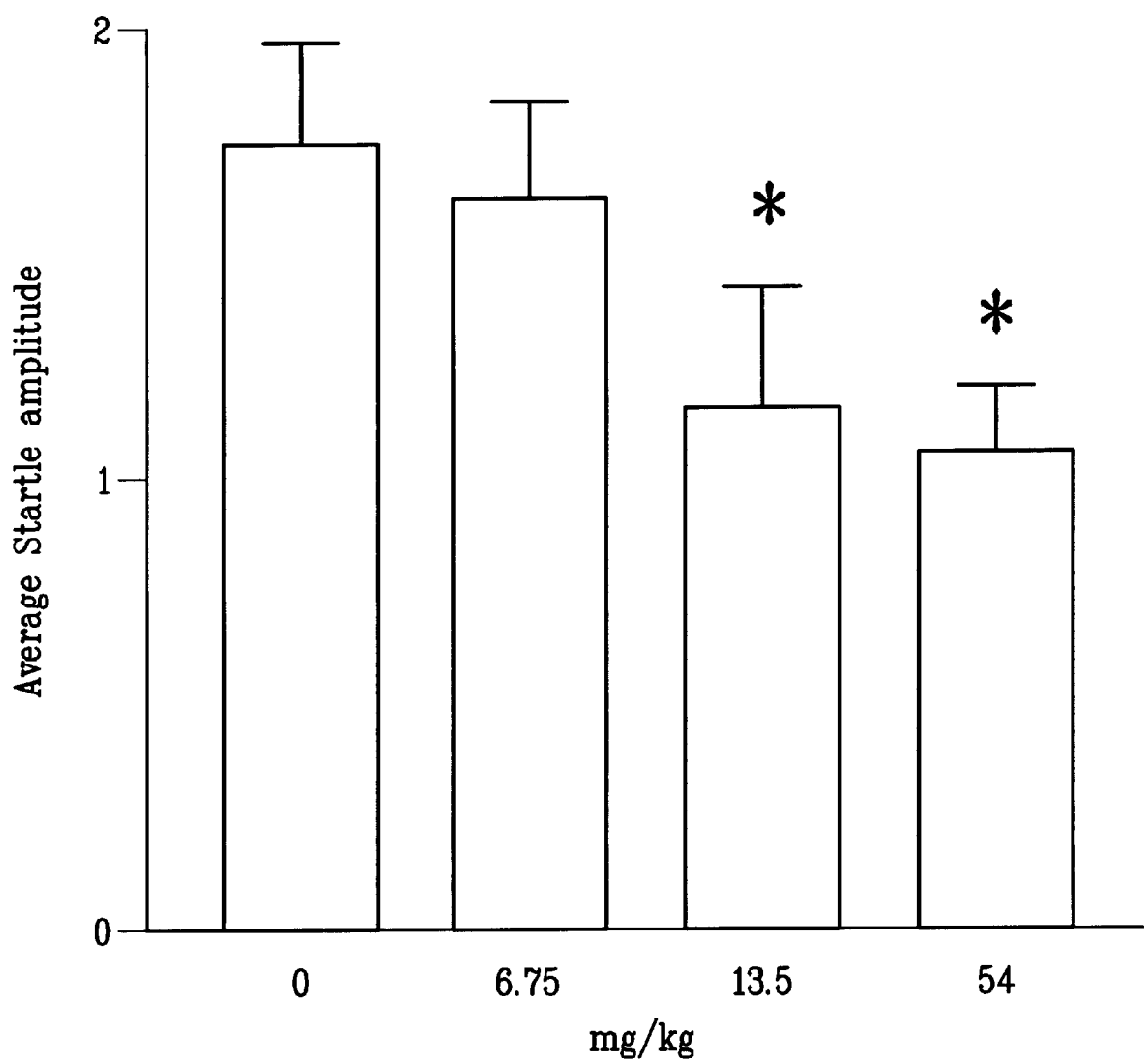
FIG. 12 provide a graphic representation of the results of in vivo (oral-gavage) administration of ARE112 showing a decrease in startle reflex in non food deprived rats.

As further evidence of this mild sedative activity, animals were measured to determine their startle reflexes. In this assay, ARE112 was orally administered in non-food deprived rats 4.5 hours prior to testing. Animals were subjected to a pre-pulse of 12 db followed by a 120 db pulse and subsequently measured for the height in which the animals jumped. FIG. 12 shows the average startle amplitude of administered rats (i.e., at 6.75, 13.5 and 54 mg/kg). Treated rats at 13.5 and 54 mg/kg did not jump as high, as compared to the vehicle and rats treated at the low dose of 6.75 mg/kg, in response to the pulse. This data further suggests that at a higher dosage of ARE112 , animals demonstrate a mild sedative activity.

5. Oral Availability: ARE112

Figure 9A:
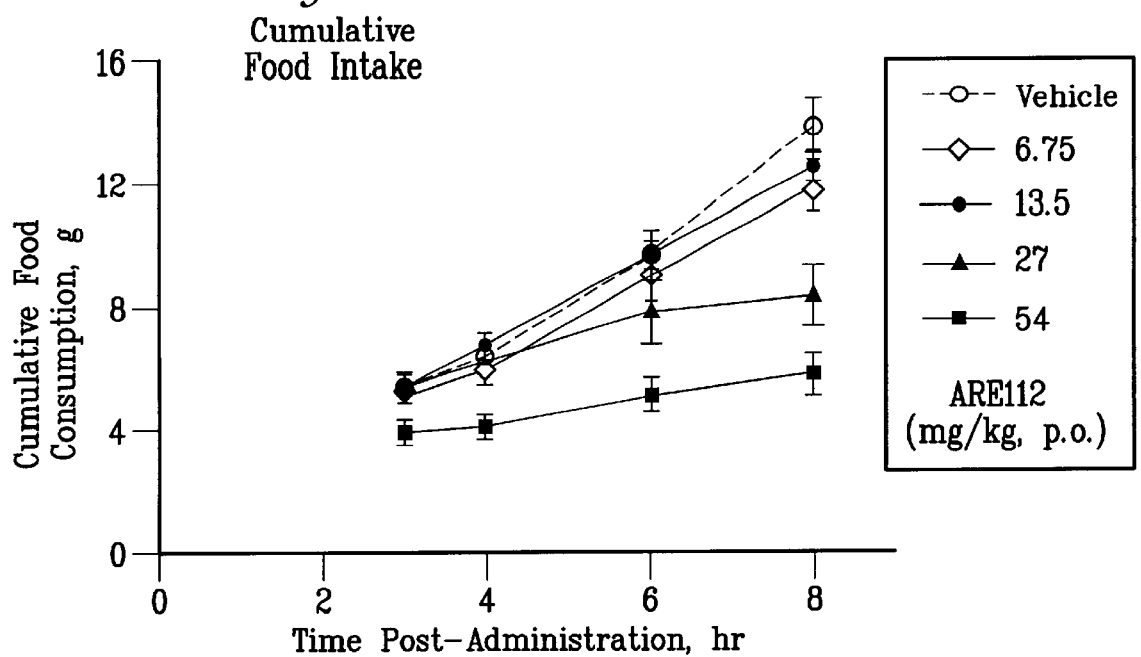
FIGS. 9A and 9B provide graphic representations of the results of in vivo administration (oral-gavage) of ARE112 on cumulative food intake on 24-hour food deprived rats (9A) and on cumulative food intake on non food deprived rats (9B).
Figure 9B:
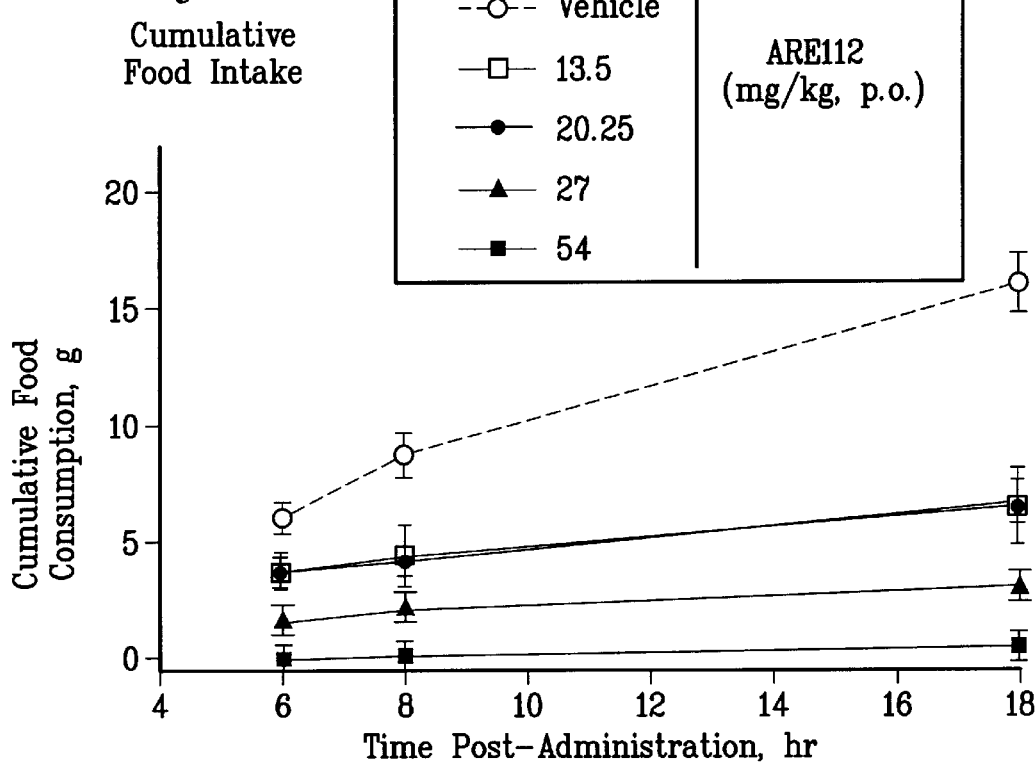

Based upon the in vivo data developed, oral bioavailability of compound ARE112 was determined. The compound was administered by oral gavage at doses ranging from 6.75 to 54 mg/kg. The data presented in FIGS. 9A and 9B support the conclusion that oral administration of ARE112 also decreases food intake in both food-deprived and non-food deprived rats. The effect of ARE112 was dose-dependent and comparable to the effect observed after IP administration. In FIG. 9A, rats were deprived 24 hours prior to oral administration of the compound. In this assay, the vehicle-treated rats at 2.5 hours consumed about 6 grams of food while injected rats; particularly rats administered with 27 and 54 mg/kg of ARE 112, ate about 6 and 4 grams, respectively. As time progressed, the vehicle rat consumed significantly more, about 14 grams at 8 hours post-administration, while treated rats (at 27 and 54 mg/kg) consumed about 8 grams and 6grams, respectively. (See, FIG. 9A).

In a second assay, rats were treated with ARE112 by oral gavage but were not food deprived. Data evidence an even greater decrease in food intake, such that at 18 hours post administration of the compound, the vehicle rats had consumed about 15 grams of food while the injected rats (at all doses) ate 5 grams or less; about a three fold decrease in food consumption when treated with compound ARE112. (See, FIG. 9B). These data support the conclusion that ARE112 is orally active.

6. Assessment of Other Compounds.

Several other GPR6 inverse agonists were also assessed under 24-hour food deprived conditions, with PO administration. The analogs listed below were tested at 200 μmol/kg, which is equivalent to 54 mg/kg. In addition, ARE114 was also assessed at 100 mol/kg (27 μmol/kg). Data are summarized below in Table C:

TABLE C

| Analogs | Cumulative Food Intake (g) (8 hr post administration) | Cumulative Water Intake (g) (6 hr post administration) | Body Weight Gain (g) (6 hr post administration) |
|---|---|---|---|
| Vehicle | 14.5 | 22.9 | 20.3 |
| ARE114 (100 μmol/kg) | 10.8 | 15.3 | 13.6 |
| ARE114 (200 μmol/kg) | 8.68 | 10.6 | 6.18 |
| ARE120 (200 μmol/kg) | 9.88 | 18.5 | 11.4 |
| ARE128 (200 μmol/kg) | 7.93 | 8.5 | 4.03 |

In a second assay, tested under the same conditions, several other analogs were assessed at 100 μmol/kg. Data are summarized below in Table D.

TABLE D

| Analogs (100 μmol/kg) | Cumulative Food Intake (g) (8 hr post administration) | Cumulative Water Intake (g) (6 hr post administration) | Body Weight Gain (g) (6 hr post administration) |
|---|---|---|---|
| Vehicle | 14.0 | 19.25 | 19.25 |
| ARE112 | 8.1 | 10.5 | 6.25 |
| ARE130 | 9.1 | 9.5 | 9.5 |
| ARE135 | 13.5 | 19.5 | 19.5 |
| ARE136 | 9.0 | 15.25 | 11.0 |
| ARE140 | 9.6 | 20.0 | 14.6 |

Figure 10A:
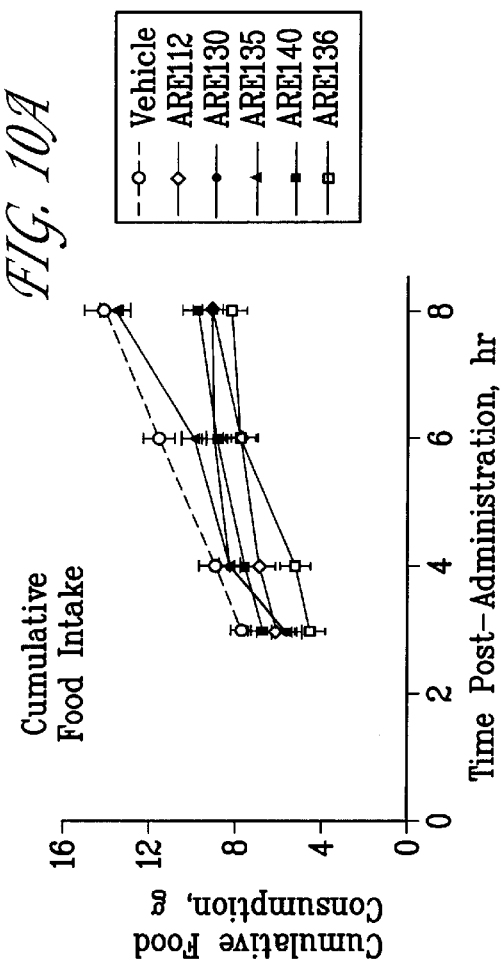
FIGS. 10A, 10B and 10C provide graphic representations of the results of in vivo administration (oral-gavage) of structural analogs of ARE112 on cumulative food intake (10A), water intake (10B) and body weight gain (10C) on 24-hour food deprived rats.
Figure 10C:
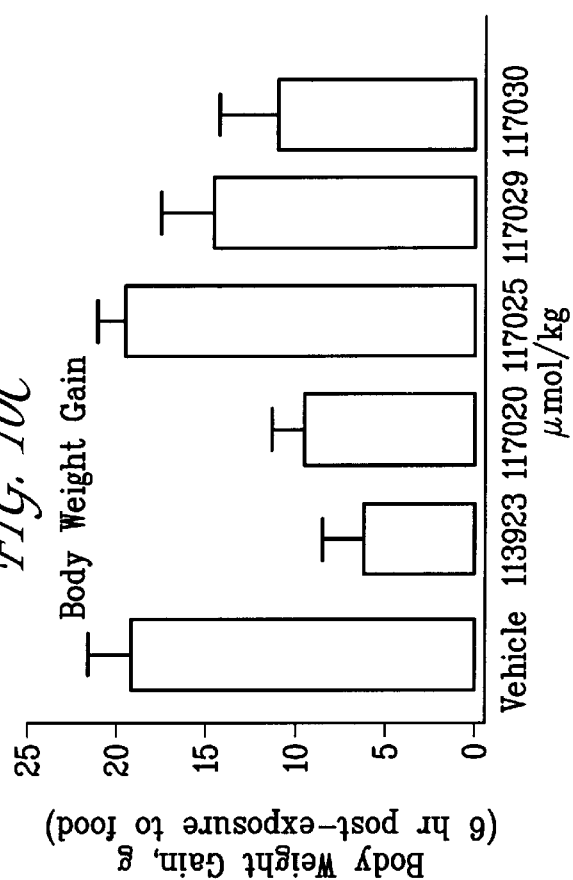
Figure 10B:
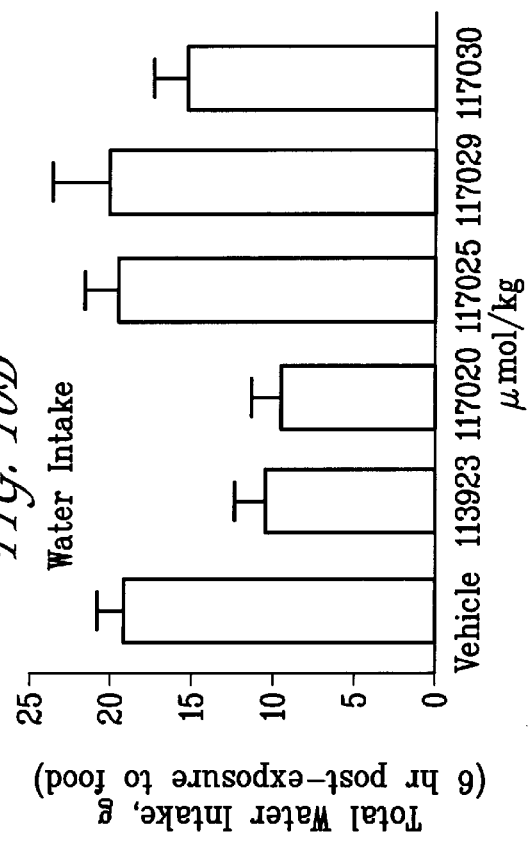

In FIG. 10, rats were deprived 24 hours prior to oral administration of the compound. In this assay, analogs ARE130, ARE135, ARE136, and ARE140, were administered at a dose of 100 μmol/kg. Three analogs, particularly, ARE130, ARE136 and ARE140 evidenced a slow intake of food (e.g., about 1 to 1.5 grams every two hours) over an eight hour period post-administration; while the vehicle rat consumed about 2 to 2.5 grams food every two hours. Similar to the vehicle rat, analog ARE135, an opened ring structure, evidenced that over an eight hour period post-administration the rats increasingly consumed about 2.5 grams every two hours. (See, FIG. 10A). Furthermore, the body weight of the vehicle rat and administered rats with analog ARE135 gained about 19.5 grams. On the other hand, the closed ring structures evidenced a decrease in body weight gain as follows: ARE112-6 grams, ARE130-9 grams, ARE136-11 grams and ARE140-14 grams. See, FIG. 10C.

The treated rats, particularly ARE130 and ARE136, drank less amount of water compared to the vehicle animal, i.e., about 10 grams and 4 grams less, respectively; while analogs ARE135 and ARE140 drank a comparable amount (i.e., about 19 grams). See, FIG. 10B. These data suggests that the closed ring structures, preferably ARE112, ARE130, ARE136 and ARE140; more preferably ARE112 and ARE130; and most preferably ARE112, are specific to the G protein-coupled receptor six.

Table E below lists several $IC_{50}$ values for the analogs of ARE112. $IC_{50}$ values were derived using the GTP Assay as disclosed in Example 4A. At low concentrations of analogs ARE130, ARE136 and ARE140 GPR6 is activated, thus stimulating the conversion of GTP to GDP. This data supports the suggestion that closed ring structures are selective inverse agonists for GPR6.

TABLE E

| Analogs | $IC_{50}$ Values (μM) |
|---|---|
| ARE130 | 022 +/− 022 (3) |
| ARE135 | 100 +/− 137 (2) |
| ARE136 | 0.17 +/− 0.07 (3) |
| ARE140 | 0.17 +/− 0.13 (5) |

Example 7

GPR6 Inverse Agonists

Based upon the patent disclosure and the information provided herein, one of ordinary skill in the art is credited with the ability to directly identify candidate compounds as inverse agonists, agonists and partial agonists to GPR6. Most preferably, these will be small molecule compounds that have not evidenced these characteristics (i.e., selective for GPR6) prior to such direct identification. For agonists, the objective in the screening is to find small molecules that increase the measured signal.

Below, we disclose our most preferred small molecule GPR6 inverse agonists. It is recognized that various stereoisomeric forms of the compounds disclosed herein may exist. It is intended that the present invention include racemates, individual enantiomers, and mixtures thereof.

1. Open Chain Aryl Series

As a first series of GPR6 inverse agonists, disclosed are "open chain aryls" represented structurally as follows (note: if the selection of one or more of $R^8$, $R^9$, $R^{10}$, and $R^{11}$ results in an asymmetric or diastereomeric molecule, then the racemic mixtures, the diastereomeric mixtures and each of the separated (+) and (−) enantiomers or diastereomers are within the scope of the disclosed series, and within the scope of the claims to follow):

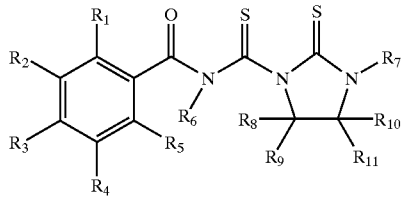

wherein $R^1$, $R^2$, $R^3$, $R^4$, and $R^5$ are each independently selected from the following:

H, F, Cl, Br, I, $R^{12}$, $CF_3$, $CF_2R^{12}$, $CF_2CF_2$, $CCl_3$, $CCl_2R^{12}$, $CCl_2CCl_2R^{12}$, $NR^{13}R^{14}$, $NR^{15}COR^{12}$, $NR^{15}SO_2R^{12}$, $OR^{12}$, $OCF_3$, $OCF_2R^{12}$, $OCF_2CF_2R^{12}$, $OCOR^{12}$, $OSO_2R^{12}$, $OPO(OR^{12})_2$, $SR^{12}$, $SCF_3$, $SCF_2R^{12}$, $SCF_2CF_2R^{12}$, $SCOR^{12}$, $SO_3R^{12}$, $SO_2NR^{13}R^{14}$, $PO(OR^{12})_3$, $PO(OR^{12})_2R^{12}$, $NO_2$, $CN$, $CNR^{15}(NR^{13}R^{14})$, $CNR^{15}(SR^{12})$, $COOR^{12}$, $COSR^{12}$, $CONR^{13}R^{14}$, and wherein any two adjacent positions of $R^1$, $R^2$, $R^3$, $R^4$, and $R^5$ can be joined by a chain selected from CHCHCHCH, $CH_2CH_2CH_2CH_2$, CHCHCH$_2$, $CH_2CH_2CH_2$, $CH_2CH_2$, $SCH_2S$, $SCH_2CH_2S$, $OCH_2O$, and $OCH_2CH_2O$ to form a bi-cyclic structure;

$R^6$ and $R^7$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^8$, $R^9$, $R^{10}$, and $R^{11}$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl andr alkylaryl;

$R^{12}$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $(CH_2)_n NR_{13}R_{14}$, $(CH_2)_mSO_3H$, and $(CH_2)_mCO_2H$ wherein n is 2 through 6 and m is 1 through 6;

$R^{13}$ and $R^{14}$ are each independently selected from H, $C_{1-8}$ straight chain alkyl, branched alkyl, $C_{2-8}$ alkenyl, cycloalkyl, alkylcycloalkyl, cycloalkylalkyl, aryl, and $CH_2$aryl, wherein each said aryl group or said aryl portion of said $CH_2$aryl group may be optionally substituted by up to four substituents in any position on said aryl, each said position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and/or $R^{14}$ contain an aryl ring, said aryl ring being substituted at two adjacent positions on said aryl ring, then said two adjacent positions can be joined by a chain selected from CHCHCHCH, $CH_2CH_2CH_2CH_2$, CHCHCH$_2$, $CH_2CH_2CH_2$, $CH_2CH_2$, $SCH_2S$, $SCH_2CH_2S$, $OCH_2O$, and $OCH_2CH_2O$ to form a bi-cyclic structure; or $R^{13}$ and $R^{14}$ may form part of a 5, 6 or 7 membered cyclic structure which may be either saturated or unsaturated and that may contain up to four heteroatoms selected from O, N and S and said cyclic structure may be optionally substituted by up to four substituents in any position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$; or wherein when $R^{13}$ and $R^{14}$ form an aryl ring substituted at two adjacent positions on said aryl ring, then said two adjacent positions can be joined by a chain selected from CHCHCHCH, $CH_2CH_2CH_2CH_2$, CHCHCH$_2$, $CH_2CH_2CH_2$, $CH_2CH_2$, $SCH_2S$, $SCH_2CH_2S$, $OCH_2O$, or $OCH_2CH_2O$ to form a bi-cyclic structure; and $R^{15}$ is selected from H, $C_{1-8}$ straight chain alkyl, branched alkyl, $C_{3-8}$ cycloalkyl, $C_{4-9}$ alkylcycloalkyl or cycloalkylalkyl, and $C_{2-8}$ alkenyl.

The following provisos, preferentially noted, may apply whereby when $R^6$, $R^7$, $R^8$, $R^9$, $R^{10}$, and $R^{11}$ are all H, then at least one of $R^1$, $R^2$, $R^3$ and $R^4$ is other than H; and when $R^1$, $R^2$, $R^4$, $R^5$, $R^6$, $R^7$, $R^8$, $R^9$, $R^{10}$, and $R^{11}$ are all H, then $R^3$ is not Cl, $CH_3$, or $OCH_3$; and when $R^1$, $R^5$, $R^6$, $R^7$, $R^8$, $R^9$, $R^{10}$, and $R^{11}$ are all H, then $R^2$, $R^3$, and $R^4$ are not $OCH_3$.

An "aryl moiety" can be a 5 or 6 membered aromatic heterocyclic ring (containing up to four hetero atoms independently selected from N, O, or S) or a six membered aromatic non-heterocyclic ring or a polycycle;

Examples of suitable $C_{1-8}$ alkyl groups include, but art not limited to methyl, ethyl, n-propyl, i-propyl, n-butyl, and t-butyl.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Further disclosed is a method of modulating the GPR6 receptor by contacting said receptor with a small molecule structurally represented as follows:

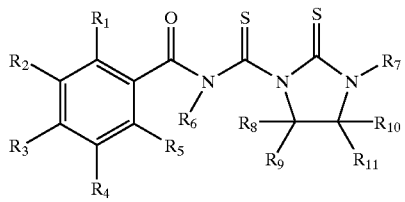

wherein $R^1$, $R^2$, $R^3$, $R^4$, and $R^5$ are each independently selected from the following:

H, F, Cl, Br, I, $R^{12}$, $CF_3$, $CF_2R^{12}$, $CF_2CF_2$, $CCl_3$, $CCl_2R^{12}$, $CCl_2CCl_2R^{12}$, $NR^{13}R^{14}$, $NR^{15}COR^{12}$, $NR^{15}SO_2R^{12}$, $OR^{12}$, $OCF_3$, $OCF_2R^{12}$, $OCF_2CF_2R^{12}$, $OCOR^{12}$, $OSO_2R^{12}$, $OPO(OR^{12})_2$, $SR^{12}$, $SCF_3$, $SCF_2R^{12}$, $SCF_2CF_2R^{12}$, $SCOR^{12}$, $SO_3R^{12}$, $SO_2NR^{13}R^{14}$, $PO(OR^{12})_3$, $PO(OR^{12})_2R^{12}$, $NO_2$, CN, $CNR^{15}(NR^{13}R^{14})$, $CNR^{15}(SR^{12})$, $COOR^{12}$, $COSR^{12}$, $CONR^{13}R^{14}$, and wherein any two adjacent positions of $R^1$, $R^2$, $R^3$, $R^4$, and $R^5$ can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, and $OCH_2CH_2O$ to form a bi-cyclic structure;

$R^6$ and $R^7$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^8$, $R^9$, $R^{10}$, and $R^{11}$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl andr alkylaryl;

$R^{12}$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $(CH_2)_n NR_{13}R_{14}$, $(CH_2)_m SO_3H$, and $(CH_2)_m CO_2H$ wherein n is 2 through 6 and m is 1 through 6;

$R^{13}$ and $R^{14}$ are each independently selected from H, $C_{1-8}$ straight chain alkyl, branched alkyl, $C_{2-8}$ alkenyl, cycloalkyl, alkylcycloalkyl, cycloalkylalkyl, aryl, and $CH_2$aryl, wherein each said aryl group or said aryl portion of said $CH_2$aryl group may be optionally substituted by up to four substituents in any position on said aryl, each said position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and/or $R^{14}$ contain an aryl ring, said aryl ring being substituted at two adjacent positions on said aryl ring, then said two adjacent positions can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, and $OCH_2CH_2O$ to form a bi-cyclic structure; or $R^{13}$ and $R^{14}$ may form part of a 5, 6 or 7 membered cyclic structure which may be either saturated or unsaturated and that may contain up to four heteroatoms selected from O, N and S and said cyclic structure may be optionally substituted by up to four substituents in any position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_{47}$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$; or wherein when $R^{13}$ and $R^{14}$ form an aryl ring substituted at two adjacent positions on said aryl ring, then said two adjacent positions can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, or $OCH_2CH_2O$ to form a bi-cyclic structure; and $R^{15}$ is selected from H, $C_{1-8}$ straight chain alkyl, branched alkyl, $C_{3-8}$ cycloalkyl, $C_{4-9}$ alkylcycloalkyl or cycloalkylalkyl, and $C_{2-8}$ alkenyl.

2. Closed Chain Aryl Series

A second series of GPR6 inverse agonists are "closed chain aryls" represented structurally as follows:

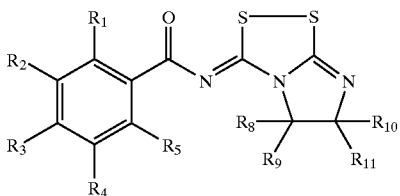

wherein

R$^1$, R$^2$, R$^3$, R$^4$, and R$^5$ are each independently selected from the following:

H, F, Cl, Br, I, R$^{12}$, CF$_3$, CF$_2$R$^{12}$, CF$_2$CF$_2$, CCl$_3$, CCl$_2$R$^{12}$, CCl$_2$CCl$_2$R$^{12}$, NR$^{13}$R$^{14}$, NR$^{15}$COR$^{12}$, NR$^{15}$SO$_2$R$^{12}$, OR$^{12}$, OCF$_3$, OCF$_2$R$^{12}$, OCF$_2$CF$_2$R$^{12}$, OCOR$^{12}$, OSO$_2$R$^{12}$, OPO(OR$^{12}$)$_2$, SR$^{12}$, SCF$_3$, SCF$_2$R$^{12}$, SCF$_2$CF$_2$R$^{12}$, SCOR$^{12}$, SO$_3$R$^{12}$, SO$_2$NR$^{13}$R$^{14}$, PO(OR$^{12}$)$_3$, PO(OR$^{12}$)$_2$R$^{12}$, NO$_2$, CN, CNR$^{15}$(NR$^{13}$R$^{14}$), CNR$^{15}$(SR$^{12}$), COOR$^{12}$, COSR$^{12}$R$^{14}$, and wherein any two adjacent positions of R$^1$, R$^2$, R$^3$, R$^4$, and R$^5$ can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure;

R$^8$, R$^9$, R$^{10}$, and R$^{11}$ are each independently selected from H, C$_{1-8}$ straight chain alkyl, branched alkyl, C$_{3-8}$ cycloalkyl, C$_{4-9}$ alkylcycloalkyl or cycloalkylalkyl, C$_{2-8}$ alkenyl, aryl and alkylaryl;

R$^{12}$ is selected from H, C$_{1-8}$ straight chain alkyl, branched alkyl, C$_{3-8}$ cycloalkyl, C$_{4-9}$ alkylcycloalkyl or cycloalkylalkyl, C$_{2-8}$ alkenyl, aryl, alkylaryl, (CH$_2$)$_n$NR$_{13}$R$_{14}$, (CH$_2$)$_m$SO$_3$H, and (CH$_2$)$_m$CO$_2$H wherein n is 2 through 6 and m is 1 through 6;

R$^{13}$ and R$^{14}$ are each independently selected from H, C$_{1-8}$ straight, chain alkyl, branched alkyl, C$_{2-8}$ alkenyl, cycloalkyl, alkylcycloalkyl, cycloalkylalkyl, aryl and CH$_2$aryl, wherein each said aryl group or said aryl portion of said CH$_2$aryl group may be optionally substituted by up to four substituents in any position independently selected from:

F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$, SCF$_3$, SCOCH$_3$, SCOC$_2$H$_5$, SCOC$_3$H$_7$, SCOC4H$_9$, SO$_3$CH$_3$, SO$_3$C$_2$H$_5$, SO$_3$C$_3$H$_7$, SO$_3$C$_4$H$_9$, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and wherein when R$^{13}$ and/or R$^{14}$ contain an aryl ring substituted at two adjacent positions on said aryl ring, then said two adjacent positions can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure; or R$^{13}$ and R$^{14}$ may form part of a 5, 6 or 7 membered saturated cyclic structure or 5,6 or 7 membered unsaturated cyclic structure, each such structure optionally containing up to four heteroatoms selected from O, N and S and wherein each said cyclic structure may be optionally substituted by up to four substituents in any position, each position independently selected from:

F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$, SCF$_3$, SCOCH$_3$, SCOC$_2$H$_5$, SCOC$_3$H$_7$, SCOC4H$_9$, SO$_3$CH$_3$, SO$_3$C$_2$H$_5$, SO$_3$C$_3$H$_7$, SO$_3$C$_4$H$_9$, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and wherein when R$^{13}$ and R$^{14}$ form an aryl ring substituted at two adjacent positions on said aryl ring, then said two adjacent positions can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure; and R$^{15}$ is selected from H, C$_{1-8}$ straight chain alkyl, branched alkyl, C$_{3-8}$ cycloalkyl, C$_{4-9}$ alkylcycloalkyl or cycloalkylalkyl, and C$_{2-8}$ alkenyl;

The following provisos, preferentially noted, may apply whereby when R$^6$, R$^7$, R$^8$, R$^9$, R$^{10}$, and R$^{11}$ are all H, then at least one of R$^1$, R$^2$, R$^3$ and R$^4$ is other than H; and when R$^1$, R$^2$, R$^4$, R$^5$, R$^6$, R$^7$, R$^8$, R$^9$, R$^{10}$, and R$^{11}$ are all H, then R$^3$ is not Cl, CH$_3$, or OCH$_3$; and when R$^1$, R$^5$, R$^6$, R$^7$, R$^8$, R$^9$, R$^{10}$, and R$^{11}$ are all H, then R$^2$, R$^3$, and R$^4$ are not OCH$_3$.

An "aryl moiety" can be a 5 or 6 membered aromatic heterocyclic ring (containing up to 4 hetero atoms independently selected from N, O, or S) or a 6 membered aromatic non-heterocyclic ring or a polycycle.

Examples of suitable C$_{1-8}$ alkyl groups include but art not limited to methyl, ethyl, n-propyl, i-propyl, n-butyl, and t-butyl.

Examples of 5 or 6 membered ring moieties include, but are not restricted to, phenyl, ffiranyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Further disclosed is a method of modulating the GPR6 receptor by contacting said receptor with a small molecule structurally represented as follows:

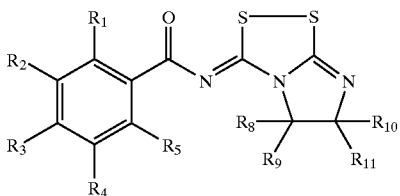

wherein
R$^1$, R$^2$, R$^3$, R$^4$, and R$^5$ are each independently selected from the following:
H, F, Cl, Br, I, R$^{12}$, CF$_3$, CF$_2$R$^{12}$, CF$_2$CF$_2$, CCl$_3$, CCl$_2$R$^{12}$, CCl$_2$CCl$_2$R$^{12}$, NR$^{12}$, NR$^{13}$R$^{14}$, NR$^{15}$COR$^{12}$, NR$^{15}$SO$_2$R$^{12}$, OR$^{12}$, OCF$_3$, OCF$_2$R$^{12}$, OCF$_2$R$^{12}$, OCOR$^{12}$, OSO$_2$R$^{12}$, OPO(OR$^{12}$)$_2$, SR$^{12}$, SCF$_3$, SCF$_2$R$^{12}$, SCF$_2$CF$_2$R$^{12}$, SCOR$^{12}$, SO$_3$R$^{12}$, SO$_2$NR$^{13}$R$^{14}$, PO(OR$^{12}$)$_3$, PO(OR$^{12}$)$_2$R$^{12}$, NO$_2$, CN, CNR$^{15}$(NR$^{13}$R$^{14}$), CNR$^{15}$(SR$^{12}$), COOR$^{12}$, COSR$^{12}$, CONR$^{13}$R$^{14}$, and wherein any two adjacent positions of R$^1$, R$^2$, R$^3$, R$^4$, and R$^5$ can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure;

R$^8$, R$^9$, R$^{10}$, and R$^{11}$ are each independently selected from H, C$_{1-8}$ straight chain alkyl, branched alkyl, C$_{3-8}$ cycloalkyl, C$_{4-9}$ alkylcycloalkyl or cycloalkylalkyl, C$_{2-8}$ alkenyl, aryl and alkylaryl;

R$^{12}$ is selected from H, C$_{1-8}$ straight chain alkyl, branched alkyl, C$_{3-8}$ cycloalkyl, C$_{4-9}$ alkylcycloalkyl or cycloalkylalkyl, C$_{2-8}$ alkenyl, aryl, alkylaryl, (CH$_2$)$_n$NR$_{13}$R$_{14}$, (CH$_2$)$_m$SO$_3$H, and (CH$_2$)$_m$CO$_2$H wherein n is 2 through 6 and m is 1 through 6;

R$^{13}$ and R$^{14}$ are each independently selected from H, C$_{1-8}$ straight chain alkyl, branched alkyl, C$_{2-8}$ alkenyl, cycloalkyl, alkylcycloalkyl, cycloalkylalkyl, aryl and CH$_2$aryl, wherein each said aryl group or said aryl portion of said CH$_2$aryl group may be optionally substituted by up to four substituents in any position independently selected from:
F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$, H$_7$, SC$_4$H$_9$, SC$_5$H$_9$, SC$_5$H$_{11}$, SC$_6$H$_{11}$, SC$_6$H$_{13}$,, SCF$_3$, SCOCH$_3$, SCOC$_2$H$_5$, SCOC$_3$H$_7$, SCOC$_4$H$_9$, SO$_3$CH$_3$, SO$_3$C$_2$H$_5$, SO$_3$C$_3$H$_7$, SO$_3$C$_4$H$_9$, SO$_2$NH$_2$, SO$_2$NHCH$_3$, SO$_2$N(CH$_3$)$_2$, SO$_2$NCH$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and wherein when R$^{13}$ and/or R$^{14}$ contain an aryl ring substituted at two adjacent positions on said aryl ring, then said two adjacent positions can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure; or R$^{13}$ and R$^{14}$ may form part of a 5, 6 or 7 membered saturated cyclic structure or 5,6 or 7 membered unsaturated cyclic structure, each such structure optionally containing up to four heteroatoms selected from O, N and S and wherein each said cyclic structure may be optionally substituted by up to four substituents in any position, each position independently selected from:
F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H13, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$,, SCF$_3$, SCOCH$_3$, SCOC$_2$H$_5$, SCOC$_3$H$_7$, SCOC$_4$H$_9$, SO$_3$CH$_3$, SO$_3$C$_2$H$_5$, SO$_3$C$_3$H$_7$, SO$_3$C$_4$H$_9$, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and wherein when R$^{13}$ and R$^{14}$ form an aryl ring substituted at two adjacent positions on said aryl ring, then said two adjacent positions can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure; and R$^{15}$ is selected from H, C$_{1-8}$ straight chain alkyl, branched alkyl, C$_{3-8}$ cycloalkyl, C$_{4-9}$ alkylcycloalkyl or cycloalkylalkyl, andC$_{2-8}$ alkenyl;

3. Open Chain 6 Membered Heteroaryl Series

A third series of GPR6 inverse agonists are "open chain 6 membered heteroaryls" represented structurally as follows:

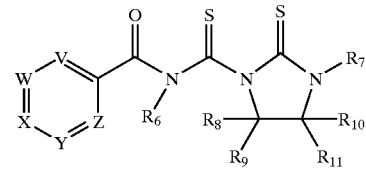

wherein
at least one of V, W, X, Y and Z is selected from N and each of V, W, X, V, and Z that is/are not N are independently selected from CR$^1$, CR$^2$, CR$^3$, CR$^4$, and CR$^5$, with the proviso that at least two of V, W, X, V and Z are other than N;

R$^1$, R$^2$, R$^3$, R$^4$, and R$^5$ are each independently selected from the following:
H, F, Cl, Br, I, R$^{12}$, CF$_3$, CF$_2$R$^{12}$, CF$_2$CF$_2$, CCl$_3$, CCl$_2$R$^{12}$, CCl$_2$CCl$_2$R$^{12}$, NR$^{13}$R$^{14}$, NR$^{15}$COR$^{12}$, NR$^{15}$SO$_2$R$^{12}$, OR$^{12}$, OCF$_3$, OCF$_2$R$^{12}$, OCF$_2$CF$_2$R$^{12}$, OCOR$^{12}$, OSO$_2$R$^{12}$, OPO(OR$^{12}$)$_2$, SR$^{12}$, SCF$_3$, SCF$_2$R$^{12}$, SCF$_2$CF$_2$R$^{12}$, SCOR$^{12}$, SO$_3$R$^{12}$, SO$_2$NR$^{13}$R$^{14}$, PO(OR$^{12}$)$_3$, PO(OR$^{12}$)$_2$R$^{12}$, NO$_2$, CN, CNR$^{15}$(NR$^{13}$R$^{14}$), CNR$^{15}$(SR$^{12}$), COOR$^{12}$COSR$^{12}$, CONR$^{13}$R$^{14}$, and wherein any two adjacent positions of $R^1$, $R^2$, $R^3$, $R^4$, and $R^5$ can be joined by a chain selected from CHCHCHCH, $CH_2CH_2CH_2CH_2$, CHCHCH$_2$, $CH_2CH_2CH_2$, $CH_2CH_2$, $SCH_2S$, $SCH_2CH_2S$, $OCH_2O$, and $OCH_2CH_2O$ to form a bi-cyclic structure;

$R^8$, $R^9$, $R^{10}$, and $R^{11}$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^{12}$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $(CH_2)_n NR_{13}R_{14}$, $(CH_2)_m SO_3H$, and $(CH_2)_m CO_2H$, wherein n is 2 through 6 and m is 1 through 6;

$R^{13}$ and $R^{14}$ are each independently selected from H, $C_{1-8}$ straight chain alkyl, branched alkyl, $C_{2-8}$ alkenyl, cycloalkyl, alkylcycloalkyl, cycloalkylalkyl, aryl and $CH_2$aryl, wherein each said aryl group or said aryl portion of said $CH_2$aryl group may be optionally substituted by up to four substituents in any position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and/or $R^{14}$ contain an aryl ring substituted at two adjacent positions on said aryl ring, then said two adjacent positions can be joined by a chain selected from CHCHCHCH, $CH_2CH_2CH_2CH_2$, CHCHCH$_2$, $CH_2CH_2CH_2$, $CH_2CH_2$, $SCH_2S$, $SCH_2CH_2S$, $OCH_2O$, or $OCH_2CH_2O$ to form a bi-cyclic structure; or $R^{13}$ and $R^{14}$ form part of a 5, 6 or 7 membered saturated cyclic structure or 5,6 or 7 membered unsaturated cyclic structure, each such structure optionally containing up to four heteroatoms selected from O, N and S and wherein each said cyclic structure may be optionally substituted by up to four substituents in any position, each position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$,, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and $R^{14}$ form an aryl ring substituted at two adjacent positions on said aryl ring, then said two adjacent positions can be joined by a chain selected from CHCHCHCH, $CH_2CH_2CH_2CH_2$, CHCHCH$_2$, $CH_2CH_2CH_2$, $CH_2CH_2$, $SCH_2S$, $SCH_2CH_2S$, $OCH_2O$, or $OCH_2CH_2O$ to form a bi-cyclic structure; and $R^{15}$ is selected from H, $C_{1-8}$ straight chain alkyl, branched alkyl, $C_{3-8}$ cycloalkyl, $C_{4-9}$ alkylcycloalkyl or cycloalkylalkyl, and $C_{2-8}$ alkenyl;

An aryl moiety can be a 5 or 6 membered aromatic heterocyclic ring (containing up to 4 hetero atoms independently selected from N, O, or S) or a 6 membered aromatic non-heterocyclic ring or a polycycle;

Examples of suitable $C_{1-8}$ alkyl groups include but art not limited to methyl, ethyl, n-propyl, i-propyl, n-butyl, and t-butyl.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Further disclosed is a method of modulating the GPR6 receptor by contacting said receptor with a small molecule structurally represented by the foregoing open chain 6 membered heteroaryl series.

4. Closed Chain 6 Membered Heteroaryl Series

A fourth series of GPR6 inverse agonists are "closed chain 6 membered heteroaryls" represented structurally as follows:

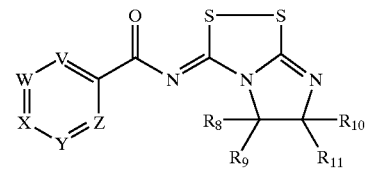

wherein
at least one of V, W, X, Y and Z is selected from N and each of V, W, X, Y, and Z that is/are not N are independently selected from $CR^1$, $CR^2$, $CR^3$, $CR^4$, and $CR^5$, with the proviso that at least two of V, W, X, Y and Z are other than N;

$R^1$, $R^2$, $R^3$, $R^4$, and $R^5$ are each independently selected from the following:

H, F, Cl, Br, I, $R^{12}$, $CF_3$, $CF_2R^{12}$, $CF_2CF_2$, $CCl_3$, $CCl_2R^{12}$, $CCl_2CCl_2R^{12}$, $NR^{13}R^{14}$, $NR^{15}COR^{12}$, $NR^{15}SO_2R^{12}$, $OR^{12}$, $OCF_3$, $OCF_2R^{12}$, $OCF_2CF_2R^{12}$, $OCOR^{12}$, $OSO_2R^{12}$, $OPO(OR^{12})_2$, $SR^{12}$, $SCF_3$, $SCF_2R^{12}$, $SCF_2CF_2R^{12}$, $SCOR^{12}$, $SO_3R^{12}$, $SO_2NR^{13}R^{14}$, $PO(OR^{12})_3$, $PO(OR^{12})_2R^{12}$, $NO_2$, CN, $CNR^{15}(NR^{13}R^{14})$, $CNR^{15}(SR^{12})$, $COOR^{12}COSR^{12}$, $CONR^{13}R^{14}$, and wherein any two adjacent positions of $R^1$, $R^2$, $R^3$, $R^4$, and $R^5$ can be joined by a chain selected from CHCHCHCH, $CH_2CH_2CH_2CH_2$, CHCHCH$_2$, $CH_2CH_2CH_2$, $CH_2CH_2$, SCH$_2$S, SCH$_2$CH$_2$S, OCH$_2$O, and OCH$_2$CH$_2$O to form a bi-cyclic structure;

$R^8$, $R^9$, $R^{10}$, and $R^{11}$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^{12}$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $(CH_2)_n NR_{13}R_{14}$, $(CH_2)_m SO_3H$, and $(CH_2)_m CO_2H$, wherein n is 2 through 6 and m is 1 through 6;

$R^{13}$ and $R^{14}$ are each independently selected from H, $C_{1-8}$ straight chain alkyl, branched alkyl, $C_{2-8}$ alkenyl, cycloalkyl, alkylcycloalkyl, cycloalkylalkyl, aryl and CH$_2$aryl, wherein each said aryl group or said aryl portion of said CH$_2$aryl group may be optionally substituted by up to four substituents in any position independently selected from:

F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$, SCF$_3$, SCOCH$_3$, SCOC$_2$H$_5$, SCOC$_3$H$_7$, SCOC$_4$H$_9$, SO$_3$CH$_3$, SO$_3$C$_2$H$_5$, SO$_3$C$_3$H$_7$, SO$_3$C$_4$H$_9$, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and wherein when $R^{13}$ and/or $R^{14}$ contain an aryl ring substituted at two adjacent positions on said aryl ring, then said two adjacent positions can be joined by a chain selected from CHCHCHCH, $CH_2CH_2CH_2CH_2$, CHCHCH$_2$, $CH_2CH_2CH_2$, $CH_2CH_2$, SCH$_2$S, SCH$_2$CH$_2$S, OCH$_2$O, or OCH$_2$CH$_2$O to form a bi-cyclic structure; or $R^{13}$ and $R^{14}$ form part of a 5, 6 or 7 membered saturated cyclic structure or 5,6 or 7 membered unsaturated cyclic structure, each such structure optionally containing up to four heteroatoms selected from O, N and S and wherein each said cyclic structure may be optionally substituted by up to four substituents in any position, each position independently selected from:

F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$, SCF$_3$, SCOCH$_3$, SCOC$_2$H$_5$, SCOC$_3$H$_7$, SCOC$_4$H$_9$, SO$_3$CH$_3$, SO$_3$C$_2$H$_5$, SO$_3$C$_3$H$_7$, SO$_3$C$_4$H$_9$, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and wherein when $R^{13}$ and $R^{14}$ form an aryl ring substituted at two adjacent positions on said aryl ring, then said two adjacent positions can be joined by a chain selected from CHCHCHCH, $CH_2CH_2CH_2CH_2$, CHCHCH$_2$, $CH_2CH_2CH_2$, $CH_2CH_2$, SCH$_2$S, SCH$_2$CH$_2$S, OCH$_2$O, or OCH$_2$CH$_2$O to form a bi-cyclic structure; and $R^{15}$ is selected from H, $C_{1-8}$ straight chain alkyl, branched alkyl, $C_{3-8}$ cycloalkyl, $C_{4-9}$ alkylcycloalkyl or cycloalkylalkyl, and $C_{2-8}$ alkenyl;

An aryl moiety can be a 5 or 6 membered aromatic heterocyclic ring (containing up to 4 hetero atoms independently selected from N, O, or S) or a 6 membered aromatic non-heterocyclic ring or a polycycle;

Examples of suitable $C_{1-8}$ alkyl groups include but art not limited to methyl, ethyl, n-propyl, i-propyl, n-butyl, and t-butyl;

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Further disclosed is a method of modulating the GPR6 receptor by contacting said receptor with a small molecule structurally represented by the foregoing closed chain 6 membered heteroaryl series.

5. Open Chain 5 Membered Heteroaryl (Sub-series a)

A fifth series of GPR6 inverse agonists are "open chain 5 membered heteraryls" represented structurally as follows:

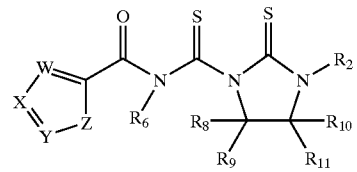

wherein

Z is selected from NR$^4$, O and S;

W, X, or Y are independently selected from N, CR$^1$, CR$^2$, and CR$^3$, with the provisio that when Z is O and Y is N, then W is CR$^1$ and X is CR$^2$;

$R^1$, $R^2$, and $R^3$ are each independently selected from the following:

H, F, Cl, Br, I, $R^{12}$, CF$_3$, CF$_2R^{12}$, CF$_2$CF$_2$, CCl$_3$, CCl$_2R^{12}$, CCl$_2$CCl$_2R^{12}$, NR$^{13}$R$^{14}$, NR$^{15}$COR$^{12}$, NR$^{15}$SO$_2$R$^{12}$, OR$^{12}$, OCF$_3$, OCF$_2$R$^{12}$, OCF$_2$CF$_2$R$^{12}$, OCOR$^{12}$, OSO$_2$R$^{12}$, OPO(OR$^{12}$)$_2$, SR$^{12}$, SCF$_3$, SCF$_2R^{12}$, SCF$_2$CF$_2R^{12}$, SCOR$^{12}$, SO$_3R^{12}$, SO$_2$NR$^{13}$R$^{14}$, PO(OR$^{12}$)$_3$, PO(OR$^{12}$)$_2R^{12}$, NO$_2$, CN, CNR$^{15}$(NR$^{13}$R$^{14}$), CNR$^{15}$(SR$^{12}$), COOR$^{12}$, COSR$^{12}$, CONR$^{13}$R$^{14}$, and wherein any two adjacent positions of $R^1$, $R^2$, $R^3$, $R^4$, and $R^5$ can be joined by a chain selected from CHCHCHCH, $CH_2CH_2CH_2CH_2$, CHCHCH$_2$, $CH_2CH_2CH_2$, $CH_2CH_2$, SCH$_2$S, SCH$_2$CH$_2$S, OCH$_2$O, and OCH$_2$CH$_2$O to form a bi-cyclic structure;

$R^4$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $COR^5$, $CSR^5$, and $SO_2R^5$;

$R^5$, $R^6$ and $R^7$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^6$ and $R^7$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl $R^8$, $R^9$, $R^{10}$, and $R^{11}$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^{12}$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $(CH_2)_n NR_{13}R_{14}$, $(CH_2)_m SO_3H$, and $(CH_2)_m CO_2H$, wherein n is 2 through 6 and m is 1 through 6;

$R^{13}$ and $R^{14}$ are each independently selected from H, $C_{1-8}$ straight chain alkyl, branched alkyl, $C_{2-8}$ alkenyl or cycloalkyl, or alkylcycloalkyl, cycloalkylalkyl, or aryl and $CH_2$aryl, wherein each said aryl group or said aryl portion of said $CH_2$aryl group may be. optionally substituted by up to four substituents in any position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$,, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and/or $R^{14}$ contain an aryl ring substituted at two adjacent positions on said aryl ring, then said two adjacent positions can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, or $OCH_2CH_2O$ to form a bi-cyclic structure; or $R^{13}$ and $R^{14}$ form part of a 5, 6 or 7 membered saturated cyclic structure or 5,6 or 7 membered unsaturated cyclic structure, each such structure optionally containing up to four heteroatoms selected from O, N and S and wherein each said cyclic structure may be optionally substituted by up to four substituents in any position, each position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$,, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and $R^{14}$ form an aryl ring substituted at two adjacent positions on said aryl ring, then said two adjacent positions can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, and $OCH_2CH_2O$ to form a bi-cyclic structure; and $R^{15}$ is selected from H, $C_{1-8}$ straight chain alkyl, branched alkyl, $C_{3-8}$ cycloalkyl, $C_{4-9}$ alkylcycloalkyl or cycloalkylalkyl, and $C_{2-8}$ alkenyl.

An aryl moiety can be a 5 or 6 membered aromatic heterocyclic ring (containing up to 4 hetero atoms independently selected from N, O, or S) or a 6 membered aromatic non-heterocyclic ring or a polycycle;

Examples of suitable $C_{1-8}$ alkyl groups include but art not limited to methyl, ethyl, n-propyl, i-propyl, n-butyl, and t-butyl.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Further disclosed is a method of modulating the GPR6 receptor by contacting said receptor with a small molecule structurally represented by the foregoing open chain 5 membered heteroaryl series.

6. Closed Chain 5 Membered Heteroaryl (Sub-series a)

As a sixth series of GPR6 inverse agonists, disclosed are "closed chain 5 membered heteroaryl sub-series a", represented structurally as follows:

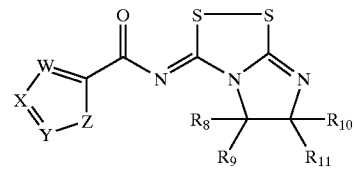

wherein

Z is selected from $NR^4$, O and S;

W, X, or Y are independently selected from N, $CR^1$, $CR^2$, and $CR^3$, with the provisio that when Z is O and Y is N, then W is $CR^1$ and X is $CR^2$;

$R^1$, $R^2$, and $R^3$ are each independently selected from the following:

H, F, Cl, Br, I, $R^{12}$, $CF_3$, $CF_2R^{12}$, $CF_2CF_2$, $CCl_3$, $CCl_2R^{12}$, $CCl_2CCl_2R^{12}$, $NR^{13}R^{14}$, $NR^{15}COR^{12}$, $NR^{15}SO_2R^{12}$, $OR^{12}$, $OCF_3$, $OCF_2R^{12}$, $OCF_2CF_2R^{12}$, $OCOR^{12}$, $OSO_2R^{12}$, $OPO(OR^{12})_2$, $SR^{12}$, $SCF_3$, $SCF_2R^{12}$, $SCF_2CF_2R^{12}$, $SCOR^{12}$, $SO_3R^{12}$, $SO_2NR^{13}R^{14}$, $PO(OR^{12})_3$, $PO(OR^{12})_2R^{12}$, $NO_2$, $CN$, $CNR^{15}(NR^{13}R^{14})$, $CNR^{15}(SR^{12})$, $COOR^{12}$, $COSR^{12}$, $CONR^{13}R^{14}$, and wherein any two adjacent positions of $R^1$, $R^2$, $R^3$, $R^4$, and $R^5$ can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, and $OCH_2CH_2O$ to form a bi-cyclic structure;

$R^4$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $COR^5$, $CSR^5$, and $SO_2R^5$;

$R^5$, $R^6$ and $R^7$ are each independently selected from H, $C_{1-8}$ straight chain aLkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^6$ and $R^7$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl $R^8$, $R^9$, $R^{10}$, and $R^{11}$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^{12}$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $(CH_2)_nNR_{13}R_{14}$, $(CH_2)_mSO_3H$, $(CH_2)_mCO_2H$ wherein n is 2 through 6 or m is 1 through 6;

$R^{13}$ and $R^{14}$ are each independently selected from H, $C_{1-8}$ straight chain alkyl, branched alkyl, $C_{2-8}$ alkenyl or cycloalkyl, or alkylcycloalkyl, or cycloalkylalkyl, or aryl or $CH_2$aryl, wherein each said aryl group or said aryl portion of said $CH_2$aryl group may be optionally substituted by up to four substituents in any position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$,, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and/or $R^{14}$ contain an aryl ring substituted at two adjacent positions on said aryl ring, then said two adjacent positions can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, or $OCH_2CH_2O$ to form a bi-cyclic structure; or $R^{13}$ and $R^{14}$ form part of a 5, 6 or 7 membered saturated cyclic structure or 5,6 or 7 membered unsaturated cyclic structure, each such structure optionally containing up to four heteroatoms selected from O, N and S and wherein each said cyclic structure may be optionally substituted by up to four substituents in any position, each position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and $R^{14}$ form an aryl ring substituted at two adjacent positions on said aryl ring, then said two adjacent positions can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, or $OCH_2CH_2O$ to form a bi-cyclic structure; and $R^{15}$ is selected from H, $C_{1-8}$ straight chain alkyl, branched alkyl, $C_{3-8}$ cycloalkyl, $C_{4-9}$ alkylcycloalkyl or cycloalkylalkyl, and $C_{2-8}$ alkenyl.

An aryl moiety can be a 5 or 6 membered aromatic heterocyclic ring (containing up to 4 hetero atoms independently selected from N, O, or S) or a 6 membered aromatic non-heterocyclic ring or a polycycle;

Examples of suitable $C_{1-8}$ alkyl groups include but art not limited to methyl, ethyl, n-propyl, i-propyl, n-butyl, and t-butyl.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Further disclosed is a method of modulating the GPR6 receptor by contacting said receptor with a small molecule structurally represented by the foregoing closed chain 5 membered heteroaryl series.

7. Open Chain 5 Membered Heteroaryl (Sub-series b)

As a seventh series of GPR6 inverse agonist, disclosed are "open chain 5 membered heteroaryl sub-series b" represented structurally as follows:

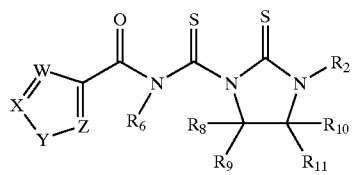

wherein

Y is selected from NR$^4$, O or S;

W, X, or Z are each independently selected from N or CR$^1$, CR$^2$, or CR$^3$, with the proviso that when Y is O and Z is N, then W is CR$^1$ and X is CR$^2$;

R$^1$, R$^2$, and R$^3$ are each independently selected from the following:

H, F, Cl, Br, I, R$^{12}$, CF$_3$, CF$_2$R$^{12}$, CF$_2$CF$_2$, CCl$_3$, CCl$_2$R$^{12}$, CCl$_2$CCl$_2$R$^{12}$, NR$^{13}$R$^{14}$, NR$^{15}$COR$^{12}$, NR$^{15}$SO$_2$R$^{12}$, OR$^{12}$, OCF$_3$, OCF$_2$R$^{12}$, OCF$_2$CF$_2$R$^{12}$, OCOR$^{12}$, OSO$_2$R$^{12}$, OPO(OR$^{12}$)$_2$, SR$^{12}$, SCF$_3$, SCF$_2$R$^{12}$, SCF$_2$CF$_2$R$^{12}$, SCOR$^{12}$, SO$_3$R$^{12}$, SO$_2$NR$^{13}$R$^{14}$, PO(OR$^{12}$)$_3$, PO(OR$^{12}$)$_2$R$^{12}$, NO$_2$, CN, CNR$^{15}$(NR$^{13}$R$^{14}$), CNR$^{15}$(SR$^{12}$), COOR$^{12}$, COSR$^{12}$, CONR$^{13}$R$^{14}$, and wherein any two adjacent positions of R$^1$, R$^2$, R$^3$, R$^4$, and R$^5$ can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure;

R$^4$ is H, C$_{1-8}$ straight chain alkyl, branched alkyl, C$_{3-8}$ cycloalkyl, C$_{4-9}$ alkylcycloalkyl or cycloalkylalkyl, C$_{2-8}$ alkenyl, aryl, alkylaryl, COR$^5$, CSR$^5$, and SO$_2$R$^5$;

R$^5$, R$^6$ and R$^7$ are each independently selected from H, C$_{1-8}$ straight chain alkyl, branched alkyl, C$_{3-8}$ cycloalkyl, C$_{4-9}$ alkylcycloalkyl or cycloalkylalkyl, C$_{2-8}$ alkenyl, aryl and alkylaryl;

R$^6$ and R$^7$ are each independently selected from H, C$_{1-8}$ straight chain alkyl, branched alkyl, C$_{3-8}$ cycloalkyl, C$_{4-9}$ alkylcycloalkyl or cycloalkylalkyl, C$_{2-8}$ alkenyl, aryl and alkylaryl R$^8$, R$^9$, R$^{10}$, and R$^{11}$ are each independently selected from H, C$_{1-8}$ straight chain alkyl, branched aikyl, C$_{3-8}$ cycloalkyl, C$_{4-9}$ alkylcycloalkyl or cycloalkylalkyl, C$_{2-8}$ alkenyl, aryl and alkylaryl;

R$^{12}$ is selected from H, C$_{1-8}$ straight chain alkyl, branched alkyl, C$_{3-8}$ cycloalkyl, C$_{4-9}$ alkylcycloalkyl or cycloalkylalkyl, C$_{2-8}$ alkenyl, aryl, alkylaryl, (CH$_2$)$_n$NR$_{13}$R$_{14}$, (CH$_2$)$_m$SO$_3$H, and (CH$_2$)$_m$CO$_2$H, wherein n is 2 through 6 and m is 1 through 6;

R$^{13}$ and R$^{14}$ are each independently selected from H, C$_{1-8}$ straight chain alkyl, branched alkyl, C$_{2-8}$ alkenyl or cycloalkyl, or alkylcycloalkyl, or cycloalkylalkyl, or aryl or CH$_2$aryl, wherein each said aryl group or said aryl portion of said CH$_2$aryl group may be optionally substituted by up to four substituents in any position independently selected from:

F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$,, SCF$_3$, SCOCH$_3$, SCOC$_2$H$_5$, SCOC$_3$H$_7$, SCOC$_4$H$_9$, SO$_3$CH$_3$, SO$_3$C$_2$H$_5$, SO$_3$C$_3$H$_7$, SO$_3$C$_4$H$_9$, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and wherein when R$^{13}$ and/or R$^{14}$ contain an aryl ring substituted at two adjacent positions on said aryl ring, then said two adjacent positions can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure; or R$^{13}$ and R$^{14}$ form part of a 5, 6 or 7 membered saturated cyclic structure or 5,6 or 7 membered unsaturated cyclic structure, each such structure optionally containing up to four heteroatoms selected from O, N and S and wherein each said cyclic structure may be optionally substituted by up to four substituents in any position, each position independently selected from:

F, Cl, Br, I, CF$_3$, CCl$_3$, CH$_3$, C$_2$H$_5$, C$_3$H$_7$, C$_4$H$_9$, NH$_2$, NHCH$_3$, N(CH$_3$)$_2$, NHC$_2$H$_5$, N(C$_2$H$_5$)$_2$, NHC$_3$H$_7$, N(C$_3$H$_7$)$_2$, NHC$_4$H$_9$, N(C$_4$H$_9$)$_2$, NHCOH, NHCOCH$_3$, NHCOC$_2$H$_5$, NHCOC$_3$H$_7$, NHCOC$_4$H$_9$, NHSO$_2$CH$_3$, NHSO$_2$C$_2$H$_5$, NHSO$_2$C$_3$H$_7$, NHSO$_2$C$_4$H$_9$, OH, OCH$_3$, OC$_2$H$_5$, OC$_3$H$_7$, OC$_4$H$_7$, OC$_4$H$_9$, OC$_5$H$_9$, OC$_5$H$_{11}$, OC$_6$H$_{11}$, OC$_6$H$_{13}$, OCF$_3$, OCOCH$_3$, OCOC$_2$H$_5$, OCOC$_3$H$_7$, OCOC$_4$H$_9$, OSO$_2$CH$_3$, OSO$_2$C$_2$H$_5$, OSO$_2$C$_3$H$_7$, OSO$_2$C$_4$H$_9$, SH, SCH$_3$, SC$_2$H$_5$, SC$_3$H$_7$, SC$_4$H$_7$, SC$_4$H$_9$, SC$_5$H$_9$, SC$_5$H$_{11}$, SC$_6$H$_{11}$, SC$_6$H$_{13}$,, SCF$_3$, SCOCH$_3$, SCOC$_2$H$_5$, SCOC$_3$H$_7$, SCOC$_4$H$_9$, SO$_3$CH$_3$, SO$_3$C$_2$H$_5$, SO$_3$C$_3$H$_7$, SO$_3$C$_4$H$_9$, SO$_2$NH$_2$, SO$_2$NHCH$_3$, SO$_2$N(CH$_3$)$_2$, SO$_2$NHC$_2$H$_5$, SO$_2$N(C$_2$H$_5$)$_2$, SO$_2$NHC$_3$H$_7$, SO$_2$N(C$_3$H$_7$)$_2$, SO$_2$NHC$_4$H$_9$, SO$_2$N(C$_4$H$_9$)$_2$, NO$_2$, CN, COOCH$_3$, COOC$_2$H$_5$, COOC$_3$H$_7$, COOC$_4$H$_9$, COSCH$_3$, COSC$_2$H$_5$, COSC$_3$H$_7$, COSC$_4$H$_9$, CONH$_2$, CONHCH$_3$, CON(CH$_3$)$_2$, CONHC$_2$H$_5$, CON(C$_2$H$_5$)$_2$, CONHC$_3$H$_7$, CON(C$_3$H$_7$)$_2$, CONHC$_4$H$_9$, CON(C$_4$H$_9$)$_2$, and wherein when R$^{13}$ and R$^{14}$ form an aryl ring substituted at two adjacent positions on said aryl ring, then said two adjacent positions can be joined by a chain selected from CHCHCHCH, CH$_2$CH$_2$CH$_2$CH$_2$, CHCHCH$_2$, CH$_2$CH$_2$CH$_2$, CH$_2$CH$_2$, SCH$_2$S, SCH$_2$CH$_2$S, OCH$_2$O, or OCH$_2$CH$_2$O to form a bi-cyclic structure; and R$^{15}$ is selected from H, C$_{1-8}$ straight chain alkyl, branched alkyl, C$_{3-8}$ cycloalkyl, C$_{4-9}$ alkylcycloalkyl or cycloalkylalkyl, and C$_{2-8}$ alkenyl.

An aryl moiety can be a 5 or 6 membered aromatic heterocyclic ring (containing up to 4 hetero atoms independently selected from N, O, or S) or a 6 membered aromatic non-heterocyclic ring or a polycycle;

Examples of suitable C$_{1-8}$ alkyl groups include but art not limited to methyl, ethyl, n-propyl, i-propyl, n-butyl, and t-butyl.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Further disclosed is a method of modulating the GPR6 receptor by contacting said receptor with a small molecule structurally represented by the foregoing open chain 5 membered heteroaryl series.

8. Closed Chain 5 Membered Heteroaryl (Sub-series b)

As an eighth series of GPR6 inverse agonists, disclosed are "closed chain 5 memebered heteroaryl sub-series b" represented structurally as follows:

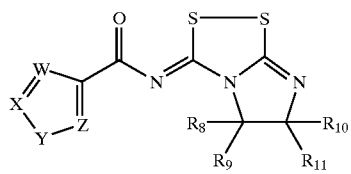

wherein

Y is selected from $NR^4$, O or S;

W, X, or Z are each independently selected from N or $CR^1$, $CR^2$, or $CR^3$, with the proviso that when Y is O and Z is N, then W is $CR^1$ and X is $CR^2$;

$R^1$, $R^2$, and $R^3$ are each independently selected from the following:

H, F, Cl, Br, I, $R^{12}$, $CF_3$, $CF_2R^{12}$, $CF_2CF_2$, $CCl_3$, $CCl_2R^{12}$, $CCl_2CCl_2R^{12}$, $NR^{13}R^{14}$, $NR^{15}COR^{12}$, $NR^{15}SO_2R^{12}$, $OR^{12}$, $OCF_3$, $OCF_2R^{12}$, $OCF_2CF_2R^{12}$, $OCOR^{12}$, $OSO_2R^{12}$, $OPO(OR^{12})_2$, $SR^{12}$, $SCF_3$, $SCF_2R^{12}$, $SCF_2CF_2R^{12}$, $SCOR^{12}$, $SO_3R^{12}$, $SO_2NR^{13}R^{14}$, $PO(OR^{12})_3$, $PO(OR^{12})_2R^{12}$, $NO_2$, CN, $CNR^{15}(NR^{13}R^{14})$, $CNR^{15}(SR^{12})$, $COOR^{12}$, $COSR^{12}$, $CONR^{13}R^{14}$, and wherein any two adjacent positions of $R^1$, $R^2$, $R^3$, $R^4$, and $R^5$ can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, or $OCH_2CH_2O$ to form a bi-cyclic structure;

$R^4$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $COR^5$, $CSR^5$, and $SO_2R^5$;

$R^5$, $R^6$ and $R^7$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^6$ and $R^7$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl $R^8$, $R^9$, $R^{10}$, and $R^{11}$ are each independently selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl and alkylaryl;

$R^{12}$ is selected from H, $C_{1-8}$ straight chain alkyl, branched alkyl, $C_{3-8}$ cycloalkyl, $C_{4-9}$ alkylcycloalkyl or cycloalkylalkyl, $C_{2-8}$ alkenyl, aryl, alkylaryl, $(CH_2)_n NR_{13}R_{14}$, $(CH_2)_m SO_3H$, and $(CH_2)_m CO_2H$, wherein n is 2 through 6 and m is 1 through 6;

$R^{13}$ and $R^{14}$ are each independently selected from H, $C_{1-8}$ straight chain alkyl, branched alkyl, $C_{2-8}$ alkenyl or cycloalkyl, or alkylcycloalkyl, or cycloalkylalkyl, or aryl or $CH_2$aryl, wherein each said aryl group or said aryl portion of said $CH_2$aryl group may be optionally substituted by up to four substituents in any position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$ $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and/or $R^{14}$ contain an aryl ring substituted at two adjacent positions on said aryl ring, then said two adjacent positions can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, or $OCH_2CH_2O$ to form a bi-cyclic structure; or $R^{13}$ and $R^{14}$ form part of a 5, 6 or 7 membered saturated cyclic structure or 5,6 or 7 membered unsaturated cyclic structure, each such structure optionally containing up to four heteroatoms selected from O, N and S and wherein each said cyclic structure may be optionally substituted by up to four substituents in any position, each position independently selected from:

F, Cl, Br, I, $CF_3$, $CCl_3$, $CH_3$, $C_2H_5$, $C_3H_7$, $C_4H_9$, $NH_2$, $NHCH_3$, $N(CH_3)_2$, $NHC_2H_5$, $N(C_2H_5)_2$, $NHC_3H_7$, $N(C_3H_7)_2$, $NHC_4H_9$, $N(C_4H_9)_2$, NHCOH, $NHCOCH_3$, $NHCOC_2H_5$, $NHCOC_3H_7$, $NHCOC_4H_9$, $NHSO_2CH_3$, $NHSO_2C_2H_5$, $NHSO_2C_3H_7$, $NHSO_2C_4H_9$, OH, $OCH_3$, $OC_2H_5$, $OC_3H_7$, $OC_4H_7$, $OC_4H_9$, $OC_5H_9$, $OC_5H_{11}$, $OC_6H_{11}$, $OC_6H_{13}$, $OCF_3$, $OCOCH_3$, $OCOC_2H_5$, $OCOC_3H_7$, $OCOC_4H_9$, $OSO_2CH_3$, $OSO_2C_2H_5$, $OSO_2C_3H_7$, $OSO_2C_4H_9$, SH, $SCH_3$, $SC_2H_5$, $SC_3H_7$, $SC_4H_7$, $SC_4H_9$, $SC_5H_9$, $SC_5H_{11}$, $SC_6H_{11}$, $SC_6H_{13}$, $SCF_3$, $SCOCH_3$, $SCOC_2H_5$, $SCOC_3H_7$, $SCOC_4H_9$, $SO_3CH_3$, $SO_3C_2H_5$, $SO_3C_3H_7$, $SO_3C_4H_9$, $SO_2NH_2$, $SO_2NHCH_3$, $SO_2N(CH_3)_2$, $SO_2NHC_2H_5$, $SO_2N(C_2H_5)_2$, $SO_2NHC_3H_7$, $SO_2N(C_3H_7)_2$, $SO_2NHC_4H_9$, $SO_2N(C_4H_9)_2$, $NO_2$, CN, $COOCH_3$, $COOC_2H_5$, $COOC_3H_7$, $COOC_4H_9$, $COSCH_3$, $COSC_2H_5$, $COSC_3H_7$, $COSC_4H_9$, $CONH_2$, $CONHCH_3$, $CON(CH_3)_2$, $CONHC_2H_5$, $CON(C_2H_5)_2$, $CONHC_3H_7$, $CON(C_3H_7)_2$, $CONHC_4H_9$, $CON(C_4H_9)_2$, and wherein when $R^{13}$ and $R^{14}$ form an aryl ring substituted at two adjacent positions on said aryl ring, then said two adjacent positions can be joined by a chain selected from CHCHCHCH, $CH_2CH_2CH_2CH_2$, $CHCHCH_2$, $CH_2CH_2CH_2$, $CH_2CH_2$, $SCH_2S$, $SCH_2CH_2S$, $OCH_2O$, and $OCH_2CH_2O$ to form a bi-cyclic structure; and $R^{15}$ is selected from H, $C_{1-8}$ straight chain alkyl, branched alkyl, $C_{3-8}$ cycloalkyl, $C_{4-9}$ alkylcycloalkyl or cycloalkylalkyl, and $C_{2-8}$ alkenyl.

An aryl moiety can be a 5 or 6 membered aromatic heterocyclic ring (containing up to 4 hetero atoms independently selected from N, O, or S) or a 6 membered aromatic non-heterocyclic ring or a polycycle;

Examples of suitable $C_{1-8}$ alkyl groups include but art not limited to methyl, ethyl, n-propyl, i-propyl, n-butyl, and t-butyl.

Examples of 5 or 6 membered ring moieties include, but are not restricted to, phenyl, furanyl, thienyl, imidazolyl, pyridyl, pyrrolyl, oxazolyl, isoxazolyl, triazolyl, pyrazolyl, tetrazolyl, thiazolyl and isothiazolyl. Examples of polycycle moieties include, but are not restricted to, naphthyl, benzothiazolyl, benzofuranyl, benzimidazolyl, quinolyl, isoquinolyl, indolyl, quinoxalinyl, quinazolinyl and benzothienyl.

Further disclosed is a method of modulating the GPR6 receptor by contacting said receptor with a small molecule structurally represented by the foregoing closed chain 5 memebered heteroaryl sub-series Example 8A Synthetic Approaches The compounds disclosed in this invention may be readily prepared according to a variety of synthetic manipulations, all of which would be familiar to one skilled in the art. In the general syntheses set forth below, the labeled substituents "R" have the same identifications as set out in the definitions of the compounds disclosed below.

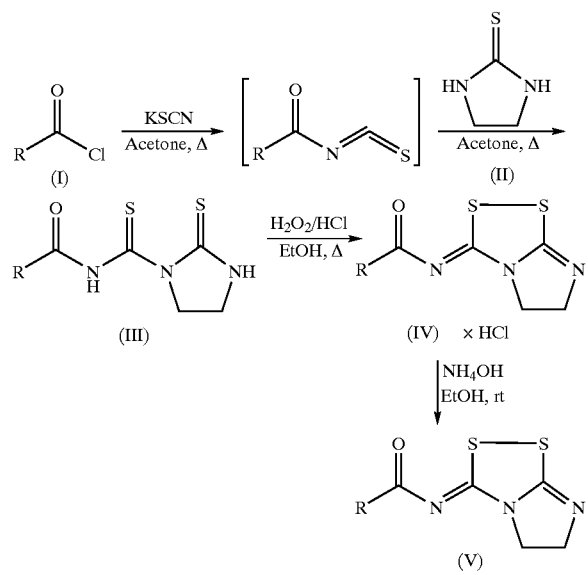

In the approaches disclosed below, "Protocol A" is the synthetic approach up to formula (III), and "Protocol B" is the synthetic approach up to formula (V). It is noted that in each of these approaches, the compound produced by Protocol A is then in turn used as the starting material for the compound produced by Protocol B.

Compounds of formulas (III) and (V) or a solvate or physiologically functional derivative thereof can be used as active ingredients in pharmaceutical compositions, specifically as a GPR6 inverse agonists. The data developed herein supports the conclusion that GPR6 inverse agonists are of use for the treatment or prophylaxis of clinical obesity or overweight disorders in mammals, including, but not limited to, human. Compounds of the formulas (III) and (V) may be administered by oral, sublingual, parenteral, rectal, topical administration or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

In addition to the neutral forms of compounds of formulas (III) and (V) by appropriate addition of an ionizable substituent, which does not alter the receptor specificity of the compound, physiologically acceptable salts of the compounds may also be formed and used as therapeutic agents. Different amounts of the compounds of formulas (III) and (V) will be required to achieve the desired biological effect. The amount will depend on factors such as the specific compound, the use for which it is intended, the means of administration, and the condition of the treated individual—all of these dosing parameters are within the level of one of ordinary skill in the medicinal arts. A typical dose may be expected to fall in the range of 0.001 to 200 mg per kilogram of body weight of the mammal. Unit doses may contain from 1 to 200 mg of the compounds of formula (III) or (V) and may be administered one or more times a day, individually or in multiples. In the case of the salt or solvate of a compound of formulas (III) and (V), the dose is based on the cation (for salts) or the unsolvated compound.

Compositions, including, but not limited to, pharmaceutical compositions, comprising at least one compound of formulas (III) and (V) and/or an acceptable salt or solvate thereof (e.g., a pharmaceutically acceptable salt or solvate) as an active ingredient combined with at least one carrier or excipient (e.g., pharmaceutical carrier or excipient). Pharmaceutical compositions may be used in the treatment of clinical conditions for which a GPR6 inverse agonist is indicated. At least one compound of formula (III) and (V) may be combined with the carrier in either solid or liquid form in a unit dose formulation. The pharmaceutical carrier must be compatible with the other ingredients in the composition and must be tolerated by the individual recipient. Other physiologically active ingredients may be incorporated into the pharmaceutical composition of the invention if desired, and if such ingredients are compatible with the other ingredients in the composition. Formulations may be prepared by any suitable method, typically by uniformly mixing the active compound(s) with liquids or finely divided solid carriers, or both, in the required proportions, and then, if necessary, forming the resulting mixture into a desired shape.

Conventional excipients, such as binding agents, fillers, acceptable wetting agents, tabletting lubricants, and disintegrants may be used in tablets and capsules for oral administration. Liquid preparations for oral administration may be in the form of solutions, emulsions, aqueous or oily suspensions, and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives, and flavorings and colorants may be added to the liquid preparations. Parenteral dosage forms may be prepared by dissolving the compound of the invention in a suitable liquid vehicle and filter sterilizing the solution before filling and sealing an appropriate vial or ampoule. These are just a few examples of the many appropriate methods well known in the art for preparing dosage forms.

It is noted that when the GPR6 inverse agonists are utilized as active ingredients in a pharmaceutical composition, these are not intended for use only in humans, but in other non-human mammals as well. Indeed, recent advances in the area of animal health-care mandate that consideration be given for the use of GPR6 inverse agonists for the treatment of obesity in domestic animals (e.g., cats and dogs), and GPR6 agonists in other domestic animals where no disease or disorder is evident (e.g., food-oriented animals such as cows, chickens, fish, etc.). Those of ordinary skill in the art are readily credited with understanding the utility of such compounds in such settings.

Below are structural representations of compounds that have been determined to exhibit similar GPR6 inverse agonist activity and selectivity as that of compound ARE112.
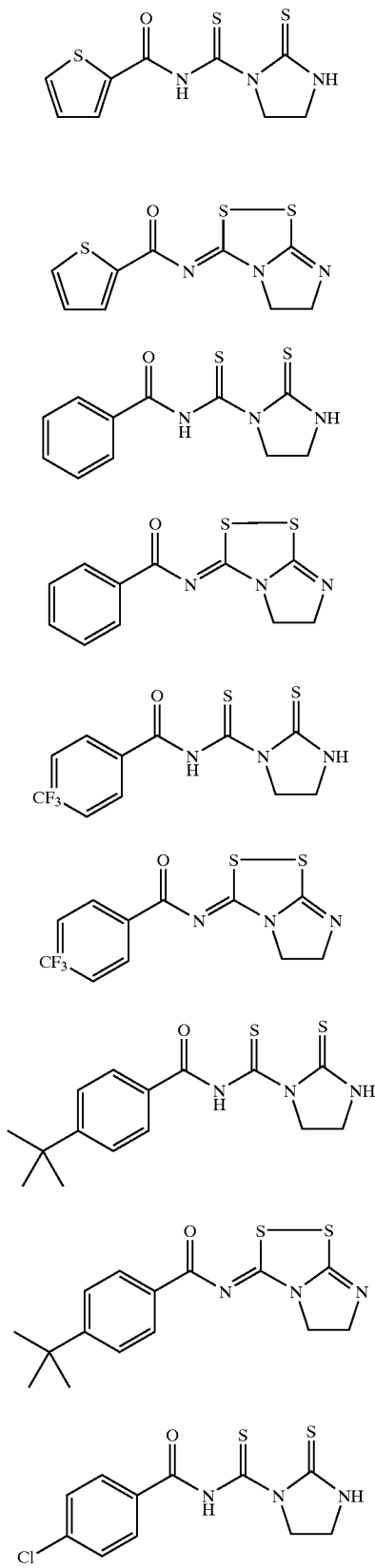

-continued
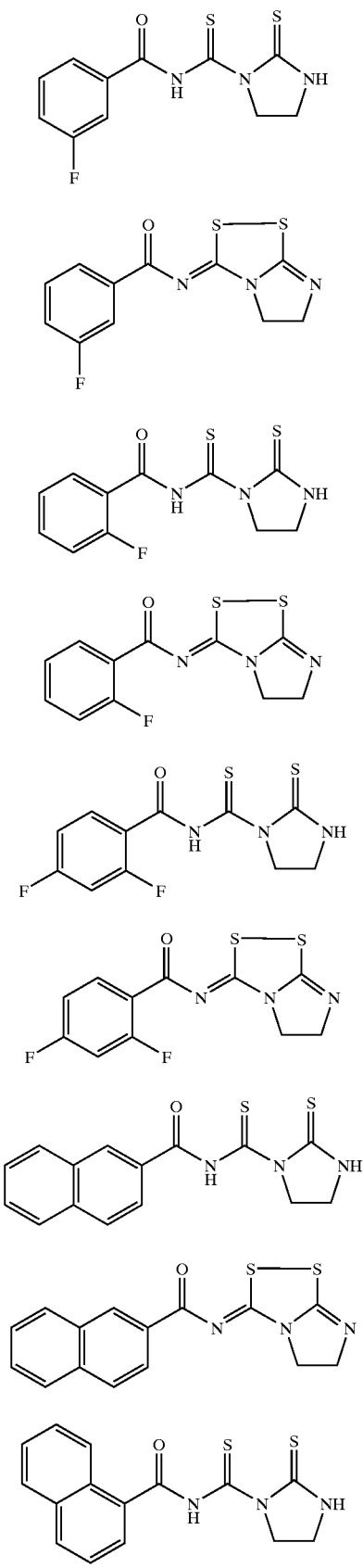
ARE129
ARE130
ARE131
ARE132
ARE133
ARE134
ARE135
ARE136
ARE137
-continued
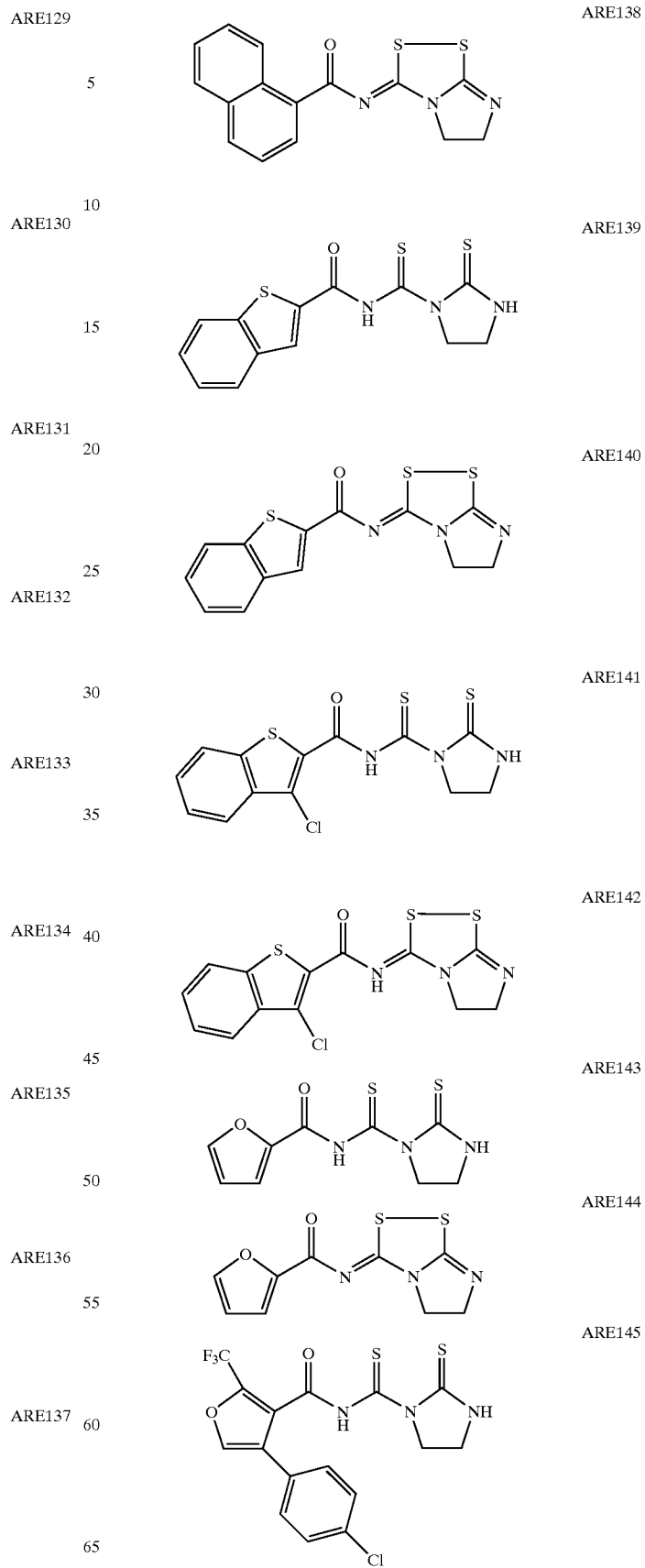
ARE138
ARE139
ARE140
ARE141
ARE142
ARE143
ARE144
ARE145

-continued

ARE146
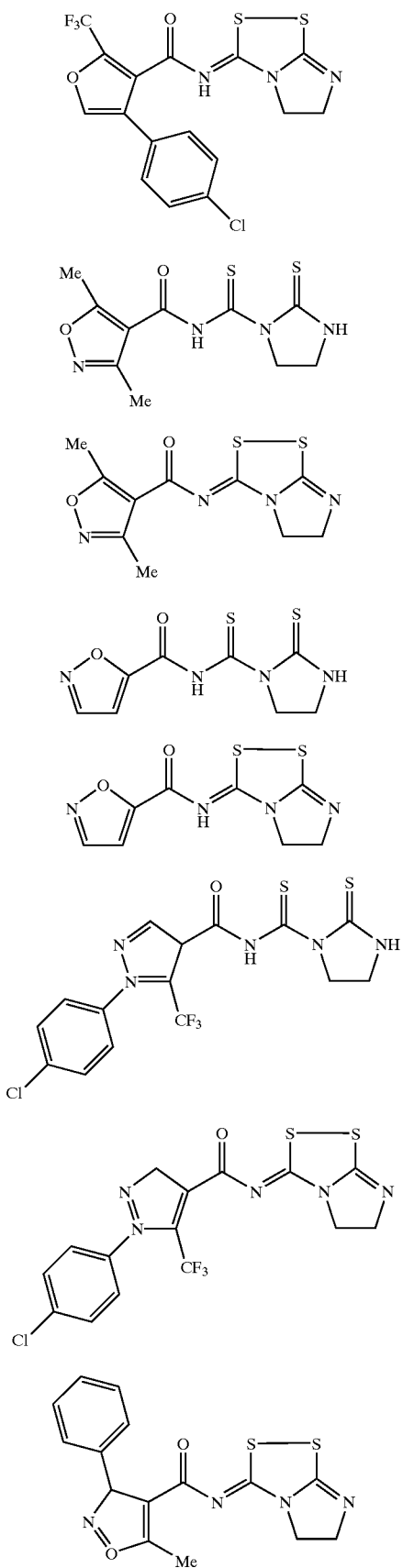

ARE147

ARE148

ARE149

ARE150

ARE151

ARE152

ARE153

-continued

ARE154
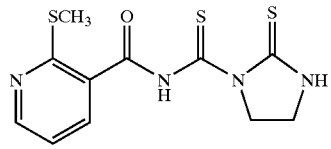

ARE155
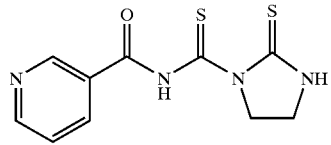

ARE156
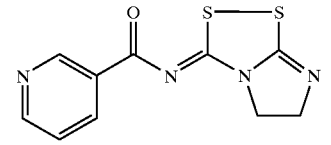

Example 8B

Ppreparation of Compounds ARE111–ARE156

Mass spectra were recorded on a PE Sciex API 150 EX mass spectrometer linked to a Shimadzu dual pump (two LC8 pumps) HPLC using a CombiScreen C18 reverse phase column (50 mm×4.6 mm i.d.). Gradient elution was over 5 minutes with 95% water containing 0.05% TFA)/5% acetonitrile containing 0.35% TFA down to 100% acetonitrile at a flow rate of 3.5 ml/min. Samples eluting from the HPLC were routinely monitored at 220 nm using a Shimadzu SPD-10AVP detector unless otherwise stated. All reagents were purchased from commercial sources.

Preparation 1

Preparation and Analysis of ARE111 N-(2-thioxo-imidazolidine-1-carbothioyl)-thiophene-2-carboxamide and ARE112 N-(5,6-dihydro-3H-imidazo[2,1-c]-1,2,4-dithiazol-3-ylidene)-thiophen-2-carboxamide The following synthetic protocols were used to generate each of the compounds below:
Protocol A To a freshly prepared solution of potassium thiocyanate (2.14 g, 22 mmol) in dry acetone (80 ml), thiophene-2-carbonyl chloride (2.93 g, 20 mmol) was added dropwise at room temperature; the reaction mixture was then heated under a reflux for 15 min to give thiophene-2-carbonyl isothiocyanate in situ as a yellow suspension. The heating was stopped and 2-imidazolidinethione (2.04 g, 20 mmol) was added. The mixture was then heated under reflux for an additional 4 hours before being allowed to cool followed by stirring at room temperature overnight (15 hours). 50 ml of water was added and the mixture was further stirred at room temperature for a few minutes. The resulting precipitate was collected by filtration and washed with water, water/methanol (1:1) and methanol to give the compound ARE111 (2.865 g, yield=53%)

Mass spectrum: m/z (%): 272.0 (M+H, 100) Calculated for $C_9H_9N_3OS_3$=270.98

HPLC retention time: 2.97 min
Protocol B

To a suspension of ARE111 (2 g, 7.37 mmol) in ethanol (30 ml) was added concentrated hydrochloric acid (0.75 ml ) and 30% hydrogen peroxide (2 ml). The reaction mixture was heated under reflux in an oil bath for two hours while the yellow suspension turned white. The resulting precipitate was collected by filtration and washed with ethanol to give the hydrochloride salt that was then suspended in ethanol (20 ml) and treated with 28–30% ammonium hydroxide (1 ml) to yield the free base. The reaction mixture was stirred at room temperature for 20 min then the resulting precipitate was collected by filtration, washed with ethanol and dried to give the compound ARE112 (1.304 g, yield= 66%) as a yellowish solid.

MS (ES+): m/z (%): 270 (M+H, 100)

Mass spectrum: m/z (%): 270.0 (M+H, 100) Calculated for $C_9H_7N_3OS_3$=268.98

HPLC retention time: 2.36 min

Preparation 2

Preparation and Analysis of ARE113 N-(2-thioxo-imidazolidine-1-carbothioyl)-benzamide and ARE114 N-(5,6-dihydro-3H-imidazo[2,1-c]-1,2,4-dithiazol-3-ylidene)-benzamide The procedure of Protocol A above was followed, using benzoyl chloride instead of thiophene-2-carbonyl chloride, to yield ARE113 as a yellowish solid.

Mass spectrum: m/z (%): 266.0 (M+H, 100) Calculated for $C_{11}H_{11}N_3OS_2$=265.02

HPLC retention time: 3.29 min

The procedure of Protocol B above was followed, using ARE113 instead of ARE111, to yield ARE114 as a white solid.

Mass spectrum: m/z (%): 263.8 (M+H, 61) Calculated for $C_{11}H_9N_3OS_2$=263.02

HPLC retention time: 2.53 min

Preparation 3

Preparation and Analysis of ARE115 N-(2-thioxo-imidazolidine-1-carbothioyl)-4-trifluoromethylbenzamide and ARE116 N-(5,6-dihydro-3H-imidazo[2,1-c]-1,2,4-dithiazol-3-ylidene)-4-trifluoromethylbenzamide Protocol A was followed using 4-(trifluoromethyl)benzoyl chloride instead of thiophen-2-carbonyl chloride to yield ARE115 as a yellowish solid.

Mass spectrum: m/z (%): 173.0 (100), 334.2 (M+H, 83) Calculated for $C_{12}H_{10}F_3N_3OS_2$=333.01

HPLC retention time: 3.69 min

Protocol B was followed using ARE115 instead of ARE111 to yield ARE116 as a white solid.

Mass spectrum: m/z (%):332.0 (M+H, 100) Calculated for $C_{12}H_{12}F_3N_3OS_2$=331.01

HPLC retention time: 3.28 min

Preparation 4

Preparation and Analysis of ARE117 N-(2-thioxo-imidazolidine-1-carbothioyl)-4-tert-butylbenzamide and ARE118 N-(5,6-dihydro-3H-imidazo[2,1-c]-1,2,4-dithiazol-3-ylidene)-4-tert-butylbenzamide Protocol A was followed using 4-tert-butylbenzoyl chloride instead of thiophene-2-carbonyl chloride to yield compound ARE117 as a yellowish solid.

Mass spectrum: m/z (%): 161.0 (100), 322.0 (M+H, 53) Calculated for $C_{15}H_{19}N_3OS_2$=321.45

HPLC retention time: 3.97 min

Protocol B was followed using ARE117 instead of ARE111 to yield compound ARE118 as a white solid.

Mass spectrum: m/z (%): 320.0 (M+H, 100) Calculated for $C_{15}H_{17}N_3OS_2$=319.45

HPLC retention time: 3.72 min

Preparation 5

Preparation and Analysis of ARE119 N-(2-thioxo-imidazolidine-1-carbothioyl)-4-chlorobenzamide and ARE120 N-(5,6-dihydro-3H-imidazo[2,1-c]-1,2,4-dithiazol-3-ylidene)-4-chlorobenzamide Protocol A was followed using -4-chlorobenzoyl chloride instead of thiophene-2-carbonyl chloride to yield compound ARE119 as a yellowish solid.

Mass spectrum: m/z (%): 139.0 (100), 300.0 (M+H, 56) Calculated for $C_{11}H_{10}ClN_3OS_2$=298.98

HPLC retention time: 3.52 min

Protocol B was followed using ARE119 instead of ARE111 to yield compound ARE120 as a white solid.

Mass spectrum: m/z (%): 139.0 (100), 298.0 (M+H, 72) Calculated for $C_{11}H_8ClN_3OS_2$=296.98

HPLC retention time: 3.01 min

Preparation 6

Preparation and Analysis of ARE121 N-(2-thioxo-imidazolidine-1-carbothioyl)-4-methoxybenzamide and ARE122 N-(5,6-dihydro-3H-imidazo[2,1-c]-1,2,4-dithiazol-3-ylidene)-4-methoxybenzamide Protocol A was followed using 4-methoxybenzoyl chloride instead of thiophene-2-carbonyl chloride to yield compound ARE121 as a yellowish solid.

Mass spectrum: m/z (%):135.0 (100), 296.2 (M+H, 39) Calculated for $C_{12}H_{13}N_3O_2S_2$=295.03

HPLC retention time 3.37 min

Protocol B was followed using ARE121 instead of ARE111 to yield compound ARE122 as a white solid.

Mass spectrum: m/z (%): 294.0 (M+H, 100) Calculated for $C_{12}H_{11}N_3O_2S_2$=293.03

HPLC retention time: 2.89 min

Preparation 7

Preparation and Analysis of ARE123 N-(2-thioxo-imidazolidine-1-carbothioyl)-3-methoxybenzamide and ARE124 N-(5,6-dihydro-3H-imidazo[2,1-c]-1,2,4-dithiazol-3-ylidene)-3-methoxybenzamide Protocol A was followed using 3-methoxybenzoyl chloride instead of thiophene-2-carbonyl chloride to yield compound ARE123 as a yellowish solid.

Mass spectrum: m/z (%): 135.2 (100), 296.2 (M+H, 53) Calculated for $C_{12}H_{13}N_3O_2S_2$=295.03

HPLC retention time: 3.20 min

Protocol B was followed using ARE123 instead of ARE111 to yield ARE124 as a white solid.

Mass spectrum: m/z (%): 294.0 (M+H, 100) Calculated for $C_{12}H_{11}N_3O_2S_2$=293.03

BPLC retention time: 2.94 min

Preparation 8

Preparation and Analysis of ARE125 N-(2-thioxo-imidazolidine-1-carbothioyl)-3-methylbenzamide and ARE126 N-(5,6-dihydro-3H-imidazo[2,1-c]-1,2,4-dithiazol-3-ylidene)-3-methylbenzamide Protocol A was followed using 3-methylbenzoyl chloride instead of thiophene-2-carbonyl chloride to yield compound ARE125 as a yellowish solid.

Mass spectrum: m/z (%): 119.4 (100), 280.0 (M+H, 47) Calculated for $C_{12}H_{13}N_3OS_2$=279.03

HPLC retention time: 3.59 min

Protocol B was followed using ARE125 instead of ARE111 to yield compound ARE126 as a white solid.

Mass spectrum: m/z (%): 278.0 (M+H, 100) Calculated for $C_{12}H_{11}N_3OS_2$=277.03

HPLC retention time: 3.11 min

Preparation 9

Preparation and Analysis of ARE127 N-(2-thioxo-imidazolidine-1-carbothioyl)-4-fluorobenzamide and ARE128 N-(5,6-dihydro-3H-imidazo[2,1-c]-1,2,4-dithiazol-3-ylidene)-4-fluorobenzamide Protocol A was followed using 4-fluorobenzoyl chloride instead of thiophene-2-carbonyl chloride to yield compound ARE127 as a yellowish solid.

Mass spectrum: m/z (%): 123.2 (100), 284.2 (M+H, 75) Calculated for $C_{11}H_{10}FN_3OS_2$=283.01

Protocol B was followed using ARE127 instead of ARE111 to compound ARE128 as a white solid.

Mass spectrum: m/z (%/o): 123.2 (100), 282.2 (M+H, 90) Calculated for $C_{11}H_8FN_3OS_2$=281.01

HPLC retention time: 2.68 min

Preparation 10

Preparation an Analysis of ARE129 N-(2-thioxo-imidazolidine-1-carbothioyl)-3-fluorobenzamide and ARE130 N-(5,6-dihydro-3H-imidazo[2,1-c]-1,2,4-dithiazol-3-ylidene)-3-fluorobenzamide Protocol A was followed using 3-fluorobenzoyl chloride instead of thiophene-2-carbonyl chloride to yield compound ARE129 as a yellowish solid.

Mass spectrum: m/z (%): 123.2 (100), 284.3 (M+H, 61) Calculated for $C_{11}H_{10}FN_3OS_2$=283.01

HPLC retention time: 3.24 min

Protocol B was followed using ARE129 instead of ARE111 to yield compound ARE130 as a white solid.

Mass spectrum: m/z (%): 282.2 (M+H, 100) Calculated for $C_{11}H_8FN_3OS_2$=281.01

HPLC retention time: 2.97 min

Preparation 11

Preparation and Analysis of ARE131 N-(2-thioxo-imidazolidine-1-carbothioyl)-2-fluorobenzamide and ARE132 N-(5,6-dihydro-3H-imidazo[2,1-c]-1,2,4-dithiazol-3-ylidene)-2-fluorobenzamide Protocol A was followed using 2-fluorobenzoyl chloride instead of thiophene-2-carbonyl chloride to yield compound ARE131 as a yellowish solid.

Mass spectrum: m/z (%): 123.2 (100), 284.0 (M+H, 67) Calculated for $C_{11}H_{10}FN_3OS_2$=283.01

HPLC retention time: 3.07 min

Protocol B was followed using ARE131 instead of ARE111 to yield compound ARE132 as a white solid.

Mass spectrum: m/z (%): 282.2 (M+H, 100) Calculated for $C_{11}H_8FN_3OS_2$=281.01

HPLC retention time: 2.72 min

Preparation 12

Preparation an Analysis of ARE133 N-(2-thioxo-imidazolidine-1-carbothioyl)-2,4-difluorobenzamide and ARE134 N-(5,6-dihydro-3H-imidazo[2,1-c]-1,2,4-dithiazol-3-ylidene)-2,4-difluorobenzamide Protocol A was followed using 2,4-difluorobenzoyl chloride instead of thiophene-2-carbonyl chloride to yield compound ARE133 as a yellow solid.

Mass spectrum: m/z (%): 141.0 (100), 302.2 (M+H, 39) Calculated for $C_{11}H_9F_2N_3OS_2$301.00

HPLC retention time: 3.23 min

Protocol B was followed using ARE133 instead of ARE111 to yield compound ARE134 as a white solid.

Mass spectrum: m/z (%): 300.0 (M+H, 100) Calculated for $C_{11}H_7F_2N_3OS_2$=299.00

HPLC retention time: 2.86 min

Preparation 13

Preparation and Analysis of ARE135 N-(2-thioxo-imidazolidine-1-carbothioyl)-naphthyl-2-carboxamide and ARE136 N-(5,6-dihydro-3H-imidazo[2,1-c]-1,2,4-dithiazol-3-ylidene)-naphthyl-carboxamide Protocol A was followed using 2-naphthoyl chloride instead of thiophene-2-carbonyl chloride to yield compound ARE135 as a yellowish solid.

Mass spectrum: m/z (%): 155.0(100), 316.0 (M+H, 56) Calculated for $C_{15}H_{13}N_3OS_2$=315.40

HPLC retention time: 3.88 min

Protocol B was followed using ARE135 instead of ARE111 to yield compound ARE136 as a white solid.

Mass spectrum: m/z (%): 314.0 (M+H, 100) Calculated for $C_{15}H_{11}N_3OS_2$=313.40

HPLC retention time: 3.41 min

Preparation 14

Preparation and Analysis of ARE137 N-(2-thioxo-imidazolidine-1-carbothioyl)-naphthyl-1-carboxamide and ARE138 N-(5,6-dihydro-3H-imidazo[2,1-c]-1,2,4-dithiazol-3-ylidene)-naphthyl-1-carboxamide Protocol A was followed using 1-naphthoyl chloride instead of thiophene-2-carbonyl chloride to yield compound ARE137 as a yellow solid.

Mass spectrum: m/z (%): 155.0 (100), 316.0 (M+H, 39) Calculated for $C_{15}H_{13}N_3OS_2$=315.40

HPLC retention time: 3.80 min

Protocol B will be followed using ARE137 instead of ARE111 to yield ARE138 as a white solid.

Mass spectrum: m/z (%): 314.0 (M+H, 100) Calculated for $C_{15}H_{13}N_3OS_2$=313.05

HPLC retention time: 3.38 min

Preparation 15

Preparation and Analysis of ARE139 N-(2-thioxo-imidazolidine-1-carbothioyl)-benzothiophen-2-carboxamide and ARE140 N-(5,6-dihydro-3H-imidazo[2,1-c]-1,2,4-dithiazol-3-ylidene)-benzothiophen-2-carboxamide Protocol A was followed using benzo[b]thiophene-2-carbonyl chloride instead of thiophene-2-carbonyl chloride, to yield compound ARE139 as a yellowish solid.

Mass spectrum: m/z (%):160.8 (100), 321.8 (M+H, 51) Calculated for $C_{13}H_{11}N_3OS_3$=320.99

HPLC retention time: 3.92 min

Protocol B was followed using ARE139 instead of ARE111 to yield compound ARE140 as a white solid.

Mass spectrum: n/z (%): 320.0 (M+H, 100) Calculated for $C_{13}H_9N_3OS_3$=318.99

HPLC retention time: 3.47 min

Preparation 16

Preparation and Analysis of ARE143 N-(2-thioxo-imidazolidine-1-carbothioyl)-furan-2-carboxamide and ARE144 N-(5,6dihydro-3H-imidazo[2,1-c]-1,2,4-dithiazol-3-ylidene)furan-2-carboxamide Protocol A was followed using 2-furoyl chloride instead of thiophene-2-carbonyl chloride to yield compound ARE143 as a yellowish solid.

Mass spectrum: m/z (%/): 256.0 (M+H, 100) Calculated for $C_9H_9N_3O_2S_2=255.00$ HPLC retention time: 2.86 min Protocol B was followed using ARE143 instead of ARE111 to yield compound ARE144 as a white solid.

Mass spectrum: mn/z (%): 254.2 (M+H, 100) Calculated for $C_9H_9N_3O_2S_2=253.00$ HPLC retention time: 2.13 min

Preparation 17

Preparation and Analysis of ARE148 N-(5,6-dihydro-3H-imidazo[2,1-c]-1,2,4-dithiazol-3-ylidene)-2,5-dimethylisoxazole-4carboxamide Protocol A was followed using 2,5-dimethylisoxazole-4-carbonyl chloride instead of thiophene-2-carbonyl chloride to yield compound N-(2-thioxo-imidazolidine-1-carbothioyl)-2,5-dimethylisoxazole-4-carboxamide as a yellowish solid.

Protocol B was then followed using the above compound instead of ARE111 to yield compound ARE148 as a white solid.

Mass spectrum: m/z (%): 283.0 (M+H, 100) Calculated for $C_{10}H_{10}N_4O_2S_2=282.02$ HPLC retention time: 2.53 min

Preparation 18

Preparation and Analysis of ARE149 N-(2-thioxo-imidazolidine-1-carbothioyl)-isoxazole-3-carboxamide and ARE150 N-(5,6dihydro-3H-imidazo[2,1-c]-1,2,4-dithiazol-3-ylidene)-isoxazole-3-carboxamide Protocol A was followed using isoxazole-3-carbonyl chloride instead of thiophene-2-carbonyl chloride to yield compound ARE149 as a yellowish solid.

Mass spectrum: m/z (%): 257.0 (M+H, 100) Calculated for $C_8H_8N_4O_2S_2=255.99$ HPLC retention time: 2.76 min Protocol B was followed using ARE149 instead of ARE111 to yield compound ARE150 as a white solid.

Mass spectrum: m/z (%): 255.2 (M+H, 100) Calculated for $C_8H_6N_4O_2S_2=253.99$ HPLC retention time: 2.09 min

Preparation 19

Preparation and Analysis of ARE151 N-(2-thioxo-imidazolidine-1-carbothioyl)-2-(4-chlorophenyl)-3-(trifluoromethyl)pyrazole-4-carboxamide and ARE152 N-(5,6dihydro-3H-imidazo[2,1-c]-1,2,4-dithiazol-3-ylidene)-2-(4-chlorophenyl)-3-(trifluoromethyl)pyrazole-4-carboxamide Protocol A was followed using 2-(4-chlorophenyl)-3-(trifluoromethyl)pyrazole-4-carbonyl chloride instead of thiophene-2-carbonyl chloride to yield compound ARE151 as a yellowish solid.

Mass spectrum: m/z (%): 273.0 (100), 434.0 (M+H, 76) Calculated for $C_{15}H_{11}ClF_3N_4O_2S_2=432.99$ HPLC retention time: 4.25 min Protocol B was followed using ARE151 instead of ARE111 to yield compound ARE152 as a white solid.

Mass spectrum: m/z (%): 431.8 (M+H, 100) Calculated for $C_{15}H_9ClF_3N_5OS_2=431.8$ HPLC retention time: 3.77 min

Preparation 20

Preparation and Analysis of ARE153 N-(2-thioxo-imidazolidine-1-carbothioyl)-2-(4-chlorophenyl)-3-(trifluoromethyl)pyrazole-4-carboxamide Protocol A was followed using 2-methyl-5-phenylisoxazole-4-carbonyl chloride instead of thiophene-2-carbonyl chloride to yield compound ARE153 as a yellowish solid.

Mass spectrum: m/z (%): 344.8 (100), (M+H, 100) Calculated for $C_{15}H_{12}N_4O_2S_2=344.42$ HPLC retention time: 4.57 min

Preparation 21

Preparation and Analysis of ARE154 N-(2-thioxo-imidazolidine-1-carbothioyl)-pyridine-2-methylthio-3-carboxamide Protocol A was followed using pyridine2-methylthio-3-carbonyl chloride instead of thiophene-2-carbonyl chloride to yield compound ARE154 as a yellowish solid.

Mass spectrum: m/z (%): 152.2 (100),313.2 (M+H, 100) Calculated for $C_{11}H_{12}N_4OS_3=312.02$ HPLC retention time: 3.31 min

Preparation 22

Preparation and Analysis of ARE155 N-(2-thioxo-imidazolidine-1-carbothioyl)-pyridine-3-carboxamide and ARE156 N-(5,6-dihydro-3H-imidazo[2,1-c]-1,2,4-dithiazol-3-ylidene)-pyridine-3-carboxamide Protocol A was followed using pyridine-3-carbonyl chloride instead of thiophene-2-carbonyl chloride to yield compound ARE155 as a yellowish solid.

Mass spectrum: m/z (%): 165.0 (100), 267.0 (M+H, 50) Calculated for $C_{10}H_{10}N_4OS_2=266.03$ HPLC retention time: 2.29 min Protocol B was followed using ARE155 instead of ARE111 to yield compound ARE156 as a white solid.

Mass spectrum: mn/z (%): 265.0 (M+H, 100) Calculated for $C_{10}H_8N_4OS_2=264.01$ HPLC retention time: 1.87 min Different embodiments of the invention will consist of different constitutively active receptors, expression systems, different assays, and different compounds. Those skilled in the art will understand which receptors to use with which expression systems and assay methods. All are considered within the scope of the teaching of this invention. In addition, those skilled in the art will recognize that various modifications, additions, substitutions, and variations to the illustrative examples set forth herein can be made without departing from the spirit of the invention and are, therefore, considered within the scope of the invention. Indeed, with the assay systems disclosed above, as well as the relationship between the receptor GPR6 and feeding behavior, one of ordinary skill in the art is readily credited with the ability to directly identify small molecule inverse agonists, agonists and partial agonists to the receptor—for example, we note that the phrase "small molecule GPR6 inverse agonist" is not limited by the specific compounds disclosed herein.

All patent documents, applications, and printed publications cited throughout this patent document, including provisional applications and regular patent applications, unless otherwise indicated, are incorporated herein in their entirety by reference. Modifications and extension of the disclosed inventions that are within the purview of the skilled artisan are encompassed within the above disclosure and the claims that follow.

What is claimed is:
1. A small molecule, GPR6 inverse agonist selected from the group consisting of the following structures:
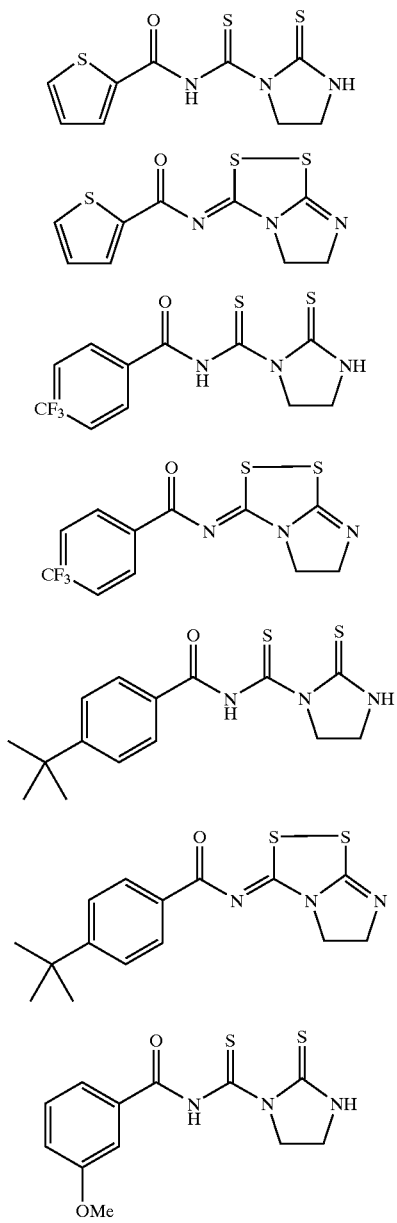
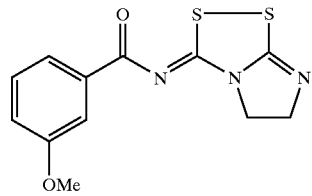
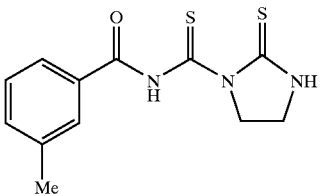
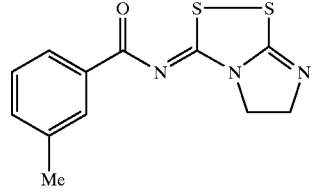
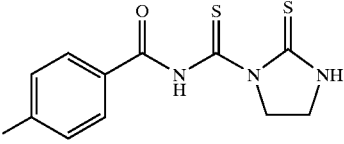
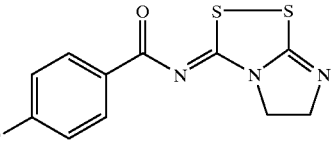
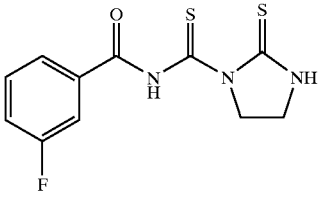

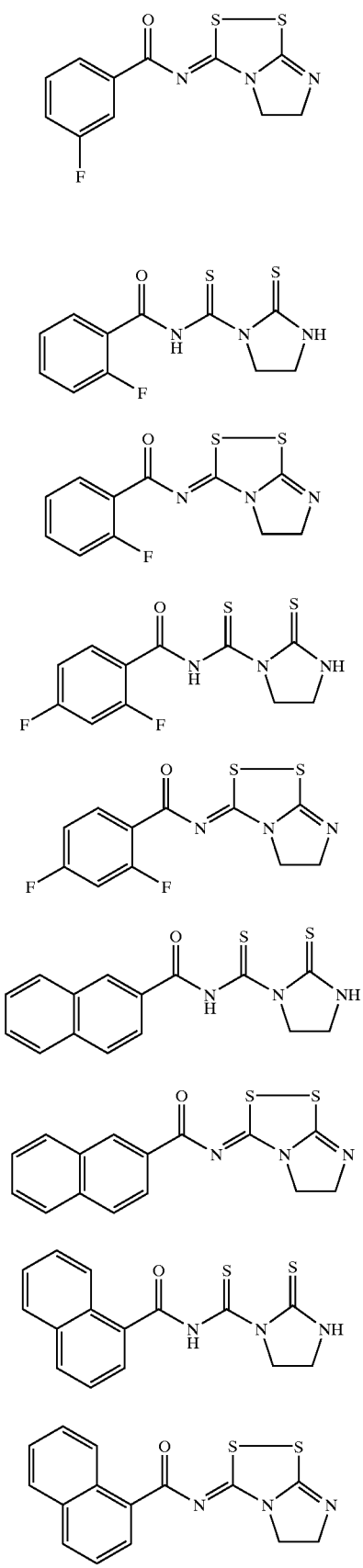

-continued
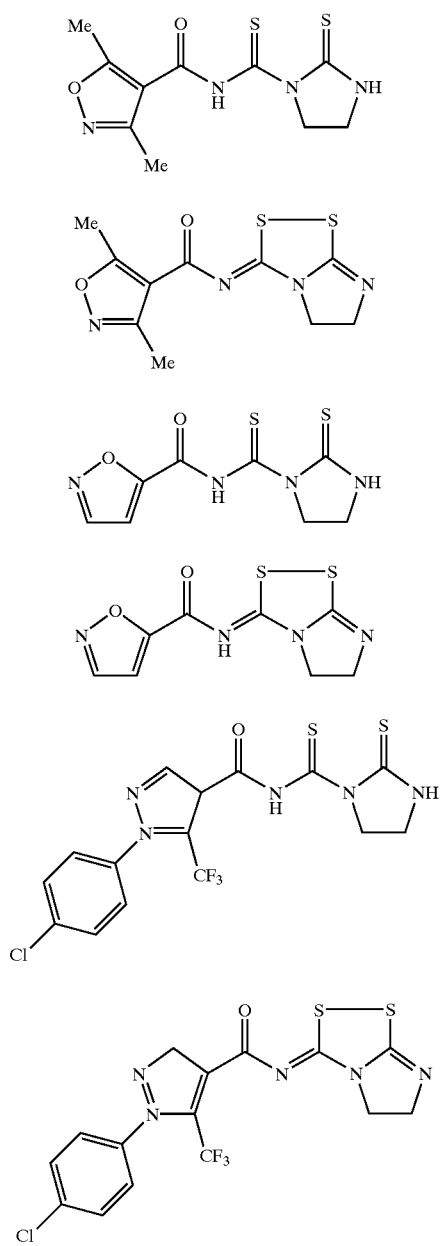
ARE147
ARE148
ARE149
ARE150
ARE151
ARE152
-continued
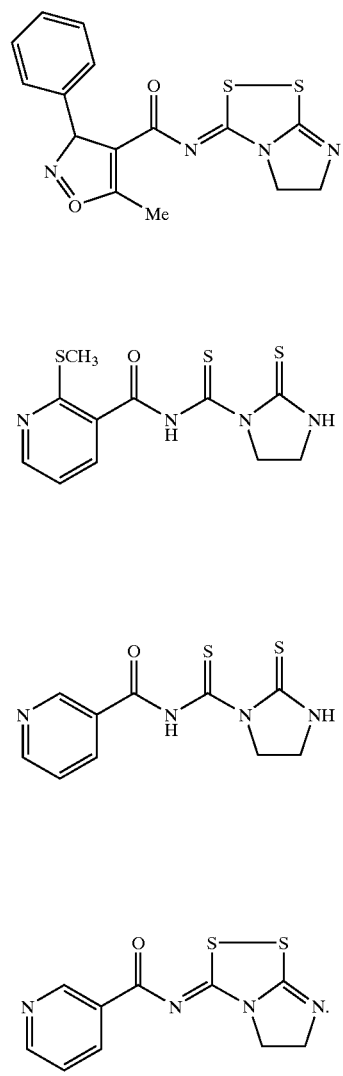
ARE153
ARE154
ARE155
ARE156
* * * * *